(12) United States Patent
Lanning et al.

(10) Patent No.: US 12,105,048 B2
(45) Date of Patent: Oct. 1, 2024

(54) MULTI-PART NONTOXIC PRINTED BATTERIES

(71) Applicant: Lyten, Inc., San Jose, CA (US)

(72) Inventors: Bruce Lanning, Littleton, CO (US); Michael W. Stowell, Sunnyvale, CA (US); Carlos Montalvo, Cambria, CA (US); Daniel Cook, Woodside, CA (US); Sung H. Lim, Mountain View, CA (US); Shreeyukta Singh, San Jose, CA (US); John Chmiola, San Francisco, CA (US)

(73) Assignee: Lyten, Inc., San Jose, CA (US)

( * ) Notice: Subject to any disclaimer, the term of this patent is extended or adjusted under 35 U.S.C. 154(b) by 0 days.

(21) Appl. No.: 18/154,235

(22) Filed: Jan. 13, 2023

(65) Prior Publication Data

US 2023/0168223 A1    Jun. 1, 2023

Related U.S. Application Data

(63) Continuation of application No. 16/740,381, filed on Jan. 10, 2020, now Pat. No. 11,555,799, which is a
(Continued)

(51) Int. Cl.
*G01N 27/414* (2006.01)
*B01J 20/28* (2006.01)
(Continued)

(52) U.S. Cl.
CPC .... *G01N 27/4141* (2013.01); *B01J 20/28066* (2013.01); *C01B 32/182* (2017.08);
(Continued)

(58) Field of Classification Search
CPC ............ G01N 27/4141; G01N 27/127; G01N 27/4045; G01N 29/036; G01N 33/0037;
(Continued)

(56) References Cited

U.S. PATENT DOCUMENTS

| | | | |
|---|---|---|---|
| 5,436,093 A | 7/1995 | Huang et al. | |
| 6,031,711 A | 2/2000 | Tennent et al. | |

(Continued)

FOREIGN PATENT DOCUMENTS

| | | |
|---|---|---|
| CA | 2032137 C | 11/1990 |
| CN | 100541870 | 9/2009 |

(Continued)

OTHER PUBLICATIONS

International Search Report and Written Opinion dated Mar. 14, 2023, for PCT Appl. No. PCT/US2022/037905; 17 pages.
(Continued)

*Primary Examiner* — Daniel S Gatewood
(74) *Attorney, Agent, or Firm* — Paradice & Li LLP

(57) ABSTRACT

A battery-powered analyte sensing system includes a printed battery and an analyte sensor. The printed battery includes an anode composed of a non-toxic biocompatible metal, a first carbon-based current collector in electrical contact with the anode, a three-dimensional hierarchical mesoporous carbon-based cathode, a second carbon-based current collector, and an electrolyte layer disposed between the anode and the cathode, the electrolyte layer configured to activate the printed battery when the electrolyte is released into one or both the anode and the cathode. The analyte sensor includes a sensing material and a reactive chemistry additive in the sensing material.

10 Claims, 45 Drawing Sheets

Related U.S. Application Data continuation-in-part of application No. 16/706,542, filed on Dec. 6, 2019, now Pat. No. 10,955,378, which is a continuation of application No. 16/239,423, filed on Jan. 3, 2019, now Pat. No. 10,502,705.

(60) Provisional application No. 62/942,103, filed on Nov. 30, 2019, provisional application No. 62/926,225, filed on Oct. 25, 2019, provisional application No. 62/894,621, filed on Aug. 30, 2019, provisional application No. 62/790,932, filed on Jan. 10, 2019, provisional application No. 62/613,716, filed on Jan. 4, 2018.

(51) Int. Cl.
| | |
|---|---|
| *B33Y 80/00* | (2015.01) |
| *C01B 32/182* | (2017.01) |
| *C23C 20/00* | (2006.01) |
| *G01N 27/12* | (2006.01) |
| *G01N 27/404* | (2006.01) |
| *G01N 29/036* | (2006.01) |
| *G01N 33/00* | (2006.01) |
| *H01M 4/62* | (2006.01) |
| *H01M 4/66* | (2006.01) |
| *H01M 4/80* | (2006.01) |
| *H01M 4/96* | (2006.01) |
| *H01M 10/0525* | (2010.01) |
| *H01M 12/08* | (2006.01) |

(52) U.S. Cl.
CPC ............... *C23C 20/00* (2013.01); *H01M 4/62* (2013.01); *H01M 4/625* (2013.01); *H01M 4/663* (2013.01); *H01M 4/667* (2013.01); *H01M 4/801* (2013.01); *H01M 4/96* (2013.01); *H01M 10/0525* (2013.01); *H01M 12/08* (2013.01); *B33Y 80/00* (2014.12); *C01B 2204/04* (2013.01); *C01B 2204/22* (2013.01); *C01B 2204/32* (2013.01); *G01N 27/127* (2013.01); *G01N 27/4045* (2013.01); *G01N 29/036* (2013.01); *G01N 33/0037* (2013.01); *G01N 33/0039* (2013.01); *G01N 33/004* (2013.01); *G01N 33/0044* (2013.01); *G01N 2291/014* (2013.01)

(58) Field of Classification Search
CPC .............. G01N 33/0039; G01N 33/004; G01N 33/0044; G01N 2291/014; B01J 20/28066; C01B 32/182; C01B 2204/04; C01B 2204/22; C01B 2204/32; C23C 20/00; H01M 4/62; H01M 4/625; H01M 4/663; H01M 4/667; H01M 4/801; H01M 4/96; H01M 10/0525; H01M 12/08; B33Y 80/00; Y02A 50/20; Y02E 60/10
See application file for complete search history.

(56) References Cited

U.S. PATENT DOCUMENTS

| | | | |
|---|---|---|---|
| 6,099,960 A | 8/2000 | Tennent et al. | |
| 6,757,154 B2 | 6/2004 | Reynolds, III et al. | |
| 6,830,595 B2 | 12/2004 | Reynolds, III | |
| 7,071,258 B1 | 7/2006 | Jang et al. | |
| 7,206,189 B2 | 4/2007 | Reynolds, III | |
| 7,465,519 B2 | 12/2008 | Tang et al. | |
| 7,623,340 B1 | 11/2009 | Song et al. | |
| 7,824,651 B2 | 11/2010 | Zhamu et al. | |
| 7,842,421 B2 | 11/2010 | Mikhaylik | |
| 7,875,219 B2 | 1/2011 | Zhamu et al. | |
| 8,119,288 B2 | 2/2012 | Zhamu et al. | |
| 8,132,746 B2 | 3/2012 | Zhamu et al. | |
| 8,241,793 B2 | 8/2012 | Zhamu et al. | |
| 8,415,054 B2 | 4/2013 | Skotheim et al. | |
| 8,497,225 B2 | 7/2013 | Zhamu et al. | |
| 8,524,067 B2 | 9/2013 | Zhamu et al. | |
| 8,617,748 B2 | 12/2013 | Mikhaylik et al. | |
| 8,624,222 B2 | 1/2014 | Liu et al. | |
| 8,748,043 B2 | 1/2014 | Mikhaylik | |
| 8,936,870 B2 | 1/2015 | Affinito et al. | |
| 8,968,924 B2 | 3/2015 | Bosnyak et al. | |
| 9,005,809 B2 | 4/2015 | Wilkening et al. | |
| 9,034,421 B2 | 5/2015 | Mikhaylik et al. | |
| 9,040,201 B2 | 5/2015 | Affinito et al. | |
| 9,190,667 B2 | 11/2015 | Zhamu et al. | |
| 9,190,694 B2 | 11/2015 | Lopez et al. | |
| 9,246,185 B2 | 1/2016 | Kretschmar et al. | |
| 9,419,274 B2 | 8/2016 | Wilkening et al. | |
| 9,577,243 B2 | 2/2017 | Schmidt et al. | |
| 9,742,030 B2 | 8/2017 | Wright et al. | |
| 9,819,053 B1 | 11/2017 | Zimmerman | |
| 10,020,494 B2 | 7/2018 | Wang et al. | |
| 10,083,801 B2 | 9/2018 | Zhamu et al. | |
| 10,530,011 B1 | 1/2020 | MacKenzie et al. | |
| 2009/0022649 A1 | 1/2009 | Zhamu et al. | |
| 2009/0028777 A1 | 1/2009 | Zhamu et al. | |
| 2011/0059343 A1 | 3/2011 | McKinney et al. | |
| 2013/0122380 A1 | 5/2013 | Visco et al. | |
| 2014/0057179 A1 | 2/2014 | Yushin et al. | |
| 2014/0255799 A1 | 9/2014 | Anandan et al. | |
| 2015/0210558 A1 | 7/2015 | Dickinson et al. | |
| 2015/0291431 A1 | 10/2015 | Tang et al. | |
| 2016/0207291 A1 | 7/2016 | Dimitrakopoulos et al. | |
| 2016/0207688 A1 | 7/2016 | Sebastian et al. | |
| 2017/0062821 A1 | 3/2017 | Tour et al. | |
| 2019/0288334 A1 | 9/2019 | Wright et al. | |

FOREIGN PATENT DOCUMENTS

| | | |
|---|---|---|
| JP | 2016532566 A | 10/2016 |
| JP | 2020194792 A | 12/2020 |
| KR | 10-2017-0139914 A | 12/2017 |
| WO | 2016/061216 A1 | 4/2016 |
| WO | 2018122368 A1 | 7/2018 |

OTHER PUBLICATIONS

K.S. Novoselov et al."Electric Field Effect in Atomically Thin Carbon Films" Science; 306(5696), pp. 666-669; Oct. 22, 2004.
T. Takamura et al."A key technology to improve the cyclic performances of carbonaceous materials for lithium secondary battery anodes" Science Direst Journal of Power Sources vol. 68, Issue 1, Sep. 1997, pp. 114-119.
J. Rothlisberger et al. "Ab Initio Molecular Dynamics Investigation of Singlet C2H2Li2: Determination of the Ground State Structure and Observation of LiH Intermediates" J. American Chemical Society 1995, 117, 42-48.
C. Menachem et al. "Characterization of Lithiated Natural Graphite Before and After Mild Oxidation" Science Direct Journal of Power Sources vol. 76, Issue 2, Dec. 1, 1998, pp. 180-185.
C. Menachem et al. "Characterization of modified NG7 graphite as an improved anode for lithius-ion batteries" Science Direct Journal of Power Sources vol. 68, Issue 2, Oct. 1997, pp. 277-282.
Y. Ein-Eli et al. "Chemical Oxidation: A Route to Enhanced Capacity in Li-Ion Graphite Anodes" Journal of the Electrochemical Society 1997 vol. 144, issue 9, pp. 2968-2973.
P. Maguire et al. "Continuous In-flight Synthesis for On-Demand Delivery of Ligand-Free Colloidal Gold Nanoparticles", Nano Letters; 17(3); pp. 1336-1343; Mar. 8, 2017.
S. Dabrowska et al. "Current Trends in the Development of Microwave Reactors for the Synthesis of Nanomaterials in Laboratories and Industries: A Review" Crystals; 8(10); Oct. 2018; p. 379.
M. Zheng et al."Activated graphene with tailored pore structure parameters for long cycle-life lithium-sulfur batteries" Nano Res. 2017, 10(12): 4305-4317.
J.S. Xue et al."Dramatic Effect of Oxidation on Lithium Insertion in Carbons Made from Epoxy Resins" Journal of the Electrochemical Society 1995 vol. 142, issue 11, 3668-3677.

(56) References Cited

OTHER PUBLICATIONS

F. Disma et al."Effect of Mechanical Grinding on the Lithium Intercalation Process in Graphites and Soft Carbons" Journal of the Electrochemical Society 1996 vol. 143, issue 12, 3959-3972.
Y. Wu et al."Effects of catalytic oxidation on the electrochemical performance of common natural graphite as an anode material for lithium ion batteries" Science Direct Electrochemistry Communications vol. 2, Issue 4, Apr. 1, 2000, pp. 272-275.
K.H. An et al."Electrochemical Properties of High-Power Supercapacitors Using Single-Walled Carbon Nanotube Electrodes" Advanced Functional Materials/vol. 11, Issue 5. Oct. 2, 2001.
Y. Qiu et al."Explosive thermal reduction of graphene oxide-based materials: mechanism and safety implications" NIH Public Access Author Manuscript School of Engineering, Brown University, 182 Hope St., Providence, RI, USA, 02912. Carbon NY. Jun. 2014; 72: 215-223. doi: 10.1016/j.carbon.2014.02.005.
R. Yazami et al."High reversible capacity carbon-lithium negative electrode in polymer electrolyte" Science Direct Journal of Power Sources vol. 54, Issue 2, Apr. 1995 pp. 411-415.
T. Zheng et al."High-Capacity Carbons Prepared from Phenolic Resin for Anodes of Lithium-Ion Batteries" Journal of the Electrochemical Society 1995 vol. 142, issue 11, L211-L214.
Z. Lu et al."Improving Li anode performance by a porous 3D carbon paper host with plasma assisted sponge carbon coating" Energy Storage Materials 11 (2018) 47-56.
S. Zhang "Liquid electrolyte lithium/sulfur battery: Fundamental chemistry, problems, and solutions" Science Direct. Journal of Power Sources vol. 231, Jun. 1, 2013, pp. 153-162.
R. Korthauer (Ed.) "Lithium-Ion Batteries: Basics and Applications" Publisher, Springer-Verlag Berlin Heidelberg Copyright Aug. 7, 2018.
H. Buqa et al. "Modified carbons for improved anodes in lithium ion cells" Science Direct Journal of Power Sources vol. 97-98, Jul. 2001, pp. 122-125.
E. Lee et al. "Li Absorption and Intercalation in Single Layer Graphene and Few Layer Graphene by First Principles" NANO Letters; 12(9), pp. 4624-4628; Sep. 12, 2012.
Y. Shi et al. "Material and Structural Design of Novel Binder Systems for High-Energy, High-Power Lithium-Ion Batteries" Published as part of the Accounts of Chemical Research special issue "Energy Storage: Complexities AmongMaterials and Interfaces at Multiple Length Scales". DOI: 10.1021/acs.accounts.7b00402 Acc. Chem. Res. 2017, 50, 2642-2652.
K. Ji et al. "Lithium intercalation into bilayer graphene" Nature Communications; 19(1); pp. 1-10; Jan. 17, 2019.
K. Ji et al. "Lithium intercalation into bilayer graphene" Nature Communications (2019) 10:275 | https://doi.org/10.1038/s41467-018-07942-z | www.nature.com/naturecommunications.
K. Jurewicz et al. "Supercapacitors from nanotubes/polypyrrole composites" Science Direct Chemical Physics Letters vol. 347, Issues 1-3, Oct. 2001, pp. 36-40.
J.E. Huang et al. "Well-dispersed single-walled carbon nanotube/polyaniline composite films" Science Dierct Carbon vol. 41, Issue 14, 2003, pp. 2731-2736.

A. Mistry et al. ""Shuttle" in Polysulfide Shuttle: Friend or Foe?" Journal of Physical Chemistry C; 122(42); pp. 23845-23851; Oct. 5, 2018.
I. Son et al., "Graphene balls for lithium rechargeable batteries with fast charging and high volumetric energy densities", Nature Communications; 8(1); pp. 1-11; Nov. 16, 2017.
H. Wang et al., "Graphene-Wrapped sulfur particles as a rechargeable lithium-sulfur battery cathode material with high capacity and cycling stability", Nano Letters; 11(7); pp. 2644-2647; Jul. 13, 2011.
Y. Lee et al., "High-Energy Long-Cycling All-Solid-State Lithium Metal Batteries Enabled by Silver-Carbon Composite Anodes", Nature Energy; 5(4); pp. 299-308; Apr. 2020.
Zhou, I. et al., "Recent developments on and prospects for electrode materials with hierarchical structures for lithium-ion batteries", Advanced Energy Materials; 8(6); p. 1701415; Feb. 2018.
Rodrigues, M. et al., "A materials perspective on Li-ion batteries at extreme temperatures", Nature Energy; 2(8); pp. 1-4; Jul. 24, 2017.
Zhang, H. et al., "Three-dimensional bicontinuous ultrafast-charge and -discharge bulk battery electrodes", Nature Nanotechnology; 6(5); pp. 277-281; May 2011.
Agostini, M. et al., "A high-power and fast charging Li-ion battery with outstanding cycle-life", Scientific Reports; 7(1); pp. 1-7; Apr. 24, 2017.
Shaibani, M., et al., "Expansion-tolerant architectures for stable cycling of ultrahigh-loading sulfur cathodes in lithium-sulfur batteries", Science Advances; 6(eaay2757); 11 pages; Jan. 3, 2020.
Liu, R., et al., "A self-standing, UV-cured semi-interpenetrating polymer network reinforced composite gel electrolytes for dendrite-suppressing lithium ion batteries", Journal of Materiomics; 5(2); pp. 185-194; Jun. 1, 2019.
Pathak, R., et al., "Fluorinated hybrid solid-electrolyte-interphase for dendrite-free lithium deposition", Nature Communications; 11(1); pp. 1-10; Jan. 3, 2020.
Bhattacharya, M., "Polymer Nanocomposites—A Comparison between Carbon Nanotubes, Graphene, and Clay as Nanofillers", Materials; 9(4); p. 262; Apr. 2016.
Fu, J., et al., "Flexible High-Energy Polymer-Electrolyte-Based Rechargeable Zinc-Air Batteries", Advanced Materials; 27(37); pp. 5617-5622; Oct. 2015.
Mishra, A., et al., "Electrode materials for lithium-ion batteries", Materials Science for Energy Technologies; 1(2); pp. 182-187; Dec. 1, 2018.
Guo, B., et al., "Hierarchical N-Doped Porous Carbons for Zn-Air Batteries and Supercapacitors", Nano-Micro Letters; 12(1); p. 20; Jan. 1, 2020.
Zhang, J., et al., "3D-printed functional electrodes towards Zn-Air batteries", Materials Today Energy; 16; p. 100407; Jun. 1, 2020.
International Search (Partial) w/PCT/ISA/206 Inv. to Pay Addl. Fees dated Jul. 12, 2022, for PCT Application No. PCT/US2022/021275; 16 pages.
Zhong, M. et al., "A review of cathode materials and structures for rechargeable lithium-air batteries", Energy & Environmental Science, vol. 8, No. 8; Jun. 4, 2015; pp. 2144-2198.

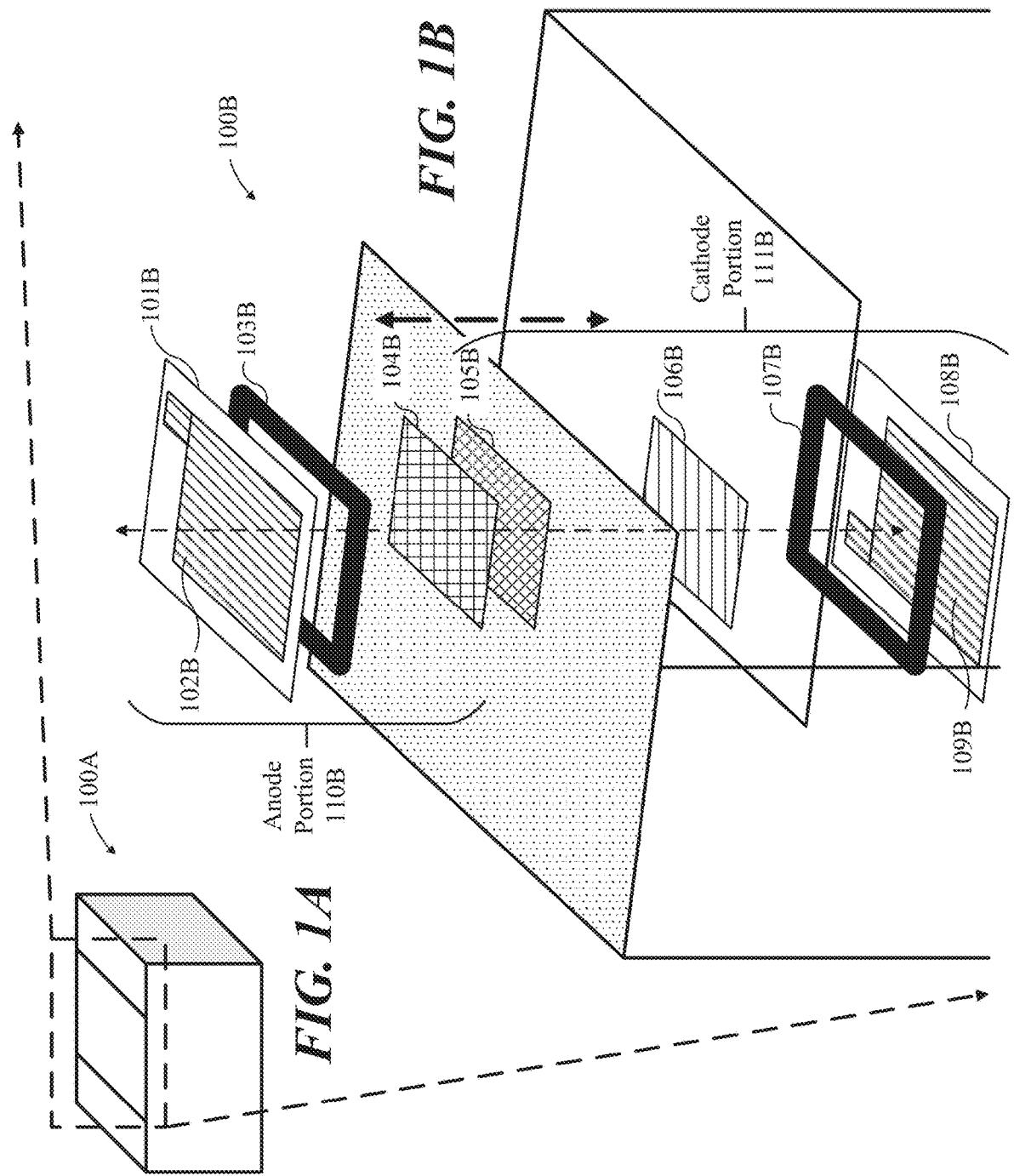

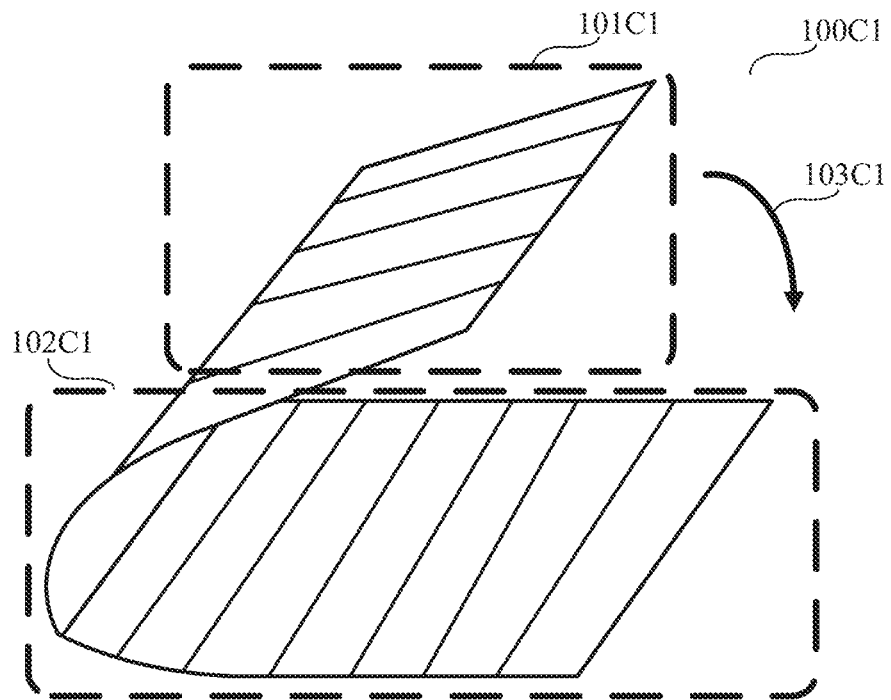
FIG. 1C1
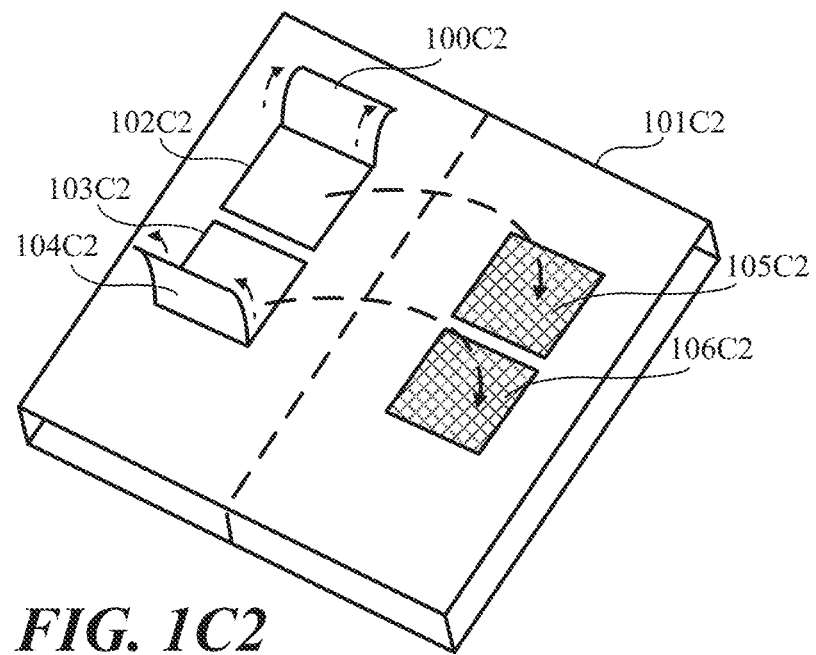
FIG. 1C2

3D Printed Battery Features 100D1

Stable, biodegradable components in benign, non-activated, isolated state (long storage life) prior to activation

- Dry carbon electrode with embedded conducting salt (ionic liquid)
- Active metal anode (Mg, Zn, Al, etc.) with textured surface; "interlocking" or matched (Velcro like) surface with cathode (Air and/or graphite- based), Ag/Cu chloride, $MnO_2$, or carbon/$MnO_2$ supercapacitor); Mg alloy serves as the anode because of its benign biological function and high theoretical capacity.
- Active cell voltage (1.5 to 3 volts)

Peel back, protective adhesive film with dual function:
- Protection of un-activated layers
- Sealing (protection) of cell and integrated electronics after activation
- Activation/release of electrolyte (ionic conductor)

Electrolyte (semi-solid and/or gel) type compound
- embedded in graphite (aqueous, low electrochemical window; 1.3 V), organic, or dry ionic liquid (4-6 V window)
- activated with hygroscopic additive or IL bound to polymer (polypyrrole) in carbon air cathode

Compatible with high volume, roll-to-roll (R2R) manufacturing (gravure/ screen print)

Process of activating battery can also provide opportunity for analyzing undesirable substance that may have been transferred to contact sensor

*FIG. 1D1*

3D Printed Battery Features 100D2

- Unique method of activation (permitting for dormant, long-term storage)

- Stable, biodegradable composite-based construction in non-activated isolated state

- Dry carbon electrode with an absorbent separator having an embedded electrically conductive salt (such as ionic liquid)

- Active metal-based anode (Mg, Zn, Al, etc.), having a textured surface area capable of interlocking with carbon-based scaffolded cathode

- Active cell voltage capabilities of ~ 3.0 V

*FIG. 1D2*

3D Printed Battery Features 100D3

Electrode fabrication (print with binder)

- Chitosan separator for aqueous (embedded chlorine nitrate is biodegradable) and ionic liquids
- Carboxymethyl cellulose (CMC) for organic electrolyte
- Current collector: metal laminated plastic with thin graphite layer to reduce contact resistance to electrode materials

Unique carbon features

- Hydrophobic/philic areas to inhibit and promote wetting and infiltration spatially across surface
- Hygroscopic: adsorption of water to activate battery
- Nanoscopic active materials, such as $MnO_2$ or hydrogen (for cathode), can be incorporated directly onto/into the surface of nanostructured carbons.
- In such a configuration, the nanostructured carbon substrate serves a high-surface-area, 3-D current collector for a $MnO_2$ coating (as an example), and defines the internal pore structure of the electrode, which facilitates the infiltration and rapid transport of electrolyte to a nanoscopic $MnO_2$ phase
- Adhesion between carbon textured films to create plane fastener-like devices

*FIG. 1D3*

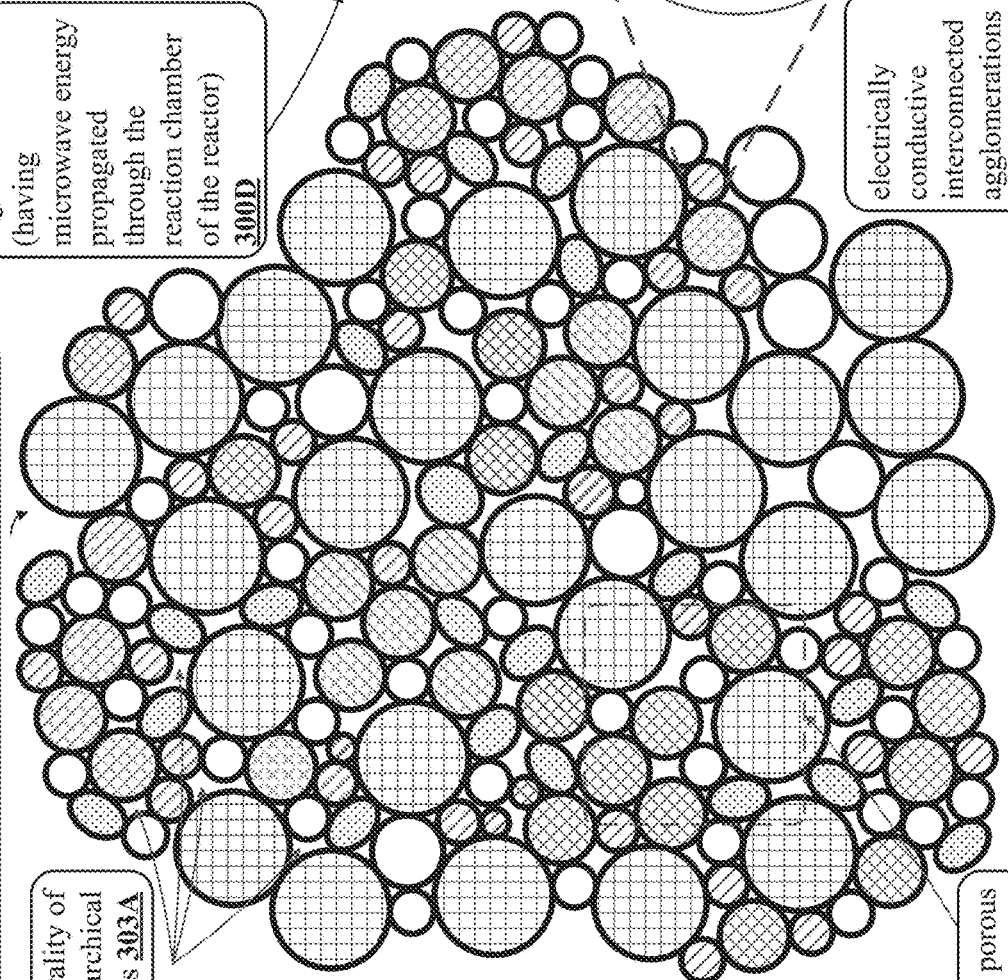
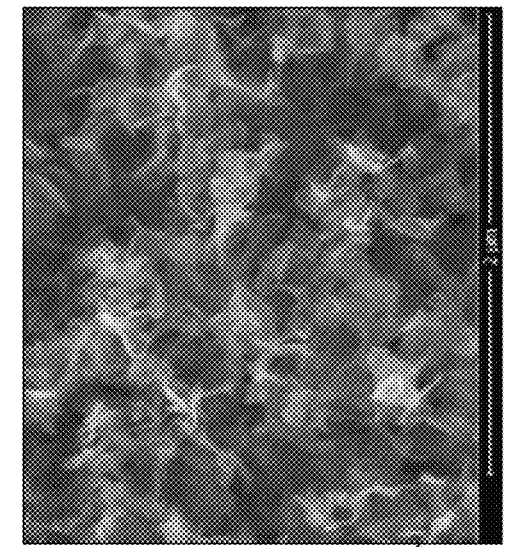
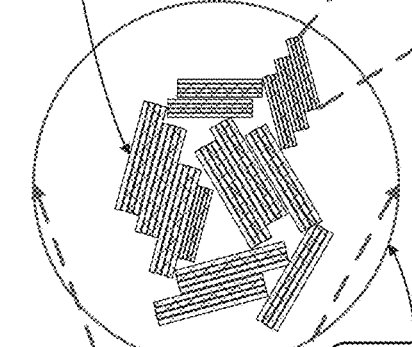
FIG. 3A
FIG. 3B
FIG. 3C
FIG. 3D

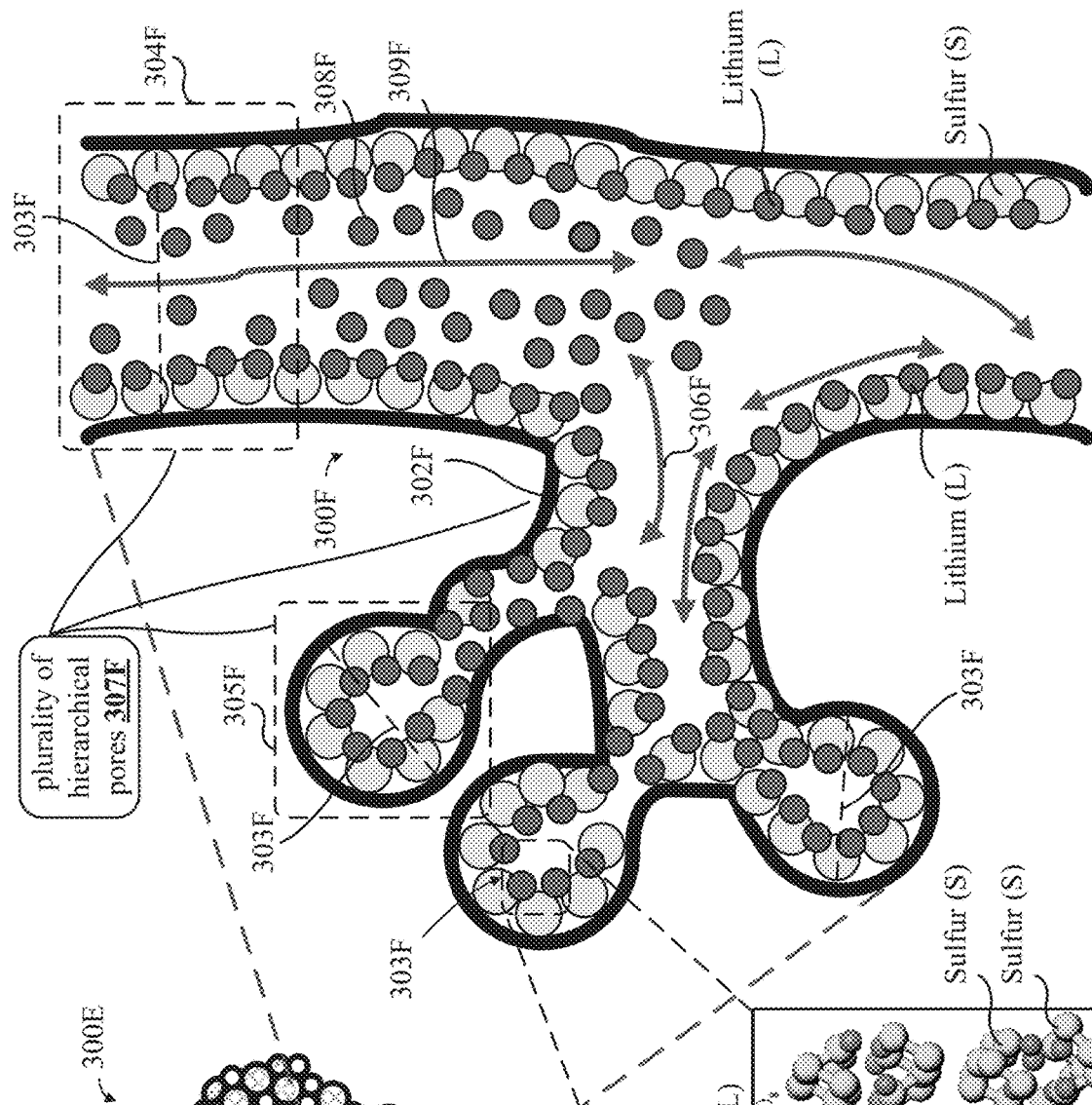
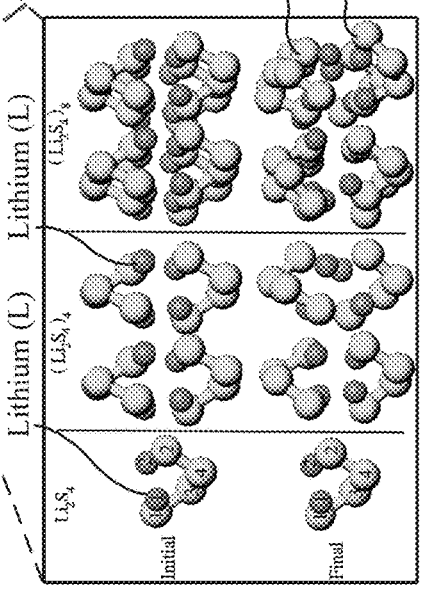
FIG. 3E
FIG. 3F

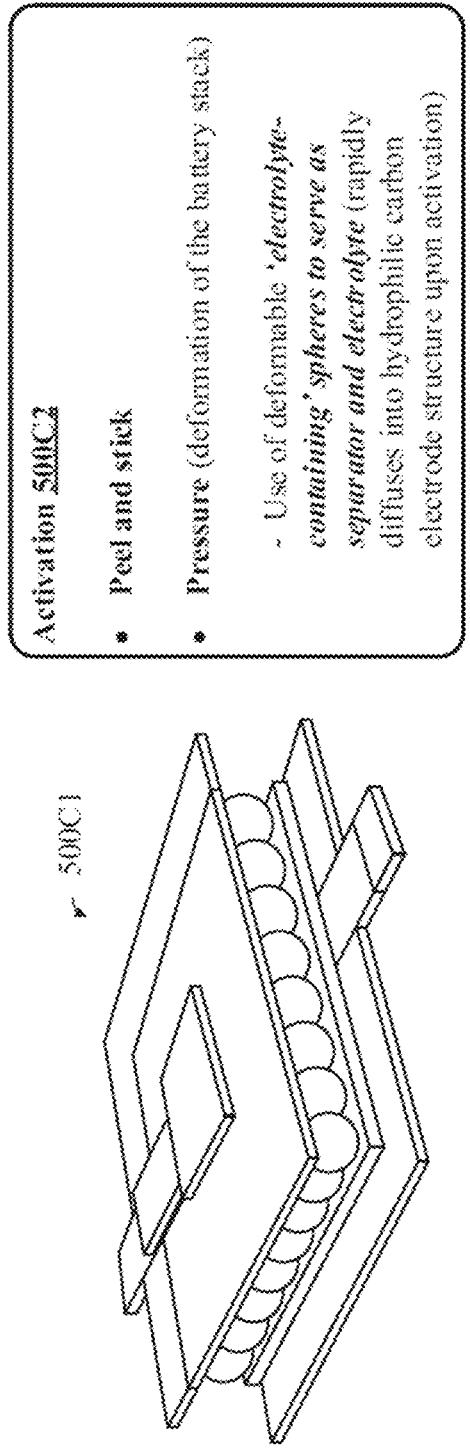
FIG. 5C1
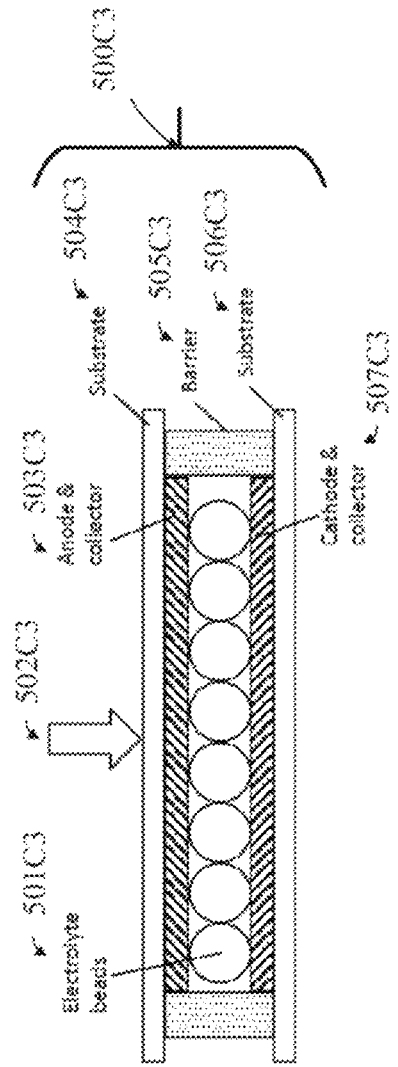
Activation 500C2
- Peel and stick
- Pressure (deformation of the battery stack)
  - Use of deformable 'electrolyte-containing' spheres to serve as separator and electrolyte (rapidly diffuses into hydrophilic carbon electrode structure upon activation)
FIG. 5C2
FIG. 5C3

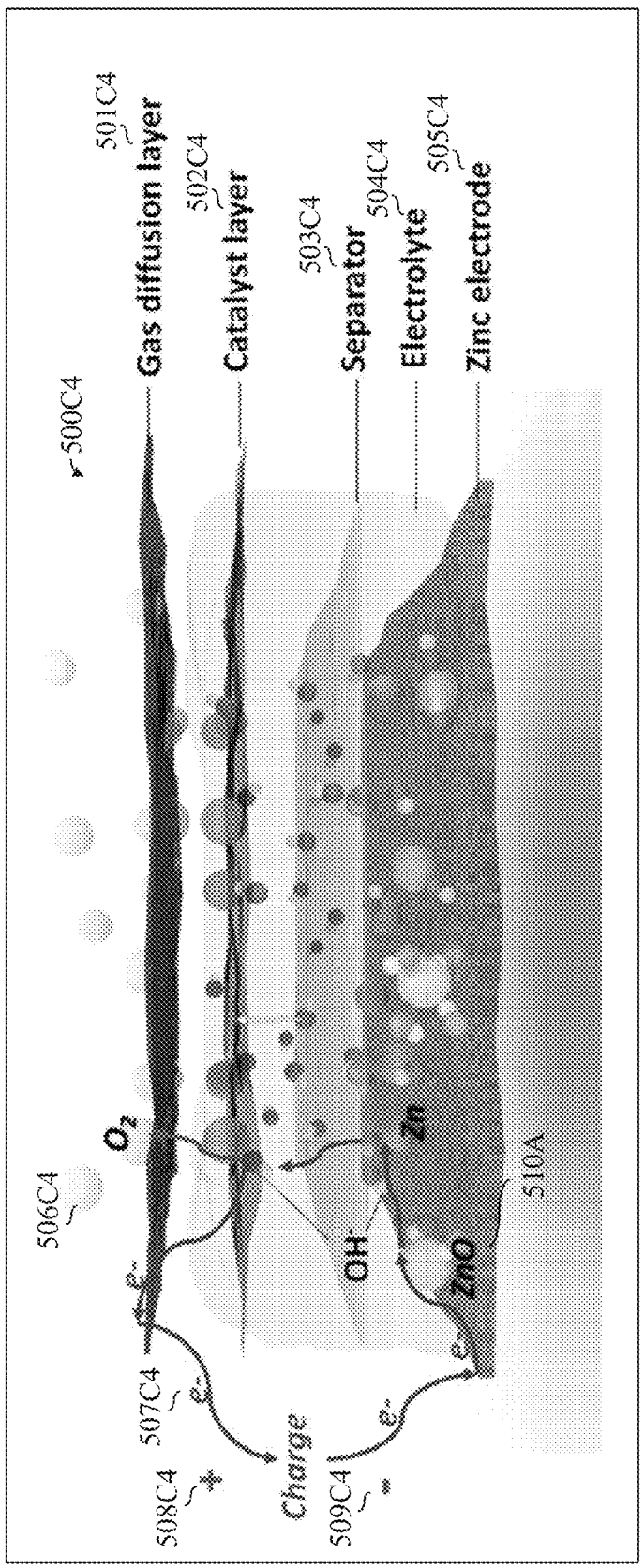
FIG. 5C4
Air (cathode) electrode reaction: $O_2 + 2H_2O^+ + 4e- \rightarrow 4OH^-$, $E = 0.40$ V vs SHE
Metal (anode) electrode reaction: $Mg + 2OH^- \rightarrow MgO + H_2O + 2e-$, $E = -1.26$ V vs SHE
(SHE = Standard Hydrogen Electrode)
FIG. 5C5

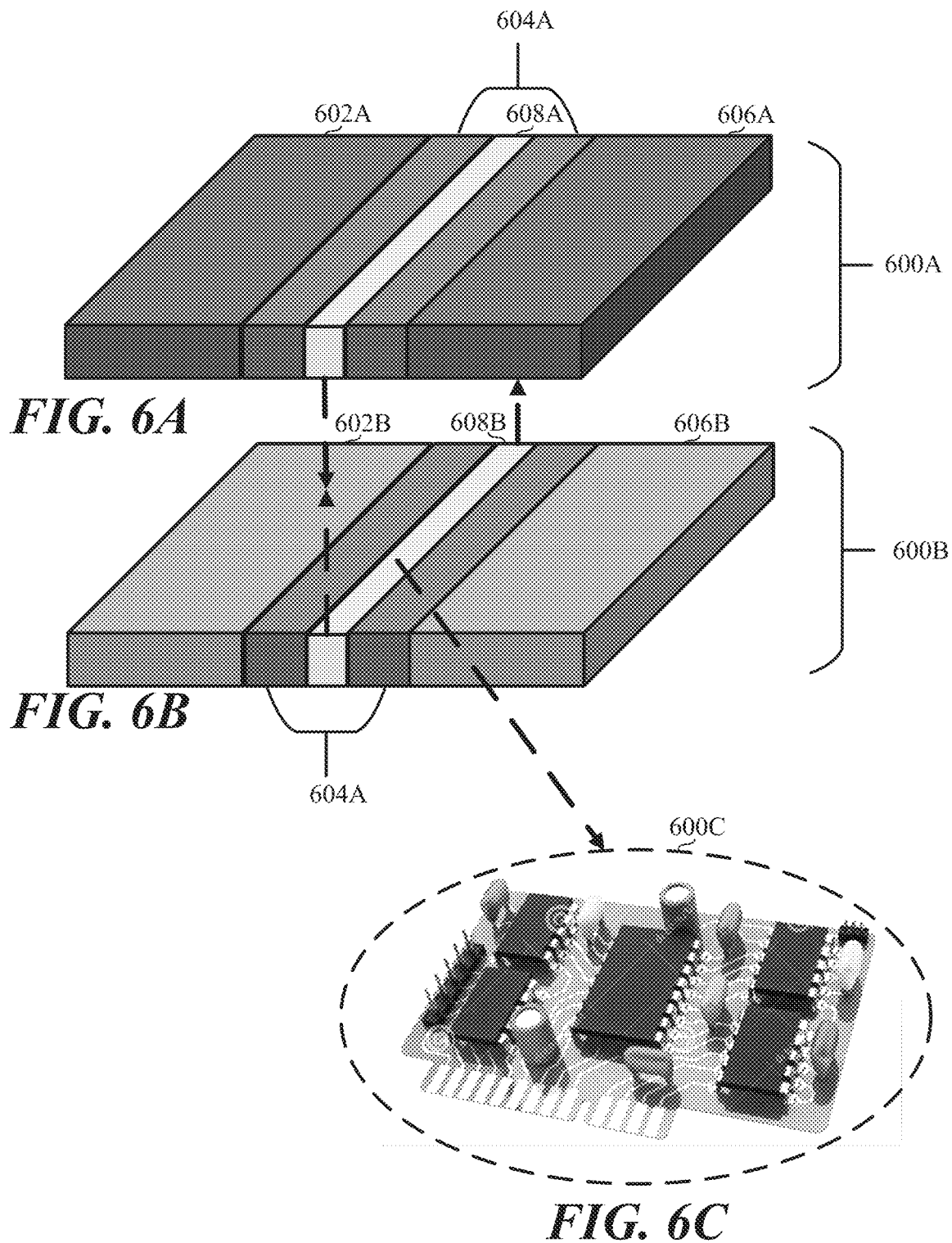

3D Printed Battery Properties 800B

- Creation of hydrophilic and/or hydrophobic layers or patterns to promote activation
- Adhesive electrodes that are conductive, created from active materials

3D Printed Battery Advantages 801B

- Configurable to yield fewer layers to 3D print
- Thin film absorbent separator
- Electrodes are spreadable to cover and gaps in foldable battery structures
- Electrodes may be fabricated under substantially dry condition independent of traditional "wet" battery chemistries
- Electrodes may be carbon-based and/or include zinc, ammonium chloride and/or zinc chloride

*FIG. 8B*

Plasma-Particle Slurry Cast Si Functionalized Si Anode
- *In-situ* functionalized Si anode half cell (2032)
- Fabricate/Test Si anode in Full Cell configuration (Si/LCO pouch)
- Gated energy density/lifetime performance metric (>1000 mAh/g anode @500 cycles)

Plasma-Particle Slurry Cast Functionalized S Cathode in SiSB full cell
- *In-situ* functionalized, lithiated S Cathode half cell (2032)
- Fabricate/Test S cathode in Full cell configuration (Si/S pouch)
- Gated energy density/lifetime performance metric (>500 mAh/g cathode @500 cycles)
- Conditioning/assembly protocol

Limited Production of Particle SiSB
- Productization design/process optimization/application review for scale-up
- System level development (serial/parallel module design, integration, and testing)
- Gated energy density/lifetime performance metric (>350 Wh/kg @ 500 cycles)
- Fabricate/test/optimize limited number of SiSB cells in 18650 cell configuration
- Environmental Test/Validation: Temperature, Shock, Vibration, Humidity

Monolithically integrated, functionalized 'graphene' electrodes
- Establish microwave reactor material-process-property correlations on web coater
- Deposition conditions for conductive 'seed' layer (i.e., current collector)
- Deposition conditions for integrated current collector/electrode film/foil
- Fabricate/Test functionalized 'graphene' Si anode in half cell and full Si/LCO cell configurations
- Fabricate/Test functionalized 'graphene' S cathode in half cell and full Si/lithiated S cell configurations

*FIG. 13*

Batteries and Sensors

- Additional level of information in package tracking and screening; especially at edges
- Edges of the distribution/shipping network represent higher levels of 'touch points' and correspondingly higher costs of ownership
- Reliable, lower cost, autonomous (self-powered, wireless), multi-functional (reconfigurable) Internet-of-Things (IoT) label/tag system for the edges of the distribution system/network
    - Universal, safe, reliable power source across entire network
    - Software definable sensors with low false positives for monitoring controlled (regulated) and uncontrolled ("bad") shipments

*FIG. 15*

*Universal Power Unit*

Energy construct (meta-particle/monolith) across multiple configurations, from:
- Single use, throw away Iot labels (printed),
- Self-contained, portable electronics; *i.e,* TRON/ULD (pouch)
- Transport vehicles; i.e., tugs, delivery vans and trucks
- Aircraft

Safe, reliable, universal energy solution that can be platform/application agnostic
- Drop Box
- Office/Shipping centers
- Delivery Trucks

Secondary (Rechargeable) Solution

A fully *stable*, reversible, 'solid state' ion shuttle process across battery electrodes - *stability* equates to *lifetime, and safety*

Unique Meta-Material: Si-S-C chemistry with lithium ion conduction
- High theoretical material capacities four to five times beyond current state-of-art, lithium oxide chemistries; High rate capability (for charge/discharge)
- No 'elemental' lithium; overcomes weight limitations with respect to Li power supplies in commercial shipments (ground and airborne)
- Stable, 'solid state' interfaces; not self-limited to < 800 cycles as in current SOA Li-ion

Low Unit Cost
- Electrodes (with meta-particles) producible using conventional slurry cast process
- Electrodes monolithically integrated with current collector for reductions in manufacturing cost

Performance: Low cost of ownership
- Scalable, low manufacturing unit cost
- Reliable, long life for low touch of components in the field
- Stability, capacity, and rechargeability of construct in direct alignment with low power management architecture to enable broad utilization in airborne applications

*FIG. 17*

*Ideal Goal:* *Integrated SENsor Tag (INSENT)*

Comprehensive screening protocol at "touch points" at the edges of the shipping network:

- For both regulated substances that are controlled and handled with specific protocols to "bad" substances that are a threat and difficult to control

Low cost (cost of ownership) sensor for detecting vapors from deleterious substances

- Specific selectivity, sensitivity, false positive, and sampling rate/reset requirements
- Low profile form factor compatible with wireless package platform
- Readily and easily integrated into package
- Selective gas detection in the presence of high levels of interference

*FIG. 18*

| Family | Name |
|---|---|
| Metallocenes | Ferrocene |
|  | Cobaltacene |
|  | Ferrocenium |
|  | Cp*2Fe(II) |
| Chelatases | Iron porphine |
|  | Vitamin B12 |
| Coordination compounds | Ru(Bipy)3 |
|  | dicyanobis(ethylenediamine)cadmium(II) |
| Organics | NADH |
|  | Tetracyanoquinodimethane |
|  | Tetramethyl-p-phenyldiamine |
|  | Cyanocobalamin |
|  | Tetrathiafulvalene |
| Polymers | TEMPO |
|  | PTMA |
|  | PVFCN |

*FIG. 22*

MULTI-PART NONTOXIC PRINTED BATTERIES

CROSS-REFERENCE TO RELATED APPLICATIONS

The present application is a continuation application of, and claims priority to, U.S. patent application Ser. No. 16/740,381 entitled "Multi-Part Nontoxic Printed Batteries" and filed on Jan. 10, 2020 (now U.S. Pat. No. 11,555,799 B2), which claims priority to U.S. Provisional Patent Application No. 62/790,932 entitled "Systems for Multi-Part Nontoxic Printed Batteries" and filed on Jan. 10, 2019. The present application also claims priority to U.S. Provisional Patent Application No. 62/894,621 entitled "Systems for Multi-Part Nontoxic Printed Batteries" and filed on Aug. 30, 2019, to U.S. Provisional Patent Application No. 62/926,225 entitled "3D Hierarchical Mesoporous Carbon-Based Particles Integrated into a Continuous Electrode Film Layer" and filed on Oct. 25, 2019, to U.S. Provisional Patent Application No. 62/942,103 entitled "3D Hierarchical Mesoporous Carbon-Based Particles Integrated into a Continuous Electrode Film Layer" and filed on Nov. 30, 2019. The present application is also a Continuation-in-Part of U.S. patent application Ser. No. 16/706,542 entitled "Resonant Gas Sensor" (now U.S. Pat. No. 10,955,378) and filed on Dec. 6, 2019, which is a continuation of U.S. patent application Ser. No. 16/239,423 entitled "Resonant Gas Sensor" (now U.S. Pat. No. 10,502,705) and filed on Jan. 3, 2019, which claims priority to U.S. Provisional Patent Application No. 62/613,716 entitled "Resonant Gas Sensor" and filed on Jan. 4, 2018. All the above-referenced Patent Applications are assigned to the assignee hereof and hereby incorporated by reference in their respective entireties.

TECHNICAL FIELD

This disclosure relates generally to batteries and other electronic and mechanical components that are fabricated by three-dimensional (3D) printing techniques, and more specifically, to a point-of-use battery system that transitions to an activated state from a dormant state based on a folding or peel-back action.

DESCRIPTION OF RELATED ART

Advances in the fields of electronics and telecommunications have enabled consumers to user devices in many new applications. Portable electronic devices and peripherals have already become commonplace, many of which rely on battery-supplied power, and continue to increase in popularity. Filling the electric power consumption demands, batteries-especially rechargeable (also referred to as "secondary") batteries, have emerged as a universal solution, allowing for seemingly indefinite portability and convenient continued device usage.

Nevertheless, challenges related to secondary battery performance regarding lifespan and cyclability have attracted ongoing innovation in lithium-ion (Li-ion) batteries, which use an intercalated Li compound as a formative material at the positive electrode and graphite at the negative electrode. Li-ion batteries, as opposed to other battery types, have been sought for usage in portable electronic devices due to their high energy density, limited to no memory effect (describing how traditional nickel-cadmium and nickel-metal hydride rechargeable batteries lose their ability to store electrical charge over multiple charge-discharge cycles involving partial discharge), and relatively low self-discharge. Thus, Li-ion batteries offer many of the benefits found in primary (non-rechargeable) lithium batteries, including high charge density that results in longer useful lifespans, without the concerns of rapid discharge resulting in overheating, rupture or explosion that may be encountered in Li batteries due to the highly reactive (and potentially explosive and/or combustible) nature of Li metal.

To assist ongoing developments in Li ion battery specific capacity, cycle-ability, and power delivery, amorphous carbon has also been considered (in conjunction with Li) as a formative material for Li ion battery electrodes. Nevertheless, such electrodes continue to suffer from a relatively a low electrical conductivity (high charge transfer resistance), which, in turn, results in a high polarization or internal power loss. Conventional amorphous carbon-based anode materials also may tend to give rise to a high irreversible capacity, among creating other potential issues. Moreover, current Li-intercalated carbon-based electrode compositions or compounds typically include graphene, conductive carbon particles, and binder. In conventional techniques, carbon-based particles are all typically deposited, such as being dropped into existing slurry cast electrodes including current collectors made from metal foil such as copper. Slurry typically is prepared to contain an organic binder or binder material referred to as NMP (N-methyl-2-pyrrolidone).

Studies have shown that fabricating battery electrodes by casting a mixture of active materials, a nonconductive polymer binder, and a conductive additive onto a metal foil current collector can result in electric or ionic bottlenecks, and poor electrical contacts due to randomly distributed conductive phases of carbon-based particles when held together using binders. Such problems are made worse in circumstances where high-capacity electrode materials are employed, where the high stress generated during electro-chemical reactions associated with normal battery usage disrupts mechanical integrity of such binder systems, ultimately resulting in decreased cycle life of batteries. As a result, a need exists for a carbon-based electrode material that addresses the challenges of Li ion batteries regarding usage of binders to impart structural integrity to secondary battery electrodes, and to have other highly desirable features, such as those conducive towards printable batteries suitable for integration with packaging and shipment applications.

SUMMARY

This Summary is provided to introduce in a simplified form a selection of concepts that are further described below in the Detailed Description. This Summary is not intended to identify key features or essential features of the claimed subject matter, nor is it intended to limit the scope of the claimed subject matter. Moreover, the systems, methods and devices of this disclosure each have several innovative aspects, no single one of which is solely responsible for the desirable attributes disclosed herein.

One innovative aspect of the subject matter described in this disclosure can be implemented as a: (1) initially inactive multi-part battery, (2) a point-of-use battery system, and (3) a multi-part battery to power an analyte detector. Such batteries are configured into various implementations to be used in multiple environments and/or for multiple purposes. An initially-inactive battery can include a first current collector having a cathode three-dimensionally (3D) printed thereon, the cathode comprising a first scaffolded mesoporous carbon-based material; a second current collector having an anode 3D printed thereon, the second current collector and the anode positioned substantially opposite to the first current collector and cathode, the anode comprising a second scaffolded mesoporous carbon-based material; and an electrolyte provided in an initial dormant state, the electrolyte infiltrating of pores of the first and second scaffolded carbon-based material to at least partially enhance ionic charge storage therein and to complete an electric circuit between the first and second current collectors, and to transform the initially-inactive battery to an active state upon placement of the cathode substantially proximal to the anode and in absence of directed thermal radiation.

In some implementations, when the electrolyte is in an active state, the battery provides electric current to flow through an electric circuit. The first scaffolded mesoporous carbon-based material and the second scaffolded mesoporous carbon-based material can each further include a plurality of electrically conductive three-dimensional (3D) aggregates of graphene sheets. The aggregates can be sintered together to form an open porous scaffold configured to provide an electrical conduction along and across contact points of the graphene sheets. The open porous scaffold can include a 3D hierarchical structure with mesoscale structuring in combination with fractal-like structuring, wherein the fractal-like structuring is formed based at least in part on a mass or number of primary particles, or based at least in part on a micro, meso, or macro characteristic of a cluster size. The first scaffolded mesoporous carbon-based material and the second scaffolded mesoporous carbon-based material can include a porous arrangement formed in the open porous scaffold and configured to receive electrolyte dispersed therein for ion transport through interconnected pores that define one or more channels. In some cases, each channel of the one or more channels includes: (1) a first portion that provides tunable ion conduits, (2) a second portion that facilitates rapid ion transport, and (3) a third portion that at least partially or temporarily confines active material.

Another innovative aspect of the subject matter described in this disclosure can be implemented as a point-of-use battery system that transitions to an activated state from a dormant state based on a folding or peel-back action, the point-of-use battery system comprising: an anode composed of non-toxic biocompatible metal comprising any one or more of Zn, Mg, or Al and configured to yield a cell voltage of approximately 1.5V-3V, a first printable carbon-based current collector comprising biocompatible multiple few layer graphene (FLG) sheets in electrical contact with the anode and extending therefrom, a 3D hierarchical mesoporous carbon-based cathode having an open porous structure for gas diffusion with areas to catalyze active material reduction comprising oxygen ($O_2$) and other gaseous species, the reduced oxygen creating water upon exposure to ambient air, the open porous structure for active water management.

In some implementations, a polymer-based barrier film is applied over the 3D hierarchical mesoporous carbon-based cathode to prevent oxygen and moisture from entering the open porous structure, the polymer-based barrier film being removable via the peel-back action to permit oxygen to enter the open porous structure. The foregoing point-of-use battery system further includes a second printable carbon-based current collector comprising biocompatible multiple few layer graphene (FLG) sheets in electrical contact with the cathode and extending therefrom, an electrolyte comprising a non-toxic biocompatible aqueous solution independent of organic solvents, the electrolyte activating to conduct ions upon any one or more of the following situations: when an applied pressure causes rupture of electrolyte containing polymeric microspheres such that the rupture releases electrolyte that infiltrates the open porous structure and the anode; or when a hygroscopic compound having solid salts contained within the anode is activated such that the hygroscopic compound extracts moisture to solubilize the solid salts.

In some implementations, the foregoing point-of-use battery system further includes an ion-impregnated cellulose support structure wherein any one or more of the anode or the 3D hierarchical mesoporous carbon-based cathode is 3D printed on opposing sides thereof that activate upon exposure of the ion-impregnated cellulose support structure to O occurring upon the peel-back of the polymer-based barrier films. The point-of-use battery system can be configured such that the anode and the cathode each further include a 3D scaffolded mesoporous carbon-based material. The scaffolded mesoporous carbon-based material further can include a plurality of electrically conductive three-dimensional (3D) aggregates of graphene sheets, the aggregates forming an open porous scaffold that facilitates electrical conduction along contact points of the graphene sheets.

In some implementations, the point-of-use battery is activated by directly or indirectly applying pressure to the anode or by directly or indirectly applying pressure to the cathode, or by directly or indirectly applying pressure to both the anode and the cathode. The battery system can be fabricated by any one or more of 3D printing and/or additive manufacturing techniques. In some situations, the anode and and/or the cathode are 3D printed onto any one or more of a flexible substrate, a semi-rigid substrate, or a rigid substrate, moreover in some situations, the substrate is formed by a portion of a shipping or mailing container. The shipping or mailing container may be formed of card stock, and/or cardboard, and/or paper, and/or polymer-coated paper. The flexible substrate, the semi-rigid substrate, or the rigid substrate can be produced as a label such as a shipping or mailing label.

Another innovative aspect of the subject matter described in this disclosure can be implemented as a multi-part battery system configured to power a sensor having a sensing material with a chemistry additive for detecting an analyte. Some of such implementations include an anode; a cathode; and an electrolyte, wherein activation of the multi-part battery system to power the sensor is accomplished to release the electrolyte between the anode and the cathode in directed absence of thermal radiation. Once released, the electrolyte between the anode and the cathode establishes ionic transport there-between. The sensing material may include a particulate carbon. Any one or more of the anode or the cathode are formed of electrically conductive three-dimensional (3D) aggregates of graphene sheets that form an open porous scaffold to facilitate electrical conduction along contact points of the graphene sheets. The porous arrangement in the open porous scaffold is conducive to receiving the electrolyte dispersed therein for ion transport through interconnected pores, thus providing power to an electrical circuit. The sensor is an impedance sensor that is tuned to respond to presence of an analyte such as nitroglycerine, sarin gas, mustard gas, or cyclone B. The sensor can trigger (such as by either directly or indirectly powering) a beacon if the analyte is any one or more of nitroglycerine, sarin gas, mustard gas, or cyclone B to at least partially assist in location of a container equipped with the multi-part battery system.

In some implementations, one or more of the anode, the cathode, or the electrolyte are substantially non-toxic to assist in biodegradable disposal of the container at least partially. The foregoing multi-part battery system further can include: (1) a flexible substrate; (2) a resonant gas sensor circuit comprising a transducer arranged on the flexible substrate; (3) a sensing material disposed on the flexible substrate and electrically coupled to the transducer, wherein the sensing material includes carbon material in particulate form and a reactive chemistry additive; and (4) an alternating current (AC) source configured to supply AC signals to a first terminal of the transducer, the AC signals comprising a range of frequencies, any one or more of which stimulate the resonant gas sensor. Implementations further include a ground electrode electrically coupled to the transducer and non-ground terminal. The foregoing multi-part battery system can be configured such that the reactive chemistry additive reacts with the analyte to change electrical properties of the sensing material. The sensing material is interrogated by the gas sensor circuit to detect the change in electrical properties due to exposure of the sensing material to the analyte. A carbon material in particulate form is used to enhance sensitivity of the gas sensor circuit when detecting the analyte.

Another innovative aspect of the subject matter described in this disclosure can be implemented as a point-of-use battery system that transitions to an activated state from a dormant state based on a folding or peel-back action. Such a point-of-use battery system includes: (1) active electrode materials for both anode and cathode consisting of printable non-toxic biocompatible polymers, metal oxides/chlorides, metals, or carbon wherein the anode is composed of metal comprising any one or more of Zn, Mg, or Al; (2) a 3D hierarchical mesoporous carbon-based cathode having an open porous structure for gas or liquid ionic diffusion and having areas to catalyze active material reduction comprising oxygen ($O_2$) and water ($H_2O$) that is actively managed from ambient air or from amounts of $MnO_2$ or AgO that is loaded onto a carbon host structure; and (3) a carbon cellulose nanofibril film that serves as a non-toxic, biocompatible/bioresorbable electrolyte and that serves as a separator between electrodes.

Details of one or more implementations of the subject matter described in this disclosure are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Implementations of the subject matter disclosed herein are illustrated by way of example and are not intended to be limited by the figures of the accompanying drawings. Like numbers reference like elements throughout the drawings and specification. Note that the relative dimensions of the following figures may not be drawn to scale.

FIGS. 1A-1B show an exploded view of layers of a printed battery, such layers including elements of a cathode and anode portion, respectively.

FIGS. 1C1-1C2 show folding techniques related to activating aspects of the printed battery shown in FIGS. 1A-1B.

FIGS. 1D1-1D3 show example printed battery features.

FIG. 2 shows an example schematic for a traditional Li ion battery incorporating the presently disclosed 3D self-assembled binder-less mesoporous carbon-based particles.

FIGS. 3A-3F show illustrative schematic representations, at various magnification levels, and/or micrographs of a 3D self-assembled binder-less 3D mesoporous carbon-based particle having tunable electrical pathways and ionic conduits throughout the thickness thereof.

FIGS. 5C1-5C3 show examples related to a printed battery featuring pressure-based electrolyte release capabilities.

FIGS. 5C4-5C5 shows an example of metal-air battery chemistry including an air (cathode) electrode reaction and a metal (anode) electrode reaction.

FIG. 6A-6C shows views of a printed battery that can be activated at a point-of-use.

FIGS. 7A-8A show self-aligning geometry that self-aligns even in presence of lateral misregistration.

FIG. 8B shows an example listing of printed battery properties and advantages.

FIGS. 12C-18 show information, targets, properties, and related materials for printed batteries according to a variety of examples of the presently disclosed implementations.

FIG. 22 is a table that lists examples of possible redox mediators that may be used, in accordance with some implementations.

Figure 1E:
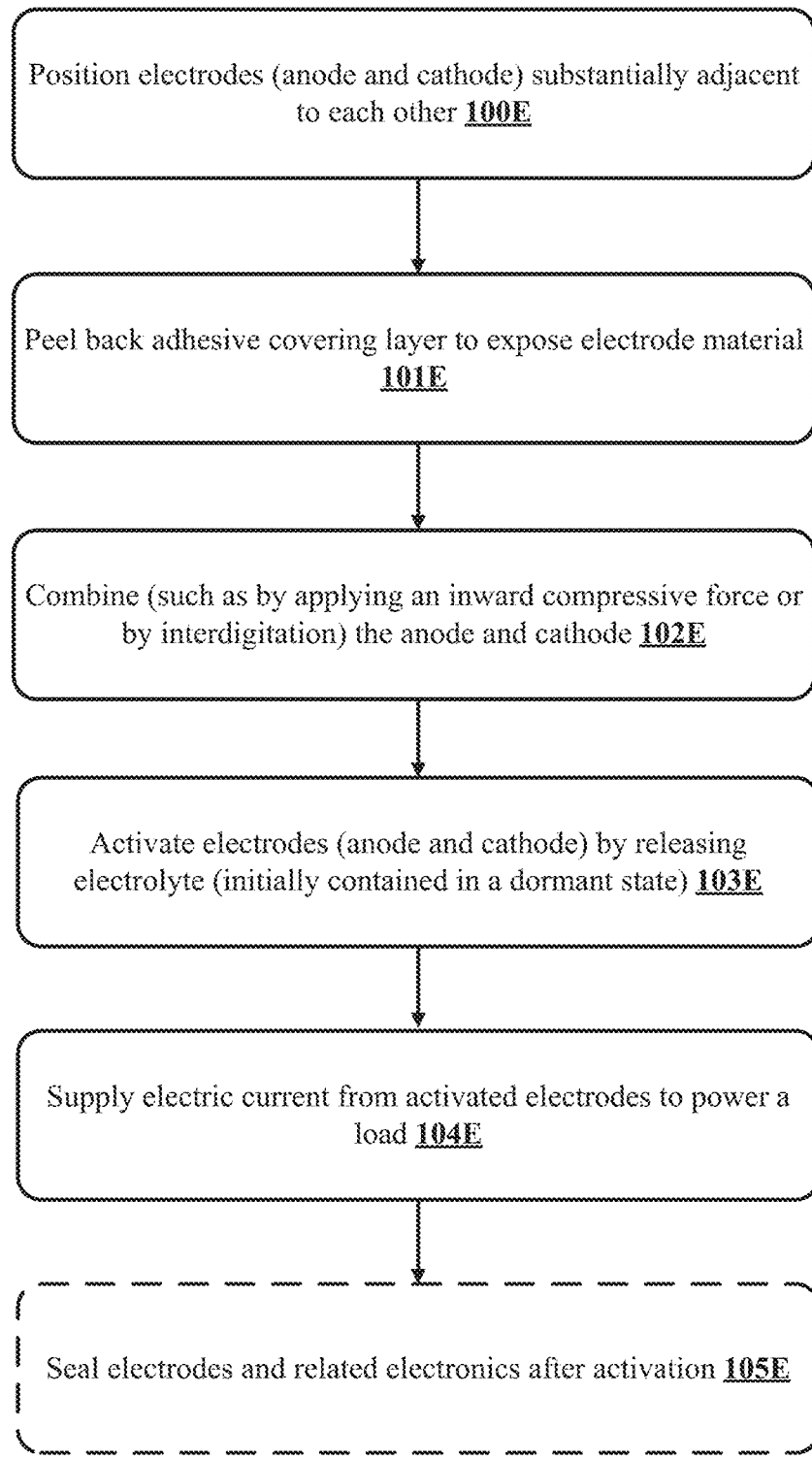
FIG. 1E shows a flowchart related to a method for activating an example printed battery.

To facilitate understanding, identical reference numerals have been used, where possible, to designate identical elements that are common to the figures. It is contemplated that elements disclosed may be beneficially utilized on other elements without specific recitation. The drawings referred to here should not be understood as being drawn to scale unless specifically noted. Also, the drawings are often simplified, and details or components omitted for clarity of presentation and explanation. The drawings and discussion explain principles discussed below, where like designations denote like elements.

DETAILED DESCRIPTION

Various aspects of the novel systems, apparatuses, and methods are described more fully herein with reference to the accompanying drawings. The teachings disclosed can, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art.

Based on the teachings herein one skilled in the art should appreciate that the scope of the disclosure is intended to cover any aspect of the novel systems, apparatuses, and methods disclosed herein, whether implemented independently of or combined with any other aspect of the invention. For example, an apparatus can be implemented, or a method can be practiced using any number of the aspects set forth herein. In addition, the scope of the invention is intended to cover such an apparatus or method which is practiced using other structure, functionality, or structure and functionality in addition to or other than the various aspects of the invention set forth herein. Any aspect disclosed herein can be embodied by one or more elements of a claim.

Although some examples and aspects are described herein, many variations and permutations of these examples fall within the scope of the disclosure. Although some benefits and advantages of the preferred aspects are mentioned, the scope of the disclosure is not intended to be limited to benefits, uses, or objectives. Rather, aspects of the disclosure are intended to be broadly applicable to a point-of-use battery system that transitions to an activated state from a dormant state based on a folding or peel-back action, the point-of-use battery system incorporating a 3D self-assembled multi-modal mesoporous carbon-based particle composed of electrically conductive three-dimensional (3D) aggregates of graphene sheets, some of which are illustrated in the figures and in the following description of the preferred aspects. The detailed description and drawings are merely illustrative of the disclosure rather than limiting, the scope of the disclosure being defined by the appended claims and equivalents thereof.

Definitions

Li-Ion Batteries

A Li-ion battery is a type of secondary (rechargeable) battery. Li-ion battery technology has become very important in recent years as these batteries show great promise as power sources that can lead to an electric vehicle (EV) revolution (referring to widespread implementation of EVs across numerous applications). The development of new materials (for Li-ion batteries) is the focus of research in the field of materials science, as Li-ion batteries are considered to be the most impressive success story of modern electrochemistry. Li-ion batteries power most modern portable devices and seem to have overcome psychological barriers of the consuming public against the use of such high energy density devices on a larger scale for more demanding applications, such as EV.

Regarding operation, in Li-ion batteries, Li ions (Li+) migrate from the negative electrode through an electrolyte to the positive electrode during discharge and return when charging. Li-ion batteries traditionally use an intercalated Li compound as a formative material at the positive electrode and graphite at the negative electrode. The batteries have a high energy density, no "memory-effect" (describing the situation in which nickel-cadmium batteries gradually lose their maximum energy capacity if they are repeatedly recharged after being only partially discharged) and low self-discharge. However, unlike conventional battery chemistries, Li ion batteries can (due to the highly reactive nature of elemental and ionic Li) present a safety hazard. Under certain conditions, since Li ion batteries can contain a flammable electrolyte, if they are punctured, hit, otherwise damaged or even incorrectly (excessively) charged, Li batteries can deteriorate unexpectedly, including through explosions and fires. Nevertheless, the high energy density of Li ion batteries permits for longer usable lifespans of several hours between charging cycles, and longer cycle life, referring to the electric current delivery or output performance of a given Li-ion battery over multiple repeat charge-discharge (partial or total charge depletion) cycles.

Li metal, due to its high theoretical specific capacity of 3,860 mAh/g, low density (0.59 g cm-3) and low negative electrochemical potential (−3.040 V compared to a standard hydrogen electrode), appears as an ideal material for the negative electrode of secondary Li-ion batteries. However, unavoidable and uncontrollable dendrite growth, referring the growth of a branching tree-like structure within the battery itself, caused by Li precipitates can cause serious safety concerns related to short-circuits, and limited Coulombic efficiency, referring to the charge efficiency by which electrons are transferred in batteries, during deposition and stripping operations inherent in Li-ion batteries. Such challenges have previously impeded Li ion battery applications.

However, concerns related to safety of earlier-developed Li secondary batteries led to the creation and refinement of newer generation Li-ion secondary batteries. Such Li-ion batteries typically feature carbonaceous materials used as an anode, such carbonaceous anode materials including: (1) graphite; (2) amorphous carbon; and (3) graphitized carbon. The first type of the three carbonaceous materials presented above includes naturally occurring graphite and synthetic graphite (or artificial graphite, such as Highly Oriented Pyrolytic Graphite, HOPG). Either form of graphite can be intercalated with Li. The resulting Graphite Intercalation Compound (GIC) may be expressed as $Li_xC_6$, where X is typically less than 1. To limit (minimize) the loss in energy density due to the replacement of Li metal with the GIC, X in $Li_xC_6$ must be maximized and the irreversible capacity loss ($Q_{ir}$), in the first charge of the battery must be minimized.

The maximum amount of Li that can be reversibly intercalated into the interstices between graphene planes of a perfect graphite crystal is believed to occur in a graphite intercalation compound represented by $Li_xC_6$ (x=1), corresponding to a theoretical 372 mAh/g. However, such a limited specific capacity (of the discussed theoretical 372 mAh/g) cannot satisfy the demanding requirements of the higher energy-density power needs of modern electronics and EVs.

Carbon-based anodes, such as (1) graphite intercalated with Li as discussed above, can demonstrate extended cycle lifespans due to the presence of a surface-electrolyte interface layer (SEI), which results from the reaction between Li and surrounding electrolyte (or between Li and the anode surface/edge atoms or functional groups) during the initial several charge-discharge cycles. Li ions consumed in this reaction (referring to the formation of the SEI) may be derived from some of the Li ions originally intended for the charge transfer purpose (referring to the dissociation of elemental Li when intercalated with carbon in a carbon-based structure, such as the anode, during Li ion movement in electrolyte across a porous separator to the cathode as related to electron release and flow to power a load during Li ion battery discharge cycles. As the SEI is formed, the Li ions become part of the inert SEI layer and become "irreversible", in that they can no longer be an active element (or ion) used for charge transfer. As a result, it is desirable to minimize the amount of Li used for the formation of an effective SEI layer. In addition to SEI formation, $Q_{ir}$, has been attributed to graphite exfoliation caused by electrolyte/solvent co-intercalation and other side reactions.

Referring anode carbonaceous material introduced earlier, (2) amorphous carbon, contains no (or very little) micro- or nano-crystallites. Amorphous carbon includes both so-called "soft carbon" and "hard carbon". Soft carbon refers to a carbon material that can be graphitized at a temperature of about 2,500° C. or higher. In contrast, hard carbon refers to a carbon material that cannot be graphitized at a temperature higher than 2,500° C.

However, in practice and industry, the so-called "amorphous carbons" commonly used as anode active materials may not be purely amorphous, but rather contain some minute amount of micro- or nano-crystallites, each crystallite being defined as a small number of graphene sheets (oriented as basal planes) that are stacked and bonded together by weak van der Waals forces. The number of graphene sheets can vary between one and several hundreds, giving rise to a c-directional dimension (thickness $L_e$) of typically 0.34 nm to 100 nm. The length or width ($L_a$) of these crystallites is typically between tens of nanometers to microns.

Among this class of carbon materials, soft and hard carbons can be produced by low-temperature pyrolysis (550-1,000° C.) and exhibit a reversible specific capacity of 400-800 mAh/g in the 0-2.5 V range. A so-called "house-of-cards" carbonaceous material has been produced with enhanced specific capacities approaching 700 mAh/g.

Research groups have obtained enhanced specific capacities of up to 700 mAh/g by milling graphite, coke, or carbon fibers and have elucidated the origin of the additional specific capacity with the assumption that in disordered carbon containing some dispersed graphene sheets (referred to as "house-of-cards" materials), Li ions are adsorbed on two sides of a single graphene sheet. It has been also proposed that Li readily bonds to a proton-passivated carbon, resulting in a series of edge-oriented Li—C—H bonds. This provides an additional source of Li+ in some disordered carbons. Other research suggested the formation of Li metal monolayers on the outer graphene sheets of graphite nano-crystallites. The discussed amorphous carbons were prepared by pyrolyzing epoxy resins and may be more correctly referred to as polymeric carbons. Polymeric carbon-based anode materials have also been studied.

Chemistry, performance, cost, and safety characteristics may vary across Li ion battery variants. Handheld electronics may use Li polymer batteries (with a polymer gel as electrolyte) with Li cobalt oxide ($LiCoO_2$) as cathode material, which offers high energy density but may present safety risks, especially when damaged. Li iron phosphate ($LiFePO_4$), Li ion manganese oxide battery ($LiMn_2O_4$, $Li_2MnO_3$, or LMO), and Li nickel manganese cobalt oxide ($LiNiMnCoO_2$ or NMC) may offer lower energy density but provide longer useful lives and less likelihood of fire or explosion. Such batteries are widely used for electric tools, medical equipment, and other roles. NMC in particular is often considered for automotive applications.

Electrical Conductance of Carbon-Based Materials

Advances in high conductance carbon materials such as carbon nanotubes (CNT), graphene, amorphous carbon, and/or crystalline graphite in electronics allows for the printing of these materials onto many types of surfaces without necessarily using printed circuit boards, and/or without the use of materials or compounds that have been identified as being toxic to humans. Usage of high conductance carbon as a feedstock material and/or other material during any one or more of the additive manufacturing processes described above may facilitate the fabrication of batteries (including Li ion batteries) with micro-lattice structures suitable for enhanced functionality, electric power storage and delivery, and optimal efficiency. Moreover, although many of the devices described may serve as power sources (batteries, capacitors), those of skill in the art will appreciate that such 3D printing technologies may be reconfigured using high conductance carbon materials such as carbon nanotubes (CNT), graphene, amorphous carbon, or crystalline graphite can form other electronic devices.

Printing technologies using high conductance carbon materials such as carbon nanotubes (CNT), graphene, amorphous carbon, or crystalline graphite may be implemented and/or otherwise incorporated in the fabrication of the following devices: antennas (tuned antennas), sensors (bio sensors), energy harvesters (photocells), and other electronic devices.

Graphene

Graphene is an allotrope of carbon in the form of a single layer of atoms in a two-dimensional hexagonal lattice in which one atom forms each vertex. It is the basic structural element of other allotropes, including graphite, charcoal, carbon nanotubes and fullerenes. It can also be considered as an indefinitely large aromatic molecule, the ultimate case of the family of flat polycyclic aromatic hydrocarbons.

Graphene has a special set of properties which set it apart from other elements. In proportion to its thickness, it is about 100 times stronger than the strongest steel. Yet its density is dramatically lower than any other steel, with a surface (surface-related) mass of 0.763 mg per square meter. It conducts heat and electricity very efficiently and is transparent. Graphene also shows a large and nonlinear diamagnetism, even greater than graphite and can be levitated by Nd—Fe—B magnets. Researchers have identified the bipolar transistor effect, ballistic transport of charges and large quantum oscillations in the material. Its end-use application areas are widespread, finding unique implementations in advanced materials and composites, as well as being used as a formative material to construct ornate scaffolds usable in Li ion battery electrodes to enhance ion transport and electric current conduction to yield specific capacity and power delivery figures not otherwise attainable by conventional battery technologies.

Chemical Functionalization of Graphene

Functionalization, as generally understood and as referred to herein, implies the process of adding new functions, features, capabilities, or properties to a material or substance by altering the surface chemistry of the material. Functionalization is a fundamental technique used throughout chemistry, materials science, biological engineering, textile engineering, and nanotechnology and may be performed by attaching molecules or nanoparticles to the surface of a material, with a chemical bond or through adsorption, the adhesion of atoms, ions or molecules from a gas, liquid or dissolved solid to a surface to create a film of the adsorbate on the surface of the adsorbent without forming a covalent or ionic bond thereto.

Functionalization and dispersion of graphene sheets may be of critical importance to their respective end-use applications. Chemical functionalization of graphene enables the material to be processed by solvent-assisted techniques, such as layer-by-layer assembly, spin-coating, and filtration and also prevents the agglomeration of single layer graphene (SLG) during reduction and maintains the inherent properties of graphene.

Currently, the functionalization of graphene may be performed by covalent and noncovalent modification techniques. In both instances, surface modification of graphene oxide followed by reduction has been carried out to obtain functionalized graphene. It has been found that both the covalent and noncovalent modification techniques are very effective in the preparation of processable graphene.

However, electrical conductivity of functionalized graphene has been observed to decrease significantly compared to pure graphene. Moreover, the surface area of the functionalized graphene prepared by covalent and non-covalent techniques decrease significantly due to the destructive chemical oxidation of flake graphite followed by sonication, functionalization, and chemical reduction. To overcome these problems, studies have been reported on the preparation of functionalized graphene directly from graphite (one-step process). In all these cases, surface modification of graphene can prevent agglomeration and facilitates the formation of stable dispersions. Surface modified graphene can be used for the fabrication of polymer nanocomposites, Li ion battery electrodes, super-capacitor devices, drug delivery system, solar cells, memory devices, transistor device, biosensor, etc.

Graphite

Graphite, as commonly understood and as referred to herein, implies a crystalline form of elemental carbon with atoms arranged in a hexagonal structure. Graphite occurs naturally in this form and is the most stable form of carbon under standard (atmospheric) conditions. Otherwise, under high pressures and temperatures, graphite converts to diamond. Graphite is used in pencils and lubricants. Its high conductivity makes it useful in electronic products such as electrodes, batteries, and solar panels.

Roll-to-Roll (R2R) Processing

R2R processing refers to the process of creating electronic devices on a roll of flexible plastic or metal foil. R2R processing may also refer to any process of applying coatings, printing, or performing other processes starting with a roll of a flexible material and re-reeling after the process to create an output roll. These processes, and others such as sheeting, may be grouped together under the general term "converting". When the rolls of material have been coated, laminated or printed they can be subsequently cut and/or slit to their finished size on a slitter rewinder.

R2R processing of large-area electronic devices may reduce manufacturing cost. Other applications could arise which take advantage of the flexible nature of the substrates, such as electronics embedded into clothing, 3D-printed Li ion batteries, large-area flexible displays, and roll-up portable displays.

3D Printing—Generally 3D printing or Additive Manufacturing has found applications in various manufacturing, medical, industry and sociocultural sectors, which in turn have generated enough interest to further facilitate research and development. Also, 3D printing has been used in humanitarian applications to produce a range of medical items, including prosthetics, spares, and repairs.

Earlier additive manufacturing applications concentrated on the toolroom end of the manufacturing spectrum, where, rapid prototyping was one of the earliest additive variants, and its mission was to reduce the lead time and cost of developing prototypes of new parts and devices, which was earlier only done with subtractive toolroom methods such as CNC milling, turning, and precision grinding. More recently, additive manufacturing has entered production to a much greater extent.

Additive manufacturing techniques are adaptable and may be configured for an innumerable amount of end-use applications, including, by way of example, but not limitation thereto, food, such as by squeezing out food, layer by layer, into three-dimensional objects. A large variety of foods may be appropriate candidates, such as chocolate and candy, and flat foods such as crackers, pasta, and pizza. Moreover, sources indicate that NASA is looking into the technology in order to create 3D printed food to limit food waste and to make food that are designed to fit an astronaut's dietary needs.

Moreover, 3D printing has also entered clothing, with fashion designers experimenting with 3D-printed shoes and dresses. In commercial production Nike® is using 3D printing to prototype and manufacture the 2012 Vapor Laser Talon football shoe for players of American football, and New Balance is 3D manufacturing custom-fit shoes for athletes. 3D printing has even progressed to a level where companies are printing consumer-grade eyewear with on-demand custom fit and styling (although they cannot print the lenses). On-demand customization of glasses is possible with rapid prototyping.

3D Printing—Advanced Batteries

Applications of 3D printing related manufacturing techniques also extend to the manufacture of porous electrodes for lithium-ion batteries, which were restricted earlier due to limitations in the design of 3D printed electrodes to just a few possible architectures. Until recently, the internal geometry that produced the best porous electrodes through additive manufacturing required an interdigitated configuration where metal prongs are interlocked, such as like the fingers or "digits" of two clasped hands, with the lithium shuttling between the two sides.

Lithium-ion battery capacity may be significantly improved upon, at a microscale level, if such batteries are produced with electrodes that have pores and channels. And, although previously often used, an interdigitated geometry allows for lithium to transport through the battery efficiently during charging and discharging, but may not always be optimal depending on intended end-uses, etc.

Accordingly, researchers have developed a new methods of 3D printing battery electrodes that creates 3D micro-lattice structures with controlled porosity, where 3D printing of such micro-lattice structures has shown substantial improvement in the capacity and charge-discharge rates for lithium-ion batteries.

For lithium-ion batteries, electrodes with porous architectures can lead to higher charge capacities since such architectures or configurations allow lithium to penetrate through the electrode volume leading to very high electrode utilization, and thus higher energy storage capacity. Compared to conventional batteries, where 30-50% of the total electrode volume is unutilized, battery electrodes manufactured by 3D printing create a micro-lattice electrode architecture that allows for the efficient transport of lithium through the entire electrode, which also increases battery charging rates.

Developments in additive manufacturing methods likewise translate into corresponding advances in capabilities regarding the printing of complex geometries for 3D battery architectures, as well as important steps toward geometrically optimizing 3D configurations for electrochemical energy storage, access, and delivery to devices.

Specific 3D-printed micro-lattice structures used as electrodes in lithium-ion batteries have been shown to improve battery performance in several ways, including, but not limited to: a fourfold increase in specific capacity and a twofold increase in areal capacity when compared to a solid block electrode, such as may be related to surface area to volume ratios of such 3D printed micro-lattice structures. Further, 3D printed electrodes have been shown to retain their complex 3D lattice structures after many, such as forty, electrochemical cycles thus demonstrating their mechanical robustness and ongoing reliability. Thus, such 3D printed batteries with specific microstructures can have relatively high electrical charge storage capacity for the same weight or alternately, for the same capacity, a greatly reduced weight, such as by offering optimal surface area to volume ratios and configurations, which may be an important attribute for certain applications requiring enumerated parameters, such as transportation and medical device applications, including implantable devices beneath the skin.

Until recently, 3D printed battery efforts were limited to extrusion-based printing, such as referring to a process used to create objects of a fixed cross-sectional profile where material is pushed through a die of the desired cross-section. In applications to print complex micro-lattice structures, a wire of material may be extruded from a nozzle to create continuous structures. Also, interdigitated structures are possible using this method as is the 3D printing of battery electrodes by rapidly assembling individual droplets one-by-one into 3D structures such that resulting structures have complex geometries that would be otherwise impossible to fabricate using typical or traditional extrusion methods.

Moreover, since droplets of material used for 3D printing are separated from each other, the creation of complex geometries is possible, as opposed to traditional extrusion printing, which requires a single stream of material.

The ability to create sophisticated and intricate 3D structures by 3D printing may be of particular importance in the fields of consumer electronics, the medical devices industry, as well as aerospace applications. Related research may also integrate well with biomedical electronic devices, where miniaturized batteries are often required. Non-biological electronic micro-devices may also benefit from developments in 3D printing of battery microstructures. On a larger scale, electronic devices, small drones, and aerospace applications themselves may also benefit from and use 3D printing technology as well, due to the low weight and high capacity of the batteries printed using this method.

Oxidation-Reduction (Redox) Reactions

Redox are a type of chemical reaction in which the oxidation states of atoms are changed. Redox reactions are characterized by the transfer of electrons between chemical species, most often with one species, such as the reducing agent, undergoing oxidation, losing electrons, while another species, the oxidizing agent, undergoes reduction, gains electrons. The chemical species from which the electron is stripped is said to have been oxidized, while the chemical species to which the electron is added is said to have been reduced.

Intercalation

As commonly understood and as referred to herein, in chemistry, intercalation is the reversible inclusion or insertion of a molecule (or ion) into materials with layered structures. Examples are found in graphite, graphene, and transition metal dichalcogenides.

Li Intercalation into Bi- or Multi-Layer Graphene

Electrical storage capacity of graphene and the Li-storage process in graphite currently present challenges requiring further development in the field of Li ion batteries. Efforts have therefore been undertaken to further develop three-dimensional bi-layer graphene foam with few defects and a predominant Bernal stacking configuration, a type of bilayer graphene where half of the atoms lie directly over the center of a hexagon in the lower graphene sheet, and half of the atoms lie over an atom, and to investigate its Li-storage capacity, process, kinetics, and resistances. Li atoms may be stored only in the graphene interlayer. Further, various physiochemical characterizations of the staged Li bilayer graphene products further reveal the regular Li-intercalation phenomena and illustrate this Li storage pattern of two-dimensions.

Electrochemical Capacitors (ECs)

Electrochemical capacitors (ECs), also referred to as "ultracapacitors" and/or "supercapacitors", are considered for uses in hybrid or full EVs. ECs can supplement (or in certain uses replace) traditional batteries, including high-performance Li ion batteries, used in an EVs to provide short bursts of power (forward propulsion) often needed for rapid acceleration. Traditional batteries may still be used provide uniform power for cruising at normal highway speeds, but supercapacitors (with their ability to release energy much more quickly than batteries) may activate and supplement battery-provided power at times when the car needs to accelerate, such as for merging, passing, emergency manoeuvres, and hill climbing.

ECs must also store sufficient energy to provide an acceptable driving range, such as from 220-325 miles or more. And to be cost- and weight-effective compared to additional battery capacity, ECs must combine adequate specific energy and specific power with long cycle life and meet cost targets as well. Specifically, ECs for application in EVs must store about 400 Wh of energy, be able to deliver about 40 kW of power for about 10 seconds and provide high cycle-life (>100,000 cycles).

The high volumetric capacitance density of an EC (10 to 100 times greater than conventional capacitors) derives from using porous electrodes, which may incorporate, feature, and/or be constructed from scaffolded graphene-based materials, to create a large effective "plate area" and from storing energy in the diffuse double layer. This double layer, created naturally at a solid-electrolyte interface when voltage is imposed, has a thickness of only about 1-2 nm, therefore forming an extremely small effective "plate separation." In some ECs, stored energy is further augmented by pseudo-capacitance effects, occurring again at the solid-electrolyte interface due to electrochemical phenomena such as the redox charge transfer. The double layer capacitor is based on a high surface area electrode material, such as activated carbon, immersed in an electrolyte. A polarized double layer is formed at electrode-electrolyte interfaces providing high capacitance.

Overview

Introduction

Advances in modern carbon-based materials(graphene) have enhanced applications using such materials, such as in secondary batteries. Electrochemical Li intercalation or de-intercalation properties of carbon and carbon-based materials depend significantly on their respective morphology, crystallinity, orientation of crystallites, and defects as well. Further, the electric storage capacity of a Li-ion battery can be enhanced by the selection and integration of desirable nano-structured carbon materials such as carbon in certain allotropes such as graphite and graphene, or nano-sized graphite, nanofibers, isolated single walled carbon nanotubes, nano-balls, and nano-sized amorphous carbon, having small carbon nanostructures in which no dimension is greater than about 2 μm.

For example, known methods for fabricating carbon and Li-ion electrodes for rechargeable Li cells include steps for forming a carbon electrode composed of graphitic carbon particles adhered by an ethylene propylene diene monomer binder used to achieve a carbon electrode capable of subsequent intercalation by Li-ions. The carbon electrode is reacted with Li-ions to incorporate Li-ions into graphitic carbon particles of the electrode. An electrical current is repeatedly applied to the carbon electrode to initially cause a surface reaction between the Li-ions and to the carbon and subsequently cause intercalation of the Li-ions into crystalline layers of the graphitic carbon particles. With repeated application of the electrical current, intercalation is achieved to near a theoretical maximum.

Other exfoliated graphite-based hybrid material compositions relate to: (a) micron- or nanometer-scaled particles or coating which are capable of absorbing and desorbing alkali or alkaline metal ions (particularly, Li ions); and (b) exfoliated graphite flakes that are interconnected to form a porous, conductive graphite network comprising pores. The particles or coating resides in a pore of the network or is attached to a flake of the network. The exfoliated graphite amount is in the range of 5% to 90% by weight and the number of particles or amount of coating is in the range of 95% to 10% by weight.

Also, high-capacity silicon-based anode active materials have been shown to be effective in combination with high-capacity Li rich cathode active materials. Supplemental Li can improve the cycling performance and reduce irreversible capacity loss for some silicon based active materials. Silicon based active materials can be formed in composites with electrically conductive coatings, such as pyrolytic carbon coatings or metal coatings, and composites can also be formed with other electrically conductive carbon components, such as carbon nano fibers and carbon nanoparticles.

And, known rechargeable batteries of an alkali metal having an organic electrolyte experiences little capacity loss upon intercalation of the carbonaceous electrode with the alkali metal. The carbonaceous electrode may include a multi-phase composition including both highly graphitized and less graphitized phases or may include a single phase, highly graphitized composition subjected to intercalation of Li at above about 50° C. Incorporation of an electrically conductive filamentary material such as carbon black intimately interspersed with the carbonaceous composition minimizes capacity loss upon repeated cycling.

Otherwise, a known Li based negative electrode material is characterized by comprising 1 $m^2/g$ or more of carbonaceous negative electrode active material specific surface area, a styrene-butadiene rubber binder, and a fiber diameter formed to 1,000 nanometers of carbon fiber. Such negative electrode materials are used for Li batteries, which have desirable characteristics, such as a low electrode resistance, high strength of the electrode, an electrolytic solution having excellent permeability, high energy density and a high-rate charge/discharge. The negative electrode material contains 0.05 to 20 mass % of carbon fibers and a styrene at 0.1 to 6.0% by mass. Butadiene rubber forms the binder and may further contain 0.3 to 3% by mass thickener, such as carboxymethyl methylcellulose.

Still further, existing technologies relate to a battery that has an anode active material that has been: (1) pre-lithiated; and (2) pre-pulverized. This anode may be prepared with a method that comprises: (a) providing an anode active material; (b) intercalating or absorbing a desired amount of Li into the anode active material to produce a pre-lithiated anode active material; (c) comminating, referring to the reduction of solid materials from one average particle size to a smaller average particle size, by crushing, grinding, cutting, vibrating, or other processes, the pre-lithiated anode active material into fine particles with an average size less than 10 μm (preferably <1 μm and most preferably <200 nm); and, (d) combining multiple fine particles of the pre-lithiated anode active material with a conductive additive and/or a binder material to form the anode. The pre-lithiated particles are protected by a Li ion-conducting matrix or coating material. The matrix material is reinforced with nano graphene platelets.

Graphitic nanofibers have also been disclosed and include tubular fullerenes (commonly called "buckytubes"), nano tubes and fibrils, which are functionalized by chemical substitution, are used as electrodes in electrochemical capacitors. The graphitic nanofiber-based electrode increases the performance of the electrochemical capacitors. Preferred nanofibers have a surface area greater than about 200 m²/gm and are substantially free of micropores.

And, known high surface area carbon nanofibers have an outer surface on which a porous high surface area layer is formed. Methods of making the high surface area carbon nanofiber include pyrolyzing a polymeric coating substance provided on the outer surface of the carbon nanofiber at a temperature below the temperature at which the polymeric coating substance melts. The polymeric coating substance used as the high surface area around the carbon nanofiber may include phenolics such as formaldehyde, polyacrylonitrile, styrene, divinyl benzene, cellulosic polymers and cyclotrimerized diethynyl benzene. The high surface area polymer which covers the carbon nanofiber may be functionalized with one or more functional groups.

System Structure
Point-of-Use Battery System

FIGS. 1A-1B show an exploded view of layers of a printed battery, such layers including elements of a cathode and anode portion, respectively. Such a stacked (such as "sandwiched") architecture of a battery 100B (shown implemented in package 300A) as shown here includes elements of a cathode portion and an anode portion. The cathode portion may include an electrolyte layer 140B and a cathode 106B in a vertically stacked and adjacent configuration shown adhered to substrate 108B by seal 107B. Likewise, similar to cathode portion 111B, anode portion 110B may also include substrate 101B adhered to anode 104B via seal 103B.

Each the anode and cathode portions may include collectors 102B, 109B that are 3D printed substrates 101B, 108B, respectively. In the implementation shown in FIGS. 1A-1B, electrolyte layer 105B is shown as being included on the cathode portion, although in other implementations the electrolyte may be incorporated within the cathode 106B. Each electrode, such as anode 104B and cathode 106B, is shown in FIGS. 1A-1B as being a layer positioned between current collectors 102B, 109B, respectively and the electrolyte layer 105B. Seals 103B, 107B can define perimeters (described in further detail below) that constrain spreading of electrolyte 105B and/or electrode materials when the battery is activated. Printed substrate surrounding battery 100B may serve as seals 103B, 107B, while in other implementations seals 303B, 107B may be formed from another substance deposited onto the substrate.

Figure 2:
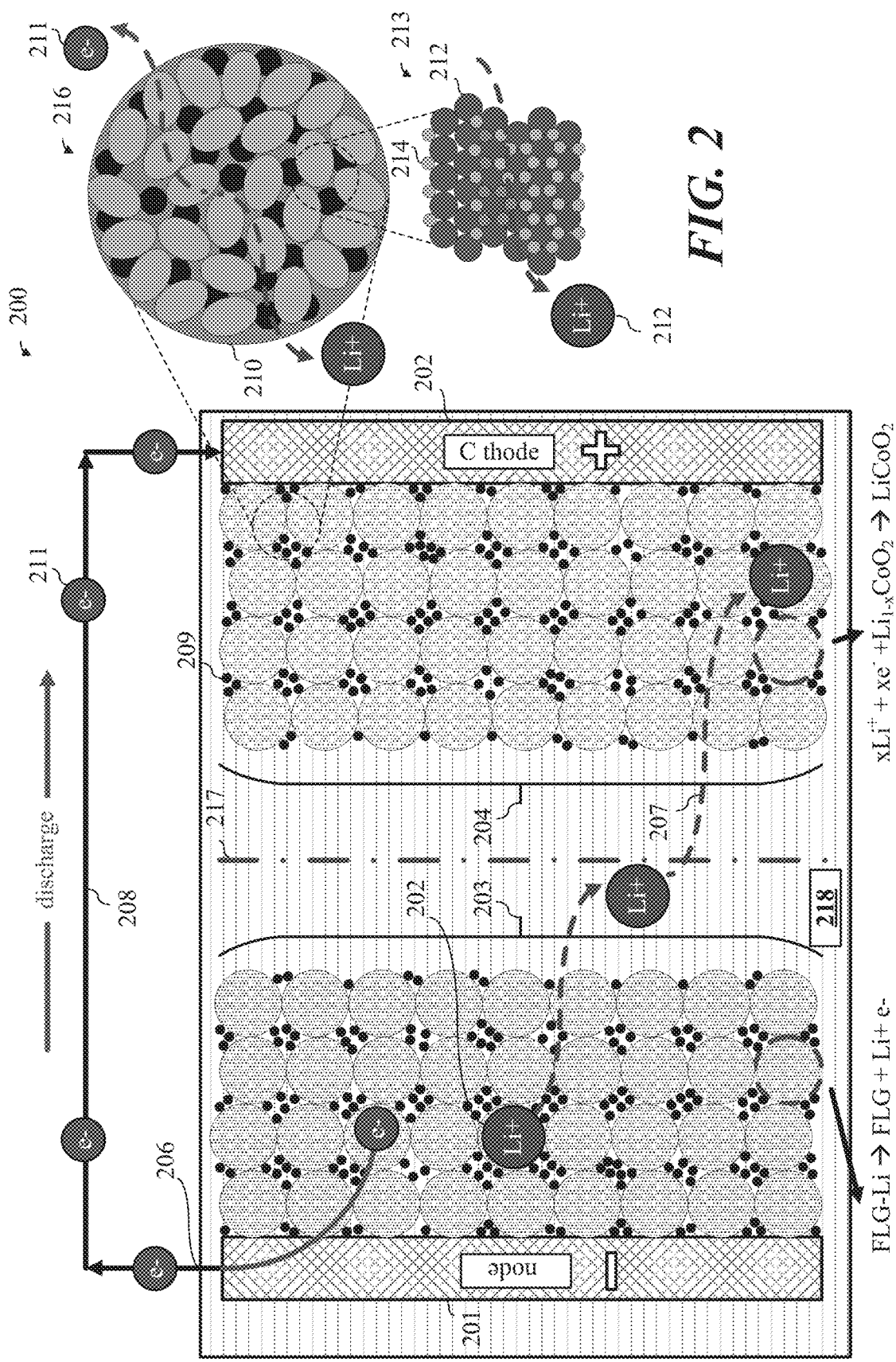

FIGS. 1C1-1C2 show folding techniques related to activating aspects of the printed battery shown in FIGS. 1A-1B, FIGS. 1D1-1D3 show example printed battery features, and FIG. 1E shows a flowchart related to a method for activating an example printed battery.

FIG. 2 shows an example schematic for a traditional Li ion battery incorporating the presently disclosed 3D self-assembled binder-less mesoporous carbon-based particles. An example Li ion secondary electrochemical cell (battery) system 200 is shown in FIG. 2, having an anode 203 and cathode 202 separated by separator 217, all at least partially contained and/or exposed to (Li) ion-conducting electrolyte solution 238 (containing dissociated lithium ion conducting salt 202) as shown. The separator, a porous membrane to electrically isolate the two electrodes from each other, is also in the position showed. Single lithium ions migrate through pathway 207 back and forth between the electrodes of the lithium ion-battery during charging and discharging and are intercalated into the active materials.

During discharging, when lithium is deintercalated from the negative electrode (anode 203 and/or hierarchical mesoporous carbon-based anode 203, where copper functions as the current collector), electrons 206 are released. The active materials of the positive electrode (cathode 202 and/or hierarchical mesoporous carbon-based cathode 204) are, for example, mixed oxides. Those of the negative electrode are graphite and amorphous carbon compounds. The positive electrode (cathode 202 and/or hierarchical mesoporous carbon-based cathode 204) contains active materials such as mixed oxides. The active materials of the negative electrode (anode 203 and/or hierarchical mesoporous carbon-based anode 203) are graphite and amorphous carbon compounds. These are the materials into which the lithium is intercalated.

Notably, lithium ion conducting salt 202 (also referring to Li ions generally) can intercalate into any one or more of the unique carbon-based structures (referring the mesoporous carbon-based particle 300A, 300E, carbon-scaffold 300H, and lithiated carbon-scaffold 400A and/or the like employed as an anode 203, replacing traditional anode 203, and/or a cathode 204, replacing traditional cathode 202) all of which are proprietary to LytEn, Inc., of Sunnyvale, CA, to achieve surprising and wholly unexpected specific capacity retention capability far in excess of the 372 mAh/g values commonly cited in traditional Li ion battery related technologies, inclusive of performance at a level 3× or greater (referring to specific capacity retention capabilities exceeding 3,300 mAh/g or more), all made possible through the unique, multi-modal, hierarchical pores 303A and/or 307F defined by open porous scaffold 302A of mesoporous carbon-based particle 300A and/or 300E. Li ions form complexes and/or compounds with S, for example, and are temporarily retained during charge-discharge cycles at levels not otherwise achievable through conventional unorganized carbon structures requiring adhesive definition and combination via a binder, which can (as discussed earlier) also inhibit overall battery performance and longevity.

Lithium ions migrate from the negative electrode (anode 203 and/or hierarchical mesoporous carbon-based anode 203, any one or more of which further include and/or are defined by mesoporous carbon based particles 300A and/or 300E with minute carbon particles 209 interspersed therein) through the electrolyte 238 and the separator 217 to the positive electrode (cathode 202 and/or hierarchical mesoporous carbon-based cathode 204, any one or more of which further include and/or are defined by mesoporous carbon based particles 300A and/or 300E with minute carbon particles 209 interspersed therein) ([using] aluminium as a current collector). Here, lithium metal 234 microconfined (as shown in enlarged areas 236 and 233) within hierarchical mesoporous carbon-based anode 203 (and in between graphene sheets 232 associated therewith as shown in area 233) may dissociate pursuant to the following equation (3):

$$\text{FLG-Li} \rightarrow \text{FLG} + \text{Li} + e- \quad (1)$$

Eq. (3) shows electrons 233 discharging 208 to power an external load and lithium ions 232 migrating to cathode 202 and/or hierarchical mesoporous carbon-based cathode 204 to return to a thermodynamically favored position within a cobalt oxide-based lattice pursuant to the following equation (2):

$$x\text{Li}^+ + xe^- + \text{Li}_{3-x}\text{CoO}_2 \rightarrow \text{LiCoO}_2. \quad (2)$$

During charging, this process is reversed, where lithium ions 202 migrate from the positive electrode through the electrolyte and the separator to the negative electrode.

Disclosed carbon-based structures (referring to the surprising favorable specific capacity values made possible by the unique multi-modal hierarchical structures of mesoporous carbon-based particle 300A, 300E and/or derivatives thereof, including carbon scaffold 300H and lithiated carbon scaffold 400A) build upon traditional advantages offered by lithium-ion technology. Compared to sodium or potassium ions, the small lithium ion exhibits a significantly quicker kinetics in the different oxidic cathode materials. Another difference: as opposed to other alkaline metals, lithium ions can intercalate and deintercalate reversibly in graphite and silicon. Furthermore, a lithiated graphite electrode enables very high cell voltages. Disclosed carbon-based structures uniquely and unexpectedly enhance the ease through which lithium ions can intercalate and deintercalate reversibly between graphene sheets, due to the unique lay-out of few-layer graphene (FLG) (2-32 layers of graphene in a generally horizontally stacked configuration) 303C as employed in mesoporous carbon-based particle 300A and/or the like, and are suitable for application in traditional cylindrical (hardcase), pouch cell (softpack), and prismatic (hardcase) applications.

3D Self-Assembled Binder-Less Multi-Modal Mesoporous Carbon-Based Particle—In Detail FIGS. 3A-3H show illustrative schematic representations, at various magnification levels, and/or micrographs of a 3D self-assembled binder-less 3D mesoporous carbon-based particle having tunable electrical pathways and ionic conduits throughout the thickness thereof.

FIG. 3A shows a three-dimensional (3D) self-assembled binder-less multi-modal mesoporous carbon-based particle 300A having controllable electrical and ionic conducting gradients distributed throughout, within which various aspects of the subject matter disclosed herein may be implemented. A mesoporous material, as generally understood and as referred to herein, implies a material containing pores with diameters between 2 and 50 nm. For the purposes of comparison, IUPAC defines microporous material as a material having pores smaller than 2 nm in diameter and macroporous material as a material having pores larger than 50 nm in diameter.

Mesoporous materials may include various types of silica and alumina that have similarly sized mesopores. Mesoporous oxides of niobium, tantalum, titanium, zirconium, cerium and tin have been researched and reported. Of all the variants of mesoporous materials, mesoporous carbon has achieved particular prominence, having direct applications in energy storage devices. Mesoporous carbon is defined as having porosity within the mesopore range, and this significantly increases the specific surface area. Another common mesoporous material is "activated carbon", referring to a form of carbon processed to have small, low-volume pores that increase the surface area. Activated carbon, in a mesoporous context, is typically composed of a carbon framework with both mesoporosity and microporosity (depending on the conditions under which it was synthesized). According to IUPAC, a mesoporous material can be disordered or ordered in a mesostructure. In crystalline inorganic materials, mesoporous structure noticeably limits the number of lattice units, and this significantly changes the solid-state chemistry. For example, the battery performance of mesoporous electroactive materials is significantly different from that of their bulk structure.

Mesoporous carbon-based particle 300A is nucleated and grown in an atmospheric plasma-based vapor flow stream of reagent gaseous species, which may include methane ($CH_4$), to form an initial carbon-containing and/or carbon-based particle. That initial particle may be expanded upon either:

(1) "in-flight", describing the systematic coalescence (to nucleate from an initially formed seed particle) of additional carbon-based material derived from incoming carbon-containing gas mid-air within a microwave-plasma reaction chamber (as shown by micrograph 300D in FIG. 1D); or, (2) grown (and/or deposited) directly onto a supporting or sacrificial substrate, such as a current collector, within a thermal reactor.

In chemistry-related context, "coalescence" implies a process in which two phase domains of the same composition come together and form a larger phase domain. Alternatively put, the process by which two or more separate masses of miscible substances seem to "pull" each other together should they make the slightest contact. Mesoporous carbon-based particle 300A, may also be referred to as a "particle." The term "mesoporous" may be defined as a material containing pores with diameters between 2 and 50 nm, according to International Union of Pure and Applied Chemistry ("IUPAC") nomenclature.

Referring to synthesis and/or growth of mesoporous carbon-based particle 300A within a reaction chamber in and/or otherwise associated with a microwave-based reactor, such as a reactor disclosed in U.S. Pat. No. 9,767,992 entitled "Microwave Chemical Processing Reactor," which is incorporated by reference herein in its entirety, or thermal reactor, referring generally to a chemical reactor defined by an enclosed volume in which a temperature-dependent chemical reactor occurs.

Mesoporous carbon-based particle 300A (also mesoporous carbon-based particle 300E as shown in FIG. 1E) is synthesized with a three-dimensional (3D) hierarchical structure comprising short range, local nano-structuring in combination with long range approximate fractal feature structuring, which in this context refers to the formation of successive layers involving the 90—degree rotation of each successive layer relative to the one beneath it, and so on and so forth, allowing for the creation of vertical (or substantially vertical) layers and/or intermediate ("inter") layers.

The plurality of hierarchical (and/or contiguous) pores 307F (as shown in FIG. 1F) at least in part further define open porous scaffold 302A with one or more Li ion diffusion pathways 309F (as shown in FIG. 1F) having:

(1) microporous frameworks defined by a dimension 303F of >50 nm that provide tuneable Li ion conduits;

(2) mesoporous channels defined by a dimension 303F of about 20 nm to about 50 nm (defined under IUPAC nomenclature and referred to as "mesopores" or "mesoporous") that act as Li ion-highways for rapid Li ion transport therein; and (3) microporous textures defined by a dimension 103F of <4 nm for charge accommodation and/or active material confinement.

Li ion diffusion pathways 309F and/or hierarchical porous network 100F more generally may act as or otherwise provide active Li intercalating structures, which may provide a source for specific capacity of an anode or cathode Li ion battery electrode at between about 744 mAh/g to about 1,116 mAh/g. Li may infiltrate open porous scaffold to at least partially chemically react with exposed carbon therein. Mesoporous carbon-based particle 300A may be synthesized at least in part by a vapor flow stream of gaseous reagents including any one or more of a saturated or unsaturated hydrocarbon, such as methane ($CH_4$), flowed onto a substrate in a reactor, such as a microwave-based reactor and/or a thermal reactor.

One or more physical, electrical, chemical and/or material properties of the mesoporous carbon-based particle 300A may be defined during its synthesis. Also, dopants (referring to traces of impurity element that is introduced into a chemical material to alter its original electrical or optical properties, such as Si, SiO, $SiO_2$, Ti, TiO, Sn, Zn, and/or the like) may be dynamically incorporated during synthesis of mesoporous carbon-based particle 300A to at least in part affect material properties including: electrical conductivity, wettability, and/or ion conduction or transport through hierarchical porous network 100F. Microporous textures having dimension 103F and/or hierarchical porous network 100F more generally may be synthesized, prepared or otherwise created to also (or otherwise) include smaller pores for chemical micro-confinement, the smaller pores being defined as ranging from 1 to 3 nm. Also, each graphene sheet (as shown in FIG. 1C) may range from 50 to 200 nm in diameter ($L_a$).

Figure 4A:
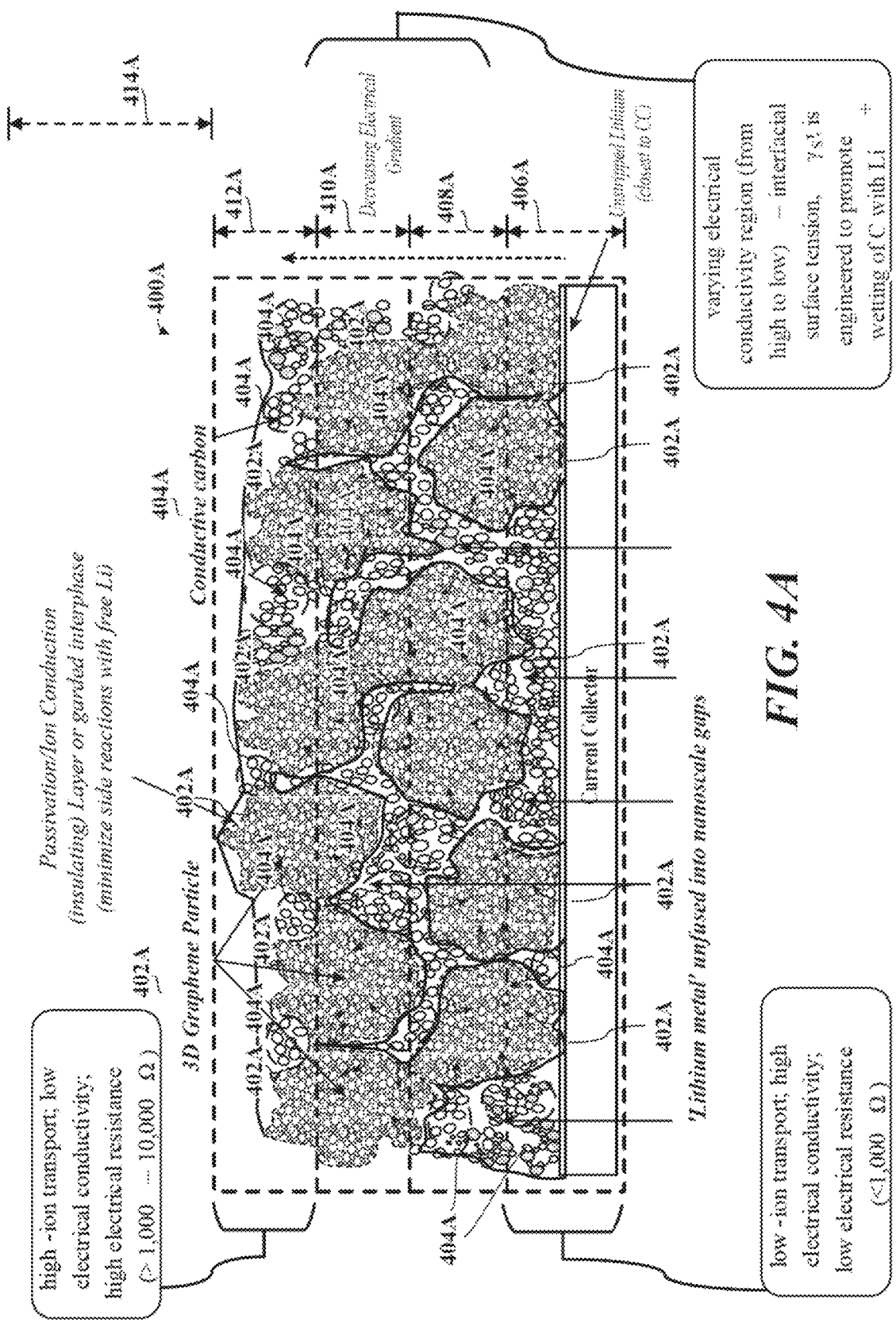
FIG. 4A shows an illustrative schematic representation of a multi-layered carbon-based scaffolded structure, each layer comprising various concentrations of any one or more of the 3D mesoporous carbon-based particles shown herein, deposited on an electrically conductive substrate, the multi-layered carbon-based scaffolded structure having lithium metal infused into nanoscale gaps therein.
Figure 4B:
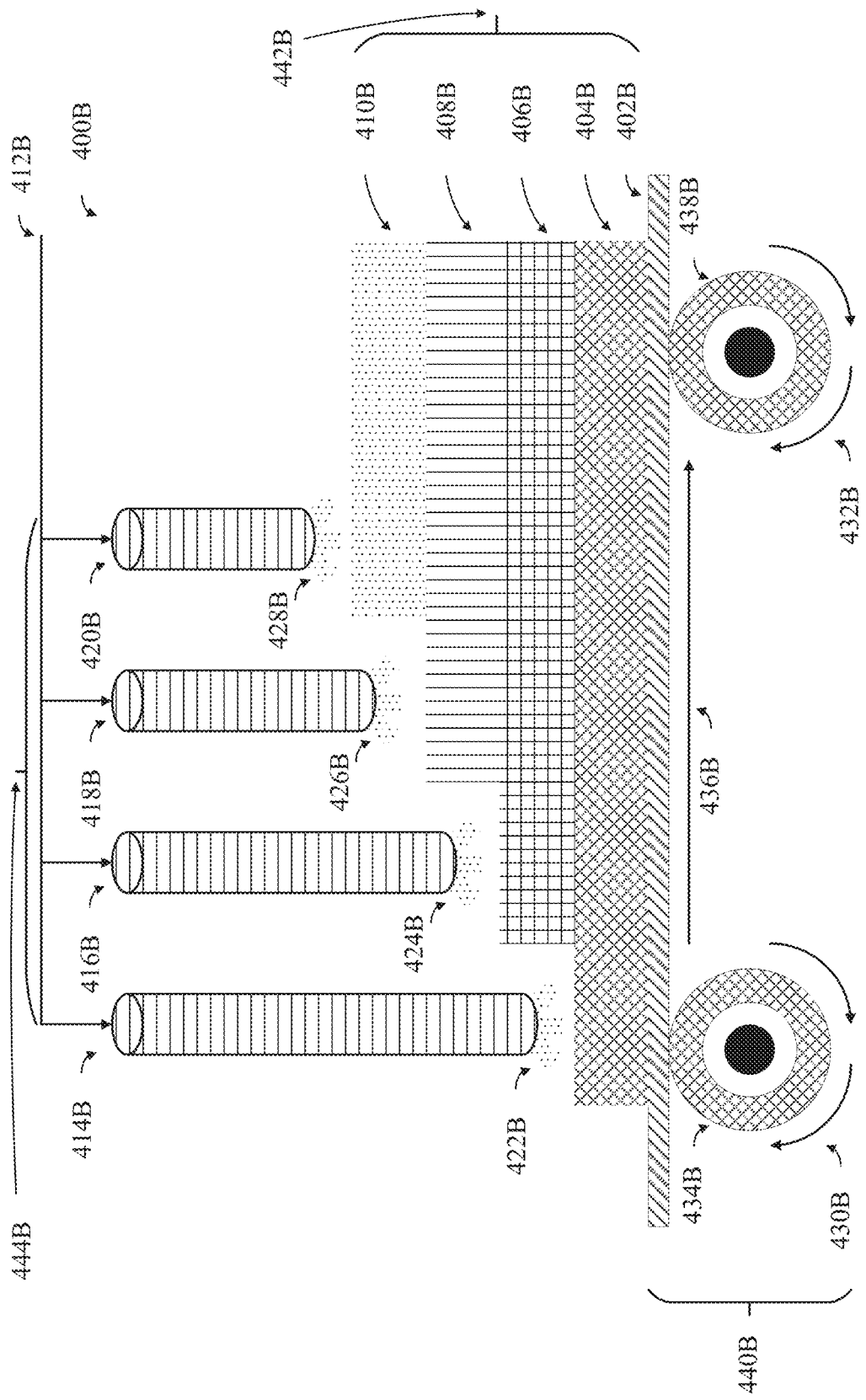
FIG. 4B shows an illustrative schematic representation of a series of plasma spray torches oriented in a substantially continuous sequence above a roll-to-roll (R2R) processing apparatus, where the plasma spray torches are configured to grow the 3D mesoporous carbon-based particles in an incremental layer-by-layer manner.

Hierarchical porous network 100F, may be a further magnified and/or detailed variant of open porous scaffold 302A, may provide one or more active Li intercalating structures, to be further described in structure and/or functionality in connection with FIGS. 6-19C, which show various topic diagrams, flowcharts, schematics, photographs and/or micrographs related to lithium, lithium ion, sulphide, and/or lithium, sulfur and/or other element derived chemical substances and/or compounds infiltrated and/or infused into the multi-layered carbon-based scaffolded structure shown in FIG. 4B. Open porous scaffold 302A may be created independent of a binder, such as a traditional, nonconductive polymer binder typically used in conjunction with and a conductive additive onto a metal foil current collector in battery end-use applications. Traditional configurations involving usage of a binder can lead to electronic/current conduction-related or ionic constrictions and poor contacts due to randomly distributed conductive phases. Moreover, when high-capacity electrode materials are employed, relatively high physical stress generated during electrochemical reactions can disrupt mechanical integrity of traditional binder systems, therefore, in turn, reducing cycle life of batteries.

A vapor flow stream used to synthesize mesoporous carbon-based particle 300A may be flowed in part into a vicinity of a plasma, such as that generated and/or flowed into a reactor and/or chemical reaction vessel. Such a plasma reactor may be configured to propagate microwave energy toward the vapor flow stream to at least in part assist with synthesis of mesoporous carbon-based particle 300A, may involve carbon-particle based and/or derived nucleation and growth from constituent carbon-based gaseous species, such as methane ($CH_4$), where such nucleation and growth may substantially occur from an initially formed seed particle within a reactor. More particularly, such a reactor accommodates control of gas-solid reactions under non-equilibrium conditions, where the gas-solid reactions may be controlled at least in part by any one or more of:
(1) ionization potentials and/or thermal energy associated with constituent carbon-based gaseous species introduced to the reactor for synthesis of the mesoporous carbon-based particle; and/or
(2) kinetic momentum associated with the gas-solid reactions.

The vapor flow stream may be flowed into a reactor and/or reaction chamber for the synthesis of mesoporous carbon-based particle 300A at atmospheric pressure. And change in wettability of mesoporous carbon-based particle 300A (and/or any constituent members such as open porous scaffold 302A) at least in part may involve adjustment of polarity of a carbon matrix associated with mesoporous carbon-based particle 300A.

Those skilled in the art will appreciate that the representations provided in FIGS. 1A-1D, 1E and 1F, are provided as examples. Sample representations are shown of mesoporous carbon-based particle 300A, including:
(1) when synthesized in a microwave-based reactor in micrograph 300D in FIG. 3D;
(2) when synthesized in the form of multi-shell fullerene (CNO);
(3) when used to decorate graphite to form graphene-decorated graphite; and,
(4) when synthesized in-flight in a microwave reactor.

Mesoporous Carbon-Based Particle-Procedures for Synthesis Microwave Reactor

As introduced above, a vapor flow stream including carbon-containing constituent species, such as methane ($CH_4$) may be flowed into one of two general reactor types:
(1) a thermal reactor; or,
(2) a microwave-based (and/or "microwave") reactor. Suitable types of microwave reactors are disclosed in U.S. Pat. No. 9,767,992.

An example microwave processing reactor used to synthesize mesoporous carbon-based particle 300A may include microwave-generating energy source and a field-enhancing waveguide. The field-enhancing waveguide has a field-enhancing zone between a first cross-sectional area and a second cross-sectional area of the waveguide, and also has a plasma zone and a reaction zone. The second cross-sectional area is smaller than the first cross-sectional area, is farther away from the microwave energy source than the first cross-sectional area and extends along a reaction length of the field-enhancing waveguide. The supply gas inlet is upstream of the reaction zone. In the reaction zone, a majority of the supply gas flow is parallel to the direction of the microwave energy propagation. The supply gas is used to generate a plasma in the plasma zone to convert a process input material into separated components in the reaction zone at a pressure of at least 0.1 atmosphere, with a preference for 1 atmosphere where the favorable physical properties of mesoporous carbon-based particle 300A, as discussed above, were discovered.

Propagation of microwave energy toward the carbon-containing or carbon-based vapor flow stream at least in part assists with synthesis of mesoporous carbon-based particle 300A and facilitates carbon-particle nucleation and growth within a reactor.

The term "in-flight" implies a novel method of chemical synthesis based on contacting particulate material derived from inflowing carbon-containing gaseous species, such as those containing methane ($CH_4$), to "crack" such gaseous species. "Cracking", as generally understood and as referred to herein, implies the technical process of methane pyrolysis to yield elemental carbon, such as high-quality carbon black, and hydrogen gas, without the problematic contamination by carbon monoxide, and with virtually no carbon dioxide emissions. A basic endothermic reaction that may occur within a microwave reactor is expressed as equation (1) below:

$$CH_4 + 74.85 \text{ kJ/mol} \rightarrow C + 2H_2 \qquad (1)$$

Carbon derived from the above-described "cracking" process and/or a similar or a dissimilar process may fuse together while being dispersed in a gaseous phase, referred to as "in-flight", to create carbon-based particles, structures, (substantially) 2D graphene sheets, 3D agglomerations, and/or pathways defined therein, including:

(1) a plurality of interconnected 3D agglomerations 303B of multiple layers of graphene sheets 303C (also, each sheet of graphene is schematically depicted in FIG. 1C) that are sintered together to form an open porous scaffold 302A that facilitates electrical conduction along and across contact points of the graphene sheets 303C (which, as shown in FIG. 1B, may include and/or refer to 5 to 15 layers of graphene are oriented in a stacked configuration to have a vertical height referred to as a stack height ($L_c$)); and, (2) a plurality of hierarchical pores 307F (as shown in FIG. 1F, and including pores 304F, 305F, and/or pathways 306F and/or 309F, any one or more which may be of a different dimension than the others) interspersed with the plurality of interconnected 3D agglomerations 303B of multiple layers of graphene sheets 303C, that may comprise one or more of single layer graphene (SLG), few layer graphene (FLG) defined as ranging from 5 to 15 layers of graphene, or many layer graphene (MLG), throughout the multi-modal mesoporous carbon-based particle 300A and/or 300E to define a hierarchical porous network 100F that facilitates rapid Li ion (Li+) 108F diffusion therein by orienting and/or manipulating, such as by shortening, Li ion diffusion pathways 306F and/or 309F.

As introduced earlier, interconnected 3D agglomerations of multiple layers of graphene sheets 303B sinter (or otherwise adjoin) together to serve as a type of intrinsic, self-supporting, "binder" or joining material allowing for the elimination of a separate traditional binder material. Sintering, or "frittage," as commonly understood and as referred to herein, implies the process of compacting and forming a solid mass of material by heat or pressure without melting it to the point of liquefaction. Sintering happens naturally in mineral deposits or as a manufacturing process used with metals, ceramics, plastics, and other materials. The atoms in the materials diffuse across the boundaries of the particles, fusing the particles together and creating one solid piece. Since sintering temperature does not have to reach the melting point of the material, sintering may be chosen as the shaping process for materials with extremely high melting points such as tungsten (W) and molybdenum (Mo). The study of sintering in metallurgy powder-related processes is known as powder metallurgy. An example of sintering is when ice cubes in a glass of water adhere to each other, which is driven by the temperature difference between the water and the ice. Examples of pressure-driven sintering are the compacting of snowfall to a glacier, or the forming of a hard snowball by pressing loose snow together.

Few layer graphene (FLG), defined herein as ranging from 5 to 15 layers or sheets of graphene, can sintered, as so-described above, at an angle that is not flat relative to other FLG sheets to nucleate and/or grow at an angle and therefore "self-assemble" over time. Alternative configurations can exist where techniques other than sintering are employed (or at least partially employed in conjunction with sintering), such as fusing of the FLG sheets to each other at defined right degree angles to define an orthogonally grown carbon-based structure, scaffold, matrix, sponge and/or the like. Moreover, process conditions may be tuned to achieve synthesis, nucleation, and/or growth of 3D multi-modal mesoporous carbon-based particles on a component and/or a wall surface within a reaction chamber, or entirely in-flight (upon contact with other carbon-based materials).

Electrical conductivity of deposited carbon and/or carbon-based materials may be tuned by adding metal additions into the carbon phase in the first part of the deposition phase or to vary the ratios of the various particles discussed. Other parameters and/or additions may be adjusted, as a part of an energetic deposition process, such that the degree of energy of deposited carbon and/or carbon-based particles will either: (1) bind together; or (2) not bind together.

By nucleating and/or growing the multi-modal mesoporous carbon-based particle in an atmospheric plasma-based vapor flow stream either in-flight or directly onto a supporting or sacrificial substrate, a number of the steps and components found in both traditional batteries and traditional battery-making processes may be eliminated. Also, a considerable amount of tailoring and tunability can be enabled or otherwise added into the discussed carbons and/or carbon-based materials.

For instance, a traditional battery may use a starting stock of active materials, graphite, etc., which may be obtained as off-the-shelf materials to be mixed into a slurry. In contrast, the 3D self-assembled binder-less multi-modal mesoporous carbon-based particle 300A disclosed herein may enable, as a part of the carbon or carbon-based material synthesis and/or deposition process, tailoring and/or tuning the properties of materials, in real-time, as they are being synthesized in-flight and/or deposited onto a substrate. This capability presents a surprising, unexpected, and substantial favorable departure from that currently available regarding creation of carbon-based scaffolded electrode materials in the secondary battery field.

Reactor and/or reactor designs disclosed in U.S. Pat. No. 9,767,992 may be adjusted, configured and/or tailored to control wanted or unwanted nucleation sites on internal surfaces of reaction chambers exposed to carbon-based gaseous feedstock species (such as methane ($CH_4$)). In-flight particles qualities may be influenced by their solubility in the gaseous species in which they are flowed in such that once a certain energy level is achieved, the carbon may "crack off" (as so described by "cracking") and form its own solid in a microwave reactor.

Adjusting for Unwanted Carbon Accumulation on Reaction Chamber Walls

Moreover, tuning of disclosed reactors and related systems may be performed to both proactively and reactively address issues associated with carbon-based microwave reactor clogging. For instance, open surfaces, feed holes, hoses, piping, and/or the like may accumulate unwanted carbon-based particulate matter as a by-product of synthetic procedures performed to create mesoporous carbon-based particle 300A. A central issue observed in a microwave reactor may include this tendency to experience clogging in and/or along orifices, the reason being related to walls and other surfaces exposed to in-flowing gaseous carbon-containing species having carbon solubility as well. Therefore, is it possible to unwantedly grow on the walls of a reaction chamber and/or on the exit tube. Over time, those growths will extend out and impinge flow and can shut down chemical reactions occurring within the reactor and/or reaction chamber. Such a phenomena may be akin to tube (exhaust) wall build-up of burnt oil in a high-performance or racing internal combustion engine, where, instead of burning (combusting) fossil-fuel based gasoline, methane is used to result in the unwanted deposit of carbon on reaction chamber wells since metal inside the reaction chamber itself has a carbon solubility level.

Although methane is primarily used to create mesoporous carbon-based particle 300A, in theory any carbon-containing and/or hydrocarbon gas, like $C_2$ or acetylene or any one or more of: $C_2H_2$, $CH_4$, butane, natural gas, biogas, derived from decomposition of biological matter, will function to provide a carbon-containing source.

The described uncontrolled and unwanted carbon growth within exposed surfaces of a microwave reactor may be compared to that occurring within an internal combustion engine exhaust manifold, rather than within a cylinder bore, of the engine, especially where the plume of plasma, and/or hot, excited gas about to enter into the plasma phase, is at the onset of the manifold, and burnt gas and carbon-based fragments are traveling down and plugging-up flow through the manifold, cross-pipes, and catalytic converter, and exit-pipes. Process conditions may therefore be proactively tuned to adjust and therefore accommodate for potential carbon-build-up as so-described in the microwave reactor, which relies on the presence of a plasma for hydrocarbon gas cracking. To maintain this plasma, a certain set of conditions must be maintained, otherwise back-pressure accumulation can potentially destroy the plasma prior to its creation and subsequent ignition, etc.

Thermal Reactor

In the alternative (or in certain cases, in addition or combination with) synthesis of mesoporous carbon-based particle 300A in a microwave-based and/or microwave reactor as substantially described above, specifically structured and/or scaffolded carbons and/or carbon-based structures can be created by "cracking" hydrocarbons purely by heat application in a reactor featuring application of thermal radiation, such as heat, referred to herein as a "thermal reactor". Example configurations may include exposure of incoming carbon-based gaseous species, such as any one or more of the aforementioned hydrocarbons, to a heating element, similar to a wire in a lightbulb.

The heating element heats up the inside of a reaction chamber where incoming carbon-containing gas is ionized. The carbon-containing gas is not burnt, due to the absence of sufficient oxygen to sustain combustion, but is rather ionized from contact with incoming thermal radiation, alternatively referred to as heat, and/or other forms of thermal energy to cause nucleation of constituent members of mesoporous carbon-based particle 300A, and ultimately synthesize, via nucleation, mesoporous carbon-based particle 300A in its entirety. In thermal reactors, some, or most, of the observed nucleation of carbon-based particles can occur on walls or on the heating element itself. Nevertheless, particles can still nucleate which are small enough to be cracked by the speed of flowing gas, such particles are captured to assist in the creation of mesoporous carbon-based particle 300A.

Cracked carbons can be used to create CNO as shown, for example, by 100H in FIG. 1H, and/or fullerenes, and smaller fractions of carbons with fullerene internal crystallography.

In comparing synthesis of mesoporous carbon-based particle 300A via the two discussed pieces of equipment, microwave and thermal reactors, the following distinctions have been observed:

(1) microwave reactors can provide tuning capabilities suitable to provide a broader range of allotropes of carbon; whereas,
(2) thermal reactors tend to allow for the fine-tuning of process parameters, such as heat flow, temperature, and/or the like, to achieve the needs of specific end-use application targets of mesoporous carbon-based particle 300A.

For instance, thermal reactors are currently being used to build Li S electrochemical cell electrodes, such as anodes and cathodes. Typical treatment process temperatures range in the thousands of Kelvin, with optimal, surprising, and otherwise unexpected favorable performance properties, such as referring to mesoporous carbon-based particle 300A and/or carbon-based aggregates associated therewith, when compressed, have an electrical conductivity greater than 500 S/m, or greater than 5,000 S/m, or from 500 S/m to 20,000 S/m. Optimal performance has been observed at between 2,000-4,000 K.

Mesoporous Carbon-Based Particle-Physical Properties & Implementation in Batteries Any one or more of the carbon-based structures, intermediaries, or features associated with mesoporous carbon-based particle 300A may be incorporated at least in part into a secondary battery electrode, such as that of a lithium-ion battery, as substantially set forth in U.S. Patent Publication 2019/0173125, which is incorporated by reference herein in its entirety.

Particulate carbon contained in and/or otherwise associated with mesoporous carbon-based particle 300A may be implemented in a Li ion battery cathode as a structural and/or electrically conductive material and have at least a substantially a mesoporous structure as shown by hierarchical porous network 100F with a wide distribution of pore sizes (also referred to as a multi-modal pore size distribution). For example, mesoporous particulate carbon can contain multi-modal distribution of pores in addition or in the alternative to plurality of hierarchical pores 307F (as shown in FIG. 3F) that at least in part further define open porous scaffold 302A with one or more Li ion diffusion pathways 309F. Such pores may have sizes from 0.1 nm to 10 nm, from 10 nm to 100 nm, from 100 nm to 1 micron, and/or larger than 1 micron. Pore structures can contain pores with a bi-modal distribution of sizes, including smaller pores (with sizes from 1 nm to 4 nm) and larger pores (with sizes from 30 to 50 nm). Such a bimodal distribution of pore sizes in mesoporous carbon-based particle 300A can be beneficial in sulfur-containing cathodes in lithium ion batteries, as the smaller pores (1 to 4 nm in size) can confine the sulfur (and in some cases control of saturation and crystallinity of sulfur and/or of generated sulfur compounds) in the cathode, and the larger pores (30 to 50 nm in size, or pores greater than twice the size of solvated lithium ions) can enable and/or facilitate rapid diffusion (or, mass transfer) of solvated Li ions in the cathode.

As discussed, the lithium-sulfur battery (Li—S battery) is a type of rechargeable battery, notable for its high specific energy. A lithium/sulfur (Li/S) battery (such as that represented by sulfur (S) infiltrated into hierarchical pores 307F of mesoporous particle 300E (such as where S infiltrates open porous scaffold 302A to deposit on internal surfaces of mesoporous carbon-based particle 300A, 300E and/or within pores 307F), as shown in at least FIGS. 3A and 3E respectively, and by schematic 300G shown in FIG. 1G, showing intermediate steps associated with the reduction of sulfur to the sulfide ion ($S^{2-}$). Incorporation of S into Li ion batteries may result in a 3-5 fold higher theoretical energy density than state-of-art Li ion batteries without S, and research has been ongoing for more than three decades. However, the commercialization of Li/S battery still, in some respects, cannot be fully realized due to many problematic issues, including short cycle life, low cycling efficiency, poor safety and a high self-discharge rate. All these issues are related to the dissolution of lithium polysulfide (PS), the series of sulfur reduction intermediates, in liquid electrolyte and to resulting parasitic reactions with the lithium anode and electrolyte components. On the other hand, the dissolution of PS is essential for the performance of a Li/S cell. Without dissolution of PS, the Li/S cell cannot operate progressively due to the non-conductive nature of elemental sulfur and its reduction products.

Mesoporous Carbon-Based Particle-Formed to Address Polysulfide (PS)—Related Challenges Seeking to address at least some of the challenges associated with such polysulfide (PS) systems, mesoporous carbon-based particle 300A and cathodic active material form a meta-particle framework, where cathodic electroactive materials (such as elemental sulfur that may form PS compounds 300G as shown in FIG. 1G) are arranged within mesoporous carbon pores/channels, such as within any one or more of hierarchical pores 307F (as shown in FIG. 1F, including pores 304F, 305F, and/or pathways 306F and/or 309F). S can be, for example, incorporated within pores 307F at a loading level that represents 35-100% of the total weight/volume of active material in mesoporous carbon-based particle 300A and/or 300E overall.

This type of organized particle framework can provide a low resistance electrical contact between the insulating cathodic electroactive materials (such as elemental sulfur) and the current collector while providing relatively high exposed surface area structures that are beneficial to overall specific capacity (and that may be at least assist lithium ion micro-confinement as enhanced by the formation of Li S compounds temporarily retained in hierarchical pores 307F, and the controlled release and migration of Li ions as related to electric current conduction) in a battery electrode and/or system. Implementations of mesoporous carbon-based particle 300A can also benefit cathode stability by trapping at least some portion of any created polysulfides by using tailored structures, such as that shown by hierarchical pores 307F, to actively prevent them from unwantedly migrating through electrolyte to the anode resulting in unwanted parasitic chemical reactions associated with battery self-discharge.

Unwanted Migration of Polysulfides During Li S Battery System Usage—Generally

With reference to polysulfide shuttle mechanisms observed in Li S battery electrodes and/or systems, polysulfides dissolve very well in electrolytes. This causes another lithium-sulfur cell characteristic, the so-called shuttle mechanism. The polysulfides $S_{n2}$—that form and dissolve at the cathode, diffuse to the lithium anode and are reduced to $Li_2S_2$ and $Li_2S$. (The polysulfide species $S_n2$— that form at the cathode during discharging dissolve in the electrolyte there. A concentration gradient versus the anode develops, which causes the polysulfides to diffuse toward the anode. Step by step, the polysulfides are distributed in the electrolyte.) Subsequent high-order polysulfide species react with these compounds and form low-order polysulfides $S_{(n-x)}$. This means that the desired chemical reaction of sulfur at the cathode partly also takes place at the anode in an uncontrolled fashion (chemical or electrochemical reactions are conceivable), which negatively influences cell characteristics.

If low-order polysulfide species form near the anode, they diffuse to the cathode. When the cell is discharged, these diffused species are further reduced to $Li_2S_2$ or $Li_2S$. Simply put, the cathode reaction partly takes place at the anode during the discharging process or, rather, the cell self-discharges. Both are undesirable effects decreasing [specific] capacity. In contrast, the diffusion to the cathode during the charging process is followed by a re-oxidation of the polysulfide species from low order to high order. These polysulfides then diffuse to the anode again. This cycle is known as the shuttle mechanism. If the shuttle mechanism is very pronounced, it is possible that a cell can accept an unlimited charge, it is 'chemically short circuited'.

In general, the shuttle mechanism causes a parasitic sulfur active matter loss. This is due to the uncontrolled separation of $Li_2S_2$ and $Li_2S$ outside of the cathode area and it eventually causes a considerable decrease in cell cycling capability and service life. Further aging mechanisms can be an inhomogeneous separation of $Li_2S_2$ and $Li_2S$ on the cathode or a mechanical cathode structure breakup due to volume changes during cell reaction.

Hierarchical Pores of Mesoporous Carbon-Based Particle to Prevent Lithium Shuttle To address the unwanted phenomenon of PS shuttling as so described above, any one or more of the plurality of hierarchical pores 307F of mesoporous carbon-based particle 300A in a cathode can provide a suitable region, formed with an appropriate dimension, to drive the creation of lower order polysulfides (such as S and $Li_2S$) and therefore prevent the formation of the higher order soluble polysulfides ($Li_xS_y$, with y greater than 3) that facilitate lithium shuttle (such as loss) to the anode. As described herein, the structure of the particulate carbon and the cathode mixture of materials can be tuned during particulate carbon formation (within a microwave plasma or thermal reactor). In addition, cathodic electroactive materials (elemental sulfur) solubility and crystallinity in relation to lithium phase formation, can be confined/trapped within the micro/meso porous framework.

The lithium-ion batteries disclosed herein can incorporate particulate carbon as presented by mesoporous carbon-based particle 300A and/or any derivatives thereof into the cathode, anode, and/or one or both substrates with improved properties compared to conventional carbon materials. For example, the particulate carbon can have high compositional purity, high electrical conductivity, and a high surface area compared to conventional carbon materials. In some implementations, the particulate carbon also has a structure that is beneficial for battery properties, such as small pore sizes and/or a mesoporous structure. In some cases, a mesoporous structure can be characterized by a structure with a wide distribution of pore sizes (with a multimodal distribution of pore sizes). For example, a multimodal distribution of pore sizes can be indicative of structures with high surface areas and a large quantity of small pores that are efficiently connected to the substrate and/or current collector via material in the structure with larger feature sizes (such as that provide more conductive pathways through the structure). Some non-limiting examples of such structures are fractal structures, dendritic structures, branching structures, and aggregate structures with different sized interconnected channels (composed of pores and/or particles that are cylindrical and/or spherical).

In some implementations, the substrate, cathode, and/or anode contains one or more particulate carbon materials. In some implementations, the particulate carbon materials used in the lithium-ion batteries disclosed herein may be those described in in U.S. Pat. No. 9,997,334, discussed above. In some implementations, the particulate carbon materials contain graphene-based carbon materials that comprise a plurality of carbon aggregates, each carbon aggregate having a plurality of carbon nanoparticles, each carbon nanoparticle including graphene, optionally including multi-walled spherical fullerenes, and optionally with no seed particles (such as with no nucleation particle). In some cases, the particulate carbon materials are also produced without using a catalyst. The graphene in the graphene-based carbon material has up to 15 layers. A ratio (such as percentage) of carbon to other elements, except hydrogen, in the carbon aggregates is greater than 99%. A median size of the carbon aggregates is from 1 micron to 50 microns, or from 0.1 microns to 50 microns. A surface area of the carbon aggregates is at least 10 $m^2/g$, or is at least 50 $m^2/g$, or is from 10 $m^2/g$ to 300 $m^2/g$ or is from 50 $m^2/g$ to 300 $m^2/g$, when measured using a Brunauer-Emmett-Teller (BET) method with nitrogen as the adsorbate. The carbon aggregates, when compressed, have an electrical conductivity greater than 500 S/m, or greater than 5000 S/m, or from 500 S/m to 20,000 S/m.

Mesoporous Carbon-Based Particle-Departure from Conventional Technology to Yield Surprising Favorable Results Conventional composite-type Li-ion or Li S battery electrodes (shown in FIG. 2B) may be fabricated from a slurry cast mixture of active materials (shown as in FIG. 2A), including: conductive additives (such as fine carbon black and graphite for usage in a battery cathode at a specific aspect ratio), and polymer-based binders that are optimized to create a unique self-assembled morphology defined by an interconnected percolated conductive network. While, in conventional preparations or applications, additives and binders can be optimized to improve electrical conductivity there-through (by, for example, offering lower interfacial impedance) and therefore correspondingly yield improvements in power performance (delivery), they represent a parasitic mass that also necessarily reduces specific (also referred to as gravimetric) energy and density, an unwanted end result for today's demanding high-performance battery applications.

To minimize losses due to parasite mass (such as that caused by increased active and/or inactive ratio), and concurrently enable faster access of electrolyte to the complete surface of an electrode, orienting, re-orienting, and/or otherwise organizing or repositioning ion diffusion pathways 309F to effectively shorten Li ion diffusion path lengths for charge transfer, hierarchical pores 303A and/or open porous scaffold 302A may be created from reduced-size carbon particles and/or active materials (down to nanometer scales), since the external specific surface area (SSA, defined as the total surface area of a material per unit of mass, (with units of $m^2/kg$ or $m^2/g$) or solid or bulk volume (units of $m^2/m^3$ or $m^{-1}$); it is a physical value that can be used to determine the type and properties of a material (soil or snow)) of a sphere increases with decreasing diameter. However, as the particle size is decreased down into the nanometer size range there are associated attractive van der Waal forces that can impede dispersion, facilitate agglomeration, and thereby increase cell impedance and reduce power performance.

Another approach to shortening ion diffusional pathways, referring to ion diffusion pathways 309F shown in FIG. 1F, is to uniquely engineer the internal porosity of the constitutive carbon-based particles, such as those created by the electrically conductive interconnected agglomerations of graphene sheets 303B to create open porous scaffold 302A and/or define hierarchal pores 303A and/or 307F. As per commonly used definitions, and as referred to herein, a "surface curvature" is referred to as a "pore" if its cavity is deeper than it is wide. As a result, this definition necessarily excludes many nanostructured carbon materials where just the external surface area is modified, or in close packed particles where voids (intra-particular) are created between adjacent particles (as in the case of a conventional slurry cast electrode).

With respect to the engineering (referring to the synthesis, creation, formation, and/or growth of mesoporous carbon-based particle 300A either in-flight in a microwave-based reactor or via layer-by-layer deposition in a thermal reactor as substantially described earlier), reactor process parameters may be adjusted to tune the size, geometry, and distribution of hierarchical pores 303A and/or 307F within mesoporous carbon-based particle 300A. Hierarchical pores 303A and/or 307F within mesoporous carbon-based particle 300A may be tailored to achieve performance figures particularly well-suited for implementation in high-performance fast-current delivery devices, such as supercapacitors.

As generally described earlier, a supercapacitor (SC), also called an ultracapacitor, is a high-capacity capacitor with a capacitance value much higher than other capacitors, but with lower voltage limits, that bridges the gap between electrolytic capacitors and rechargeable batteries. It typically stores 10 to 100 times more energy per unit volume or mass than electrolytic capacitors, can accept and deliver charge much, much faster than batteries, and tolerates many more charge and discharge cycles than rechargeable batteries.

In many of the available off-the-shelf commercial carbons used in early supercapacitor development efforts, there were "worm"—like narrow pores which became a bottleneck or liability when operating at high current densities and fast charge- and discharge rates, as electrons may encounter difficulty in flow through, in or around such structures or pathways. Even though pore dimensions were fairly uniform but still adjustable to accommodate a wide range of length scales, real-life achievable performance was still self-limited (as based on the structural challenges inherent to the "worm"—like narrow pores).

Compared to conventional porous materials with uniform pore dimensions that are tuned to a wide range of length scales, the presently disclosed 3D hierarchical porous materials (such as that shown by hierarchical pores 303A and/or 307F within mesoporous carbon-based particle 300A) may be synthesized to have well-defined pore dimensions (such as hierarchical pores 307F including pores 304F, 305F, and/or pathways 306F and/or 309F) and topologies overcome the shortcomings of conventional 'mono-sized' porous carbon particles by creating, multi-modal (such as bi-modal) pores and/or channels having the following dimensions and/or widths:

(1) meso (2 nm<$d_{pore}$ 50 nm) pores; <
(2) macro ($d_{pore}$>50 nm) pores 303A (as shown in micrograph 300A of FIG. 3A) to minimize diffusive resistance to mass transport; and,
(3) micro ($d_{pore}$<2 nm) pores 302A to increase surface area for active site dispersion and/or ion storage (capacitance relating to density and number of ions that can be stored within a given pore size, such as that shown by pore 305F having dimension 103F in FIG. 1F).

Although no simple linear correlation has been experimentally established between: (1) surface area; and, (2) capacitance, mesoporous carbon-based particle 300A offers surprising favorable results in providing optimal micropore size distributions and/or configurations (such as when integrated into a Li ion or Li S battery electrode to achieve certain specific capacity and power values or ranges) that are different for each intended end-use application (such as an electrolyte system) and corresponding voltage window. To optimize capacitance performance, mesoporous carbon-based particle 300A may be synthesized with very narrow "pore size distributions" (PSD); and, as desired or required voltages are increased, larger pores are preferred. Regardless, current state-of-the-art supercapacitors have provided a pathway to engineering the presently disclosed 3D hierarchical structured materials for particular end-use applications.

In contrast to supercapacitors, where capacitance and power performance is primarily governed by, for example:
(1) surface area of the pore wall;
(2) size of pore; and
(3) interconnectivity of the pore channels (which affect electric double layer performance)

Li-ion storage batteries undergo faradaic reduction/oxidation reactions within the active material and thereby may require not only all of the Li ion transport features of a supercapacitor (such as efficiently oriented and/or shortened Li ionic diffusion pathways). Regardless, in any application (including a supercapacitor as well as a traditional Li ion or Li S secondary battery) a 3D nanocarbon-based framework/architecture (such as that defined open porous scaffold 302A) can provide continuous electrical conducting pathways (such as across and along electrically conductive interconnected agglomerations of graphene sheets 303B1 alongside, for example, highly-loaded active material having high areal and volumetric specific capacity.

Mesoporous Carbon-Based Particle—Used as a Formative Material for a Cathode

To address prevailing issues with relatively low electrical and ionic conductivities, volume expansion and polysulfide (PS) dissolution (referring to the PS "shuttle" effect, discussed earlier, leading to lithium loss and capacity fade) in current sulfur cathode electrode designs, mesoporous carbon-based particle 300A has hierarchical pores 303A and/or 307F formed therein to define open porous scaffold 302A, which includes pores 305F with microporous textures 103F having a dimension (such as 1-4 nm cavities) suitable to at least temporarily micro-confine elemental sulfur and/or Li S related compounds. Open porous scaffold 302A, at the same time as confining sulfur as so described, also provides a host scaffold-type structure to manage sulfur expansion to ensure surprising, unexpected, and highly desirable electron transport across the sulfur-carbon interface (such as at contact and/or interfacial regions of sulfur and carbon within pores 305F) by, for example, tailored in-situ nitrogen doping of the carbon within the reactor. Confining sulfur within a nanometer scale cavity (such as pores 305F with microporous textures 103F) favorably alters both:
(1) the equilibrium saturation (solubility product); and,
(2) crystalline behaviour of sulfur, such that sulfur remains confined (as may be necessary for desirable electrical conduction upon dissociation of Li S compounds, etc.) within microporous textures having dimension 103F, with no external driving force required to migrate to the anode electrode.

As a result, unique dimension 103F (including diameter, height and/or width of about 1-4 nm in cavity form as described above) provided by pores 305F results in no need for separators that attempt to impede polysulfide diffusion while, at the same time, negatively impacting cell impedance (referring to the effective resistance of an electric circuit or component to alternating current, arising from the combined effects of ohmic resistance and reactance) and polarization. By using carbon with optimum (relative to elemental sulfur, lithium and/or Li S micro-confinement) and non-optimum multi-modal, referring to hierarchical pores 307F including pores 304F, 102F, and/or 103F, or (alternatively) bi-modal pore distributions, mesoporous carbon-based particle 300A demonstrates, unexpectedly and favorably, operation of the principle of micro-confinement in properly optimized (relative to final end-use application specific demands) structures.

Along with creating delicately engineered ornate, hierarchical multi-modal carbon-based particles, such as mesoporous carbon-based particle 300A and organized scaffolds generated therefrom, mesoporous carbon-based particle 300A further uniquely provides the ability to effectively load or infuse carbon scaffold 300H shown in FIG. 3B (that may be created in-reactor by either:
(1) layer-by-layer deposition of multiple mesoporous carbon-based particles 300A by a slurry-case method; or,
(2) by a continuous sequence of a group of plasma spray-torches, as shown by plasma spray-torch system 400B in FIG. 4B), with sulfur, such as elemental sulfur.

For lithium-sulfur battery performance to practically exceed conventional lithium-ion batteries, industry-scalable techniques must achieve high sulfur loading (such as >70% sulfur per unit volume) relative to all additives and components of a given cathode template, while maintaining the native specific capacity of the sulfur active material. Attempts to incorporate sulfur into a cathode host, such as by any one or more of (performed independently or in any combination): electrolysis, wet chemical, simple mixing, ball milling, spray coating, and catholytes, have either not fully incorporated the sulfur as desirable, or are otherwise not economically scalable or manufacturable. Unlike melt infiltration where small pores are thermodynamically inaccessible, presently disclosed synthetic approaches use an isothermal vapor technique, introduced and reacted at substantially atmospheric pressure, where the high surface free energy of nanoscale pores or surfaces drives the spontaneous nucleation of sulfur containing liquids until a conformal coating of sulfur and/or lithium-containing condensate is reached on inner-facing surfaces of hierarchical pores 303A and/or 307F. In essence, unique vapor infusion process unexpectedly (and favorably) completely infuses sulfur into fine pores (such as any one or more of hierarchical pores 303A and/or 307F and/or pores 304F, 305F and/or pathways 306F and/or 309F) at the core of mesoporous carbon-based particle 300A, and therefore not just at its surface.

Mesoporous Carbon-Based Particle to Create an Electrically Conductive Scaffold

Mesoporous carbon-based particle 300A, may be fabricated any number of ways using both known and novel techniques disclosed herein, including:
(1) slurry-casting, referring to conventional metalworking, manufacturing and/or fabrication techniques in which a liquid material is usually poured into a mold, which contains a hollow cavity of the desired shape, and then allowed to solidify; or
(2) plasma spray-torch system 400B (shown in FIG. 4B), which may be used to perform layer-by-layer deposition to grow mesoporous carbon-based particle 300A incrementally.

Either (1) or (2) as described above, or any other known or novel fabrication techniques, may be used to create carbon scaffold 300H in a "graded" manner, referring to under specifically controlled conditions resulting in corresponding control of:
(1) electrical gradients (referring to interconnected 3D agglomerations of multiple layers of graphene sheets 303B that are sintered together, as discussed earlier, to form open porous scaffold 302A that facilitates electrical conduction along and across contact points of graphene sheets 303B); and, (2) ionic conductive gradients (referring Li ion transport through hierarchical pores 303A and/or 307F, which are defined by electrically conductive interconnected agglomerations of graphene sheets 303B, and cause rapid lithium (Li) ion diffusion effectively shortening Li ion diffusion pathways 309F) throughout thickness of carbon scaffold 300H, in the vertical height direction A as shown in FIG. 3B, of mesoporous carbon-based particle 100.

Reference is made herein to various forms of carbon and/or graphene synthesized in-flight within a reactor (or reaction chamber) as described earlier to create electrically conductive interconnected agglomerations of graphene sheets 303B, which may vary in shape, size, position, orientation, and/or structure. Such variances are influenced in differences in crystallinity and the particular type of carbon allotrope(s) used for creation of electrically conductive interconnected agglomerations of graphene sheets 303B. "Crystallinity", as generally understood and as referred to herein, implies the degree of structural order in a solid. In a crystal, atoms or molecules are arranged in a regular, periodic manner. The degree of crystallinity therefore has a significant influence on hardness, density, transparency, and diffusion.

Mesoporous carbon-based particle 100 can be produced in the form of an organized scaffold, such as a carbon-based scaffold, out of a reactor (including thermal or microwave-based reactor) or be created (at least partially) during post-processing activities taking place outside of primary synthesis within a reactor.

Plasma processing and/or plasma-based processing, may be conducted within a reactor as disclosed in U.S. Pat. No. 9,767,992, where supply gas is used to generate a plasma in the plasma zone to convert a process input material (such as methane and/or other suitable hydrocarbons in a gaseous phase) into separated components in a reaction zone (such as a reaction chamber) to facilitate in-flight synthesis of carbon-based materials, including mesoporous carbon-based particle 300A grown to create carbon scaffold 300H at approximately 1 atmosphere.

Alternative to synthesis by or within a microwave reactor as described above, thermal energy may be directed toward or near carbon-containing feedstock materials supplied in a gaseous phase onto sacrificial substrate 306B to sequentially deposit multiple layers of mesoporous carbon-based particles 300A by, for example, plasma spray-torch system 400B shown in FIG. 4B. Such particles may be either fused together in-flight (in a microwave reactor) or deposited (in a thermal reactor) in a controlled manner to achieve varying concentration levels of carbon-based particles 300A to therefore, in turn, achieve "graded" electrical conductivity proportionate to concentration levels of mesoporous carbon-based particles 300A. Such procedures may be used to formulate porous carbon-based electrode structure (such as carbon scaffold 300H) that has a high degree of tunability (regarding electrical conductivity and ionic transport) while also eliminating many production steps and otherwise retaining a conventional outward appearance.

An objective of producing mesoporous carbon-based particle 300A out of, for example, a microwave reactor, includes producing open porous scaffold 302A with an open cellular structure such that a liquid-phase electrolyte can easily infiltrate into the pores of mesoporous carbon-based particle 300A via (at least) open porous scaffold 302A. As generally understood and as referred to herein, a "porous medium" or a "porous material" refers to a material containing pores, also referred to herein as "voids". Skeletal portions of open porous scaffold 302A may be referred to as a "matrix" or a "frame", and pores (such as hierarchical pores 303A and/or 307F) can be infiltrated with a fluid (liquid or gas), whereas skeletal material is usually formed as a solid material.

Porosity of the Mesoporous Carbon-Based Particle—In Detail

A porous medium, such as mesoporous carbon-based particle 300A, can be characterized by its porosity. Other properties of the medium (such as permeability, tensile strength, electrical conductivity, and tortuosity) may be derived from the respective properties of its constituents (of solid matrix and fluid interspersed therein), as well as media porosity and pore structure. Mesoporous carbon-based particle 300A can be created out of a reactor (and possibly also subsequently post-processed, to be discussed in detail herein) to achieve desirable porosity levels that are unexpectedly conducive for ion diffusion (such as Li ion), whereas contacting electrically conductive interconnected agglomerations of graphene sheets 303B facilitate electron conduction while also allowing for electrons to reunite with positive ions at reaction sites.

Regarding, porosity and tortuosity of open porous scaffold 302A of mesoporous carbon-based particle 300A, an analogy may be made to marbles in a glass jar. Porosity, in this example, refers to spacing between the marbles that allows liquid-phase electrolyte to penetrate into void spaces between the marbles, similar to hierarchical pores 307F that define ion diffusion pathways 309F. The marbles themselves may be like Swiss cheese, by allowing electrolyte not only to penetrate in cracks between agglomerations of graphene sheets 303B, but also into agglomerations of graphene sheets 303B themselves. In this example as well as others, the relative "shortening" of ion diffusion pathways 309F refers to how long it takes Li ions infiltrated therein by, for example, capillary action to contact active material (such as S confined within pores 305F). Ion diffusion pathways 309F accommodate convenient and rapid infiltration and diffusion of electrolyte, which may contain Li ions, into mesoporous carbon-based particle 300A, synthesized further to create carbon scaffold 300H with graded electric conductivity.

The "shortening" of ion diffusion pathways 309F refers toward the shortening of diffusion lengths through which Li ions move within open porous scaffold 302A in carbon scaffold 300H and not active material itself (as it is commonly understood that the diffusion length of the active material may be shortened only by making the thickness of the active material lesser or smaller). Ion diffusion pathways 309F can act as ion buffer reservoirs by controlling flow and/or transport of ions therein to provide a surprisingly favorable freer flowing structure for ion transport therein, as may be beneficial for ion confinement and transport during electrochemical cell charge-discharge cycles. Transport of Li ions throughout ion diffusion pathways 309F in the general directions shown in FIG. 1F can take place in a liquid electrolyte initially infused and captured within open porous scaffold 302A, where such infusion of electrolyte occurs prior to cyclic carbon scaffold 300H usage. Alternatively, examples exist permitting for the initial diffusion and distribution of liquid-phase electrolyte in open porous scaffold 302A of mesoporous carbon-based particle 300A to fill up and occupy hierarchical pores 303A and/or 307F prior to usage of carbon scaffold 300H, synthesized or otherwise created by layer-on-layer deposition of mesoporous carbon-based particles 300A. In alternative or addition to complete filling of open porous scaffold 302A with electrolyte as described, vacuum or air may also be used to fill hierarchical pores 303A at least partially and/or 307F, which may allow or assist with wetting of electrolyte with carbon-containing exposed surfaces within open porous scaffold 302A (to be described further herein).

Once an electrode is formed using carbon scaffold 300H, through additional exposure and electrochemical reactions, Li ions actually bounce from one location to another by a chain reaction, similar to the striking of "newton" balls, where one hits to result in force transference resulting in the movement of other balls. Similarly, each Li ion moves a short distance, yet remains able to move great numbers of Li ions in the collective through this type of chain reaction as described. The extent of individual Li ion movement may be influenced by the quantity of Li ions supplied altogether to carbon scaffold 300H via capillary infusion into open porous scaffold 302A, as may be the crystallographic arrangement of Li ions and/or particles in, around, or within agglomerations of graphene sheets 303B.

Electrochemical Cell Electrode (Anode or Cathode) Created from Carbon Scaffold

Carbon scaffold 300H can be functionally integrated in a variety of battery or supercapacitor applications, battery types including Li ion batteries and Li S batteries, as well as Li air cathodes, upon suitable development. Such an example battery system may include an electrochemical cell configured to supply electric power to a system. The electrochemical cell may have an anode containing an anode active material, a cathode containing a cathode active material, a porous separator disposed between the anode and the cathode, and an electrolyte in ionic contact with the anode active material and the cathode active material.

The anode and cathode may include sacrificial substrate 306B (that is electrically conductive), with a first layer deposited there-upon as a first contiguous film having a first concentration of mesoporous carbon-based particles 300A and/or 302H, each mesoporous carbon-based particle 300A and/or 302H contacting another and being composed of electrically conductive interconnected 3D aggregates of graphene sheets 303B. Aggregates of graphene sheets 303B are sintered together to form open porous scaffold 302A (shown in FIG. 3A) that facilitates electrical conduction along and across contact points of the graphene sheets 303B. Open porous scaffold 302A has a 3D hierarchical structure with mesoscale structuring in combination with micronscale fractal structuring, any one or more further featuring minute carbon-based particles 304H interspersed in and/or between adjacent carbon-based particles 300A and/or 302H.

A porous arrangement is formed in open porous scaffold 302A. The porous arrangement is conducive to receive electrolyte dispersed therein for ion (such as Li ion) transport through interconnected hierarchical pores 303A and/or 307F that define one or more channels including:
 (1) microporous frameworks defined by a dimension 303F of >50 nm that provide tuneable Li ion conduits;
 (2) mesoporous channels defined by a dimension 303F of about 20 nm to about 50 nm (defined under IUPAC nomenclature and referred to as "mesopores" or "mesoporous") that act as Li ion-highways for rapid Li ion transport therein; and
 (3) microporous textures defined by a dimension 103F of <4 nm for charge accommodation and/or active material confinement.

The first layer including a first electrical conductivity ranging from 500 S/m to 20,000 S/m. A second layer is deposited on the first layer. The second layer has a second contiguous film with a second concentration of mesoporous carbon-based particles 300A in contact with each other to yield a second electrical conductivity ranging from 0 S/m to 500 S/m (lower than the first electrical conductivity).

Figure 3G:
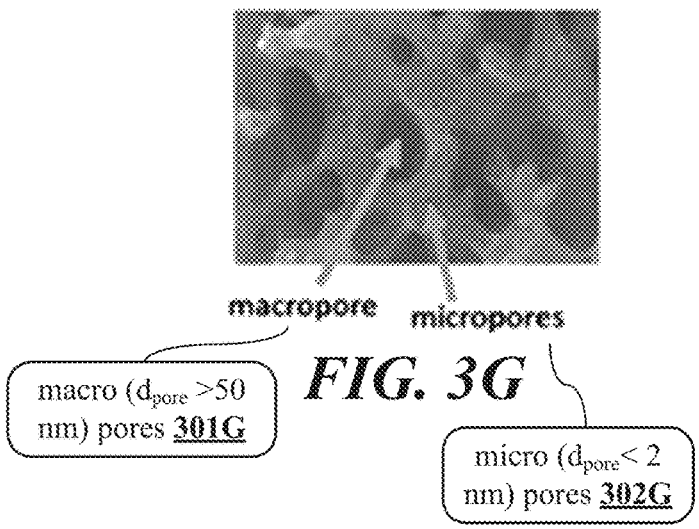
FIG. 3G shows a micrograph of an example enlarged section of the 3D self-assembled binder-less mesoporous carbon-based particle shown in at least FIGS. 1A-1E.

FIG. 3G shows a micrograph of an example enlarged section of the 3D self-assembled binder-less mesoporous carbon-based particle shown in any one or more of the presently disclosed implementations including both macropores 301G and micropores 302G.

Figure 3H:
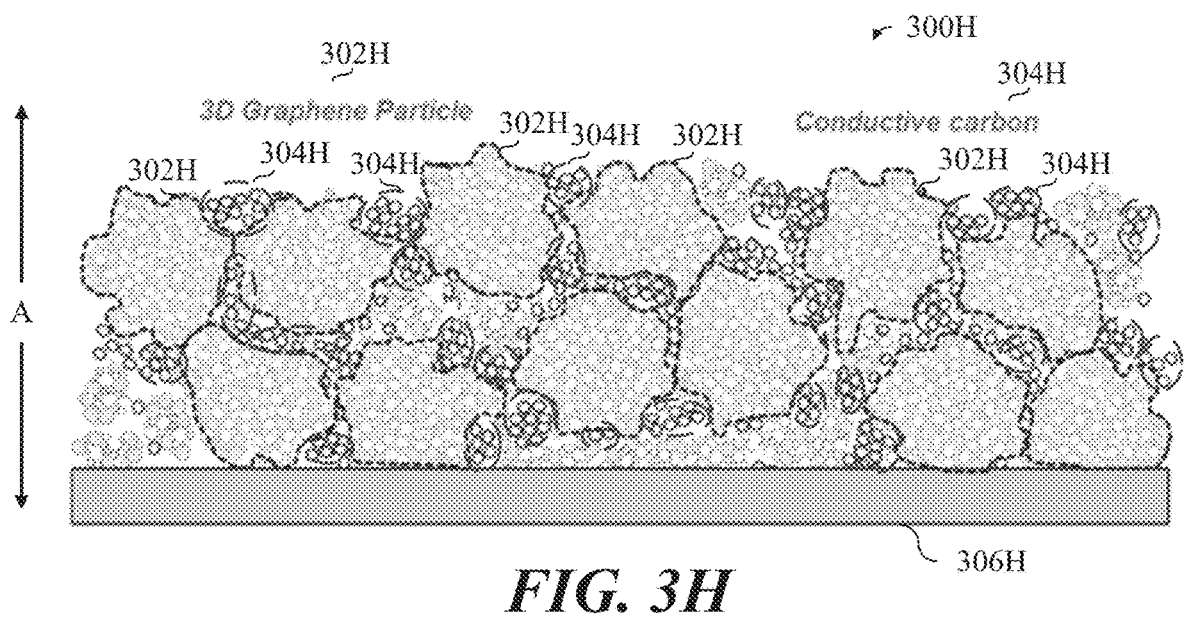
FIG. 3H shows an illustrative schematic representation of a multi-layered carbon-based scaffolded structure, each layer comprising various concentrations of the 3D mesoporous carbon-based particles shown in FIGS. 1A-1F, deposited on an electrically conductive substrate.

FIG. 3H shows an illustrative schematic representation of a multi-layered carbon-based scaffolded structure, each layer comprising various concentrations of the 3D mesoporous carbon-based particles shown in FIGS. 3A-F, deposited on an electrically conductive substrate.

Carbon scaffold 300H may be pre-lithiated and later infused with Li ion liquid solution via capillary action to create lithiated carbon scaffold 400A (to be further explained herein) as shown in FIG. 4A. Interim layers 406A, 408A, 410A, and 412A (having defined thicknesses in the vertical direction extending from the current collector, which may be a sacrificial and/or electrically conductive substrate, toward electrolyte layer 414A) may be synthesized in-flight in a microwave reactor, or deposited layer-by-layer in or out of a thermal reactor. Interim layers 406A, 408A, 410A, and 412A have varying electrical conductivity ranging from high (such as at interim layer 406A) to low (such as at layer 412A) in a direction orthogonal and away from the current collector, which may also be a sacrificial and/or electrically conductive substrate. Varying electrical conductivity may be at least partially proportionate to interfacial surface tension of a Li ion solution infiltrated into the porous arrangement of the open porous scaffold, where infiltration of the Li ion solution is done via capillary infusion engineered to promote wetting (to be further explained herein) of surfaces of open porous scaffold 302A exposed to Li ion solution, as well as the prevalence (concentration) of conductive carbon particles 404A interspersed within mesoporous carbon-based particles 402A (that are equivalent or similar to mesoporous carbon-based particles 300A, 300E and/or the like).

Li ion diffusion pathways 309F (as shown in FIG. 1F) ensure that deposition and stripping operations associated with one or more oxidation-reduction ("redox") reactions occurring within mesoporous carbon-based particles 300A and/or 302H are uniform. Also, anode active material and/or cathode active material resides in pores of the anode and the cathode, respectively, and may contain single-layer graphene (SLG) and/or few-layer graphene (FLG) including from 1 to 10 graphene planes, respectively, the graphene planes being positioned in an aligned orientation along a vertical axis. Anode active material or cathode active material may have a specific surface area from approximately 500 m$^2$/g to 2,675 m$^2$/g when measured in a dried state, and may contain a graphene material comprising any one or more of pre-lithiated graphene sheets, pristine graphene, graphene oxide, reduced graphene oxide, graphene fluoride, graphene chloride, graphene bromide, graphene iodide, hydrogenated graphene, nitrogenated graphene, boron-doped graphene, nitrogen doped graphene, chemically functionalized graphene, physically or chemically activated or etched versions thereof, conductive polymer coated or grafted versions thereof, and/or combinations thereof.

In any one or more of the discussed examples in relation to lithiated carbon scaffold 400A, electrically conductive interconnected agglomerations of graphene sheets 303B are sintered together to form open porous scaffold independent of a binder, however alternative examples do exist where a binder is used. Configurations with or without a binder may each involve open porous scaffold 302A acting or serving as an active lithium intercalating structure with a specific capacity of 744-1,116 mAh/g, or more. Also, examples include the preparation of electrically conductive interconnected agglomerations of graphene sheets 303B using chemically functionalized graphene, involving the surface functionalization thereof, comprising imparting to open porous scaffold 302A a functional group selected from quinone, hydroquinone, quaternized aromatic amines, mercaptan, disulfide, sulfonate (—$SO_3$), transition metal oxide, transition metal sulfide, other like compounds or a combination thereof.

The current collector shown in FIG. 4A, is, for example, at least partially foam-based or foam-derived and is can be selected from any one or more of metal foam, metal web, metal screen, perforated metal, sheet-based 3D structure, metal fiber mat, metal nanowire mat, conductive polymer nanofiber mat, conductive polymer foam, conductive polymer-coated fiber foam, carbon foam, graphite foam, carbon aerogel, carbon xerogel, graphene foam, graphene oxide foam, reduced graphene oxide foam, carbon fiber foam, graphite fiber foam, exfoliated graphite foam, and combinations thereof.

Anode or cathode electrically conductive or insulative material, referred to herein as "active material" can include any one or more of nanodiscs, nanoplatelets, nano-fullerenes, carbon nano-onions (CNOs), nano-coating, or nanosheets of an inorganic material selected from: (i) bismuth selenide or bismuth telluride, (ii) transition metal dichalcogenide or trichalcogenide, (iii) sulfide, selenide, or telluride of a transition metal; (iv) boron nitride, or (v) a combination thereof. The nanodiscs, nanoplatelets, nano-coating, or nano sheets can have a thickness less than 100 nm. In similar or dissimilar examples, the nanoplatelets can have a thickness less than 10 nm and/or a length, width, or diameter less than 5 μm.

Processes for Producing an Electrochemical Cell Electrode (Anode or Cathode) Created from Carbon Scaffold-Generally Example processes for producing a three-dimensional (3D) mesoporous electrode, such as that created from lithiated carbon scaffold 400A, can include depositing (such as from one or more plasma-based thermal reactors or torches, in which thermal energy is propagated through a plasma and/or feedstock material supplied in a gaseous state) mesoporous carbon-based particles 300A or 400A to form a first contiguous film layer (such as layer 406A shown in FIG. 4A) on a substrate, where the first contiguous film layer is characterized by a first electrical conductivity. Each of the mesoporous carbon-based particles comprises electrically conductive three-dimensional (3D) aggregates or agglomerations of graphene sheets 303B. The aggregates are sintered together to form open porous scaffold 302A that facilitates electrical conduction along and across contact points of the graphene sheets. A porous arrangement formed in open porous scaffold 302A, where the porous arrangement is conducive to receive electrolyte dispersed therein for Li ion transport through interconnected pores (such as hierarchical pores 303A and/or 307F) that define one or more Li ion diffusion pathways 309F. The first contiguous film layer has an average thickness no greater than 100-200 μm. In an example, a binder material is combined with graphene sheets 303B to retain graphene sheets 303B in a desired position to impart structure to open porous scaffold 302A. The binder may be or comprise a thermosetting resin or a polymerizable monomer, wherein curing the resin or polymerizing the polymerizable monomer forms a solid resin or polymer with assistance of heat, radiation, an initiator, a catalyst, or a combination thereof. The binder may be initially a polymer, coal tar pitch, petroleum pitch, mesa-phase pitch, or organic precursor material and is later thermally converted into a carbon material.

Additional quantities of mesoporous carbon-based particles 303A and/or 400A are deposited on the first contiguous film layer to form a second contiguous film layer there-upon, the second contiguous film layer having a second electrical conductivity lower than the first electrical conductivity, and being positioned closer to electrolyte 414A and away from the current collector (which may be a sacrificial substrate).

Li ion solution can be infiltrated into (such as by capillary infusion action) open porous scaffold 302A react with exposed carbon on surfaces thereof to facilitate Li ion dissociation and electric current supply, where the exposed carbon on the open porous scaffold including a surface area greater than approximately 100 $m^2/gm$.

Processes for Producing an Electrochemical Cell Electrode (Anode or Cathode) Created from the Carbon Scaffold—In Detail Mesoporous carbon-based particles 300A and/or lithiated carbon scaffold 400A can be synthesized 'in-flight' in a microwave reactor, or deposited in a bottom-up manner, referring to a layer-by-layer deposition or "growth" within a thermal reactor, and may then be cast, via a liquid slurry to be subsequently dried to form a carbon-based electrode that may be suitable for implementation or incorporation within a Li ion battery. Such a slurry may, in some examples, comprise chemical binders and conducting graphite, along with the electrochemically active innate carbon.

The term "hierarchical", as generally understood in an engineering context and as used herein, refers to an arrangement of items in which the items are represented as being above, below, or at the same level as one another. Here, mesoporous carbon-based particle 300A and/or lithiated carbon scaffold 400A may be grown by layer-by-layer deposition in a thermal reactor to create one or more "grades" (as indicated by layers 406A to 412A of mesoporous conductive particles 300A, 302H and/or 402A), referring to that created by specific control of electrical (referring to contact points of electrically conductive interconnected agglomerations of graphene sheets 303B) and ionic (referring to Li ion diffusion pathways 309F) conducting gradients throughout the thickness of lithiated carbon scaffold 400A. Tuning of each individually deposited layer 406A through 412A results in relatively higher electrical conductivity at the current collector interface, and progressive lower electrical conductivity moving outwardly therefrom.

Electrically conductive interconnected agglomerations of graphene sheets 303B within mesoporous carbon-based particle 300A serve as both electrical conductors, by conducting electric current through contact points and/or regions, and as "active" Li intercalating structures, and therefore may be configured to provide a source for the specific capacity of the anode electrode at 744-1,116 mAh/g, such as 2-3 times that otherwise available from conventional graphite anodes at 372 mAh/g. As a result, interconnected 3D bundles of graphene sheets 102 within mesoporous carbon-based particle 100 may be considered as 'nanoscale' electrodes that concurrently enable a relatively high-volume fraction of electrolytically active material along with efficient, 3D inter-penetrating, ion and electron pathways.

This unique 3D structure of mesoporous carbon-based particle 100 enables both storage of electric charge at its exposed surfaces (via capacitive charge storage) for desirable high-power delivery, relative to conventional applications, and also provides faradaic redox ions within the bulk thereof for desirable high electric energy storage. "Redox", as generally understood and as referred to herein, refers to "reduction-oxidation" reactions in which the oxidation states of atoms are changed involving the transfer of electrons between chemical species, most often with one species undergoing oxidation while another species undergoes reduction.

"Faradaic", as generally understood and as referred to herein, refers to a heterogeneous charge-transfer reaction occurring at the surface of an electrode, prepared with, and/or otherwise incorporating mesoporous carbon-based particle 300A. For instance, pseudocapacitors store electrical energy faradaically by electron charge transfer between electrode and electrolyte. This is accomplished through electrosorption, reduction-oxidation reactions (redox reactions), and intercalation processes, termed pseudocapacitance.

Roll-to-Roll Processing for Producing an Electrochemical Cell Electrode (Anode or Cathode) Created from the Carbon Scaffold Regarding manufacturing, lithiated carbon scaffold 400A can be manufactured (to fabricate and/or build electrochemical cell electrodes, such as cathodes and/or anodes) in large-scale quantities by sequential, layer-by-layer (such as layers 406A through 412A shown in FIG. 4A) deposition of concentrations of mesoporous carbon-based particle 300A and/or 300E onto a moving substrate (such as a current collector) through a roll-to-roll ("R2R") production approach. By consolidating 3D carbon scaffold structures directly out microwave reactors (analogous to exiting plasma spray processes), electrode films can be continuously produced without the need for toxic solvents and binders that are otherwise used in slurry cast processes for battery electrodes. Therefore, battery electrodes employing lithiated carbon scaffold 400A may be more readily produced with controlled electrical, ionic, and chemical concentration gradients due to the "layer-by-layer", sequential particle deposition capabilities of a plasma-spray type processes; and specific elements (such as dopants) can also be introduced at different stages within the plasma deposition process.

Also, due to the pores 303A and/or 307F interspersed throughout mesoporous carbon-based particle 100, lithiated carbon scaffold 400A may be manufactured in a manner such that it is gravimetrically, referring to a set of methods used in analytical chemistry for the quantitative determination of an analyte based on its mass, superior to known devices. That is, mesoporous carbon-based particle 300A, with pores and/or voids defined throughout 3D bundles of graphene sheets 102 and/or conductive carbon particles 104, may be lighter than comparable battery electrodes without a mesoporous structure including various pores and/or voids, etc.

Mesoporous carbon-based particle 100 may feature a ratio of active material to inactive material that is superior relative to conventional technologies, in that greater quantities of active material are available and prepared for electricity conduction there-through relative to inactive and/or structural reinforcement material. Such structural reinforcement material, although involved in defining a general structure of mesoporous carbon-based particle 300A, may not be involved or as involved in electrically conductive interconnected agglomerations of graphene sheets 303B. Accordingly, due to its high active material to inactive material ratio, mesoporous carbon-based particle 300A may demonstrate superior electrical conductivity properties relative to conventional batteries, as well as being significantly lighter than such conventional batteries given that carbon may be used to replace traditionally used heavier metals. Therefore, mesoporous carbon-based particle 300A may be particular well-suited for demanding end-use application areas that also may benefit from its light weight include automobiles, light trucks, etc.

Mesoporous carbon-based particle 300A may be created to rely electrically conductive interconnected agglomerations of graphene sheets 303B to obtain a percolation threshold, referring to a mathematical concept in percolation theory that describes the formation of long-range connectivity in random systems. Below the threshold a giant connected component does not exist, while above it, there exists a giant component of the order of system size. Accordingly, 3D bundles of graphene electrically conductive interconnected agglomerations of graphene sheets 303B may conduct electricity from the current collector, as shown in FIG. 4A, toward electrolyte 414A.

Roll-to-Roll ("R2R") Plasma Spray Torch Deposition System

As a variation from the existing atmospheric MW plasma reactor with particle-based output, integrated, contiguous 3D hierarchical carbon scaffold films (composed of multiple mesoporous carbon-based particles 300A and/or the like agglomerated together and/or contacting to form contiguous layers, films, and/or sheets) can be constructed utilizing a spray torch configuration, such as that shown by roll-to-roll ("R2R") system 400b. Plasma torches (generally) permit for materials to be initially formulated, similar to waveguided reactor, then accelerated into an impact zone on a substrate surface (moving or stationary) wherein each zone can provide for unique control of dissimilar (mixed phase or composite) material synthesis, formulation (consolidation), and integration (densification).

The plasma torch in combination with a continuous, moving substrate enable a unique additive type of process control (such as both within the hot plasma and beyond the plasma afterglow region up to the impact zone of the substrate) of properties, such as defect density, residual stress, through thickness chemical and thermal gradients, phase transformations, and anisotropy. For the case of battery electrode fabrication, not only can the atmospheric MW plasma torch create formulated and integrated continuous 3D hierarchical mesoporous graphene films without the need for toxic solvents such as NMP and or use of binders and conductive carbons (at the very least reduction) in accordance with the slurry casting process, but the plasma torch can be used to create integrated electrode/current collector film structures for enhanced performance at a reduced cost.

FIG. 4B shows in detail roll-to-roll ("R2R") system 400b employing an example arrangement of a group 444B of plasma spray torches 422B through 428B (such as 422B, 424B, 426B, and/or 428B) configured to perform layer-by-layer deposition to fabricate, otherwise referred to as "growing", carbon-based scaffold 300H, shown in FIG. 3B, and/or variants thereof, incrementally. Group 444B of plasma spray torches 414B through 420B are oriented in a continuous sequence above the R2R processing apparatus 440B, which, may include wheels and/or rollers 434B and 439B configured to rotate in the same direction, 430B and 432B, respectively, to result in translated forward motion 436B of sacrificial layer 402B upon which layers 442B of carbon scaffold 436B may be deposited in a layer-by-layer manner to achieve a "graded" electrical conduction gradient proportionate to the concentration level of mesoporous carbon-based particles 300A contained per unit volume area in each progressive deposited layer (such as interim layers 406A-412A).

Such deposition may involve the positioning of group 444B of plasma spray torches 414B through 420B as shown in FIG. 4B, with an initial, in direction of forward motion 436B, spray torch 414B extending the furthest in a downward direction, toward sacrificial layer 404B from feedstock supply line 412B, positioned to spray 422B carbon-based material to deposit initial layer 404B (also may be shown as interim layer 406A in FIG. 4A, and so on and so forth) of carbon scaffold 300H on sacrificial layer 402B. Initial layer 404B may be deposited to achieve the highest conductivity values, with each of the subsequent layers 406B through 410B featuring a proportionately less-dense dispersion of mesoporous carbon-based particle 300A composing carbon-based scaffold 300H to achieve a 'graded' electric gradient for layers 442B.

That is, plasma spray torches 414B through 420B may be oriented to have incrementally decreasing (or otherwise varying) heights as shown in FIG. 4B, such that each spray torch from group 444B may be tuned to spray, from spray 422B to 428B, respectively, sprays of carbon-based feedstock material supplied by feedstock supply line 412B. Accordingly, battery electrodes can be more readily produced with controlled electrical, ionic, and chemical concentration gradients due to the "layer-by-layer", sequential deposition described herein with connection to plasma spray-torch system 400B, which presents desirable features of plasma spray type processes; and, specific elements or additional ingredients can also be introduced at different stages within the plasma-based spray deposition process described by plasma spray-torch system 400B. Such control may, extend to tunability of plasma spray-torch system 400B to achieve target electric field and/or electromagnetic field properties of any one or more of layers 442B.

Group 444B of plasma spray torches 414B through 420B may employ plasma-based thermally enhanced carbon spraying techniques to provide carbon coating processes in which melted (or heated) materials are sprayed onto a surface. The "feedstock" (coating precursor) is heated by electrical (plasma or arc) or chemical means (combustion flame).

Thermal spraying by plasma spray torches 414B through 420B can provide thick coatings (approx. thickness range is 20 μm or more to several mm, depending on the process and feedstock), over a large area at high deposition rate as compared to other coating processes such as electroplating, physical and chemical vapor deposition. Coating materials available for thermal spraying include metals, alloys, ceramics, plastics, and composites. They are fed in powder or wire form, heated to a molten or semi-molten state, and accelerated towards substrates in the form of μm-size particles. Combustion or electrical arc discharge is usually used as the source of energy for thermal spraying. Resulting coatings are made by the accumulation of numerous sprayed particles. The surface may not heat up significantly, allowing the coating of flammable substances.

Coating quality is usually assessed by measuring its porosity, oxide content, macro and microhardness, bond strength and surface roughness. The coating quality increases with increasing particle velocities.

Carbon Scaffold Implemented in a Li S Secondary Battery

Group 444B of plasma spray torches 414B through 420B may be configured or tuned to spray carbon-based material in a controlled manner to achieve specific desired hierarchical and organized structures, such as open porous scaffold 302A of mesoporous carbon-based particle 300A and/or 300E with hierarchical pores 307F suitable to be used for Li ion infiltration via capillary action therein dependant on percentage porosity of mesoporous carbon-based particle 300A and/or 300E. Total quantities of S able to be infused into hierarchical pores 307F and/or deposited on exposed surface regions of mesoporous carbon-based particle 300A and/or 300E (and other such similar structures) may depend on the percentage porosity thereof as well, where 3D fractal-shaped structures providing larger pores, such as pores 305F, each having dimension 103F can efficiently accommodate and micro-confine S for desired time-frames during electrochemical cell operation. Examples exist permitting for the combination of S to prevent any resultant polysulfides (PS) migrating out of pores 305F purely by designing and growing structural S, with confinement of S being targeted at a defined percentage, such as: 0-5%, 0-10%, 0-30%, 0-40%, 0-50%, 0-60%, 0-70%, 0-80%, 0-90%, and/or 0-100%, any one or more of such ranges successfully showing of retardation of polysulfide migration out of the electrode structure.

Carbon Scaffold Implemented in a Li Air Secondary Battery

Existent Li air cathodes may last only 3-10 cycles, and thus have not yet been universally understood to provide very promising or reliable technologies. In such cathodes, air itself acts as the cathode, therefore the reliable and robust supply of air flowing through the cathode, such as through pores, orifices, or other openings, effectively currently precludes realistic applications in consumer grade portable electronic devices such as smartphones.

Devices can be made with some sort of air pump mechanism, but air purification remains an issue, given that any amount of impurity prevalent in the air can and will react with available Li in parasitic side-reactions degrading specific capacity of the overall electrochemical cell. Moreover, air only provides only about 20.9% $O_2$, and thus is not as efficient as other alternative current advanced battery technologies.

Nevertheless, even in view of the above-mentioned challenges, examples provided above relating to mesoporous carbon-based particle 300A, 300E and/or any variants thereof implemented in carbon scaffold 300H and/or lithiated carbon scaffold 400A can be configured to function in a 3D-printed battery. Notably, measures can be taken to guard against, such as by tuning to achieve desirable structural reinforcement in certain targeted areas of open porous scaffold 302A, to prevent against unwanted and/or sudden collapse of porous structures, such as to create 'clogging' of passageways defined therein. In example, carbon scaffold 300H can be decorated with a myriad of metal oxides to achieve such reinforcement, which may also control or otherwise positive contribute to mechanical tunnelling of the structure itself once lithium reacts with air to spontaneously form a solid from that state, etc. Traditional circumstances (such as absent special preparations undertaken regarding implementation of the disclosed mesoporous carbon-based particle 300A and/or the like with Li air cathodes) can otherwise involve Li ions reacting with carbon provided in a gaseous state, such that the Li ion and the carbon-containing gas react to form a solid that expands. And, depending on where this expansion occurs, can mechanically degrade the overall carbon-based mesoporous scaffold structure, such as of carbon scaffold 300H.

Pre-Lithiation of 3D Mesoporous Carbon-Based Particle as a "Host"

To enable alternative non-lithium or lithiated carbon-based scaffolded cathodes, such as those confining sulfur, oxygen, and vanadium oxide, over current lithium oxide compound cathodes, as well as to accommodate first charge lithium loss (resulting reduced coulombic efficiency) in current lithium-ion cells, a scalable pre-lithiation method for carbon-based structured intended for implementation in electrochemical cell electrodes may be required. As a result, various experimental attempts have been conducted with mesoporous carbon-based particle 300A,300E and/or any derivative structures based therefrom, including carbon scaffold 300H such as ball milling, post thermal annealing, and electrochemical reduction from an additional electrode. Such efforts have been used to "pre-lithiate", referring to chemically preparing a carbon-based structure to react with and/or confine lithium physically and/or chemically, but have met with uniformity, lithium reactivity, costs, and scalability challenges.

Nevertheless, by fine-tuning reactor process parameters, 3D mesoporous carbon-based particle 300A, 300E, and/or carbon scaffold 300H may be synthesized and/or fabricated by layer-by-layer deposition process, as substantially discussed earlier, to serve as a carbon-based 'host' structure with engineered surface chemistry (such as including nitrogen and oxygen doping) to facilitate rapid decomposition (involving disproportionation of oxides).

Upon thermal (referred to herein as "spark") activation, Li metal can be spontaneously (such as without a pressure gradient) and non-reactively infiltrated (driven by capillary forces) to create a controlled, pre-lithiated carbon structure (or particle building blocks). Subsequently, such "pre-lithiated" particle building blocks can be synthesized into an integrated composite film with graded electrical conductivity from:

(1) a high conductivity at a back plane in contact with the current collector (such as shown by interim layer 406A, to
(2) an insulated ion conducting layer at the electrolyte/electrode plane.

Surface chemistry, as may be related to non-reactive infiltration of Li metal can be tuned by optimizing oxide thermal reduction degree (exotherm) by using thermogravimetric analysis (TGA) or differential scanning calorimetry DSC analytical techniques.

To address scalability concerns as may be related to transitioning from a low-volume laboratory testing and sample production environment, to a high-volume large-scale plant capable of fulfilling multiple customer orders simultaneously, the above described "pre-lithiation" process is readily adaptable to a continuous roll-to-roll (R2R) format, analogous to other liquid melt wetting processes such as brazing.

Thin film lithium clad foil (tantalum or copper) can be loaded onto a heated calendaring roll, to be brought into contact with 3D mesoporous carbon-based particle 300A and/or the like pre-form (or carbon film, in the case of the spray torch process) in a controlled thermal, dry environment. Thermal residence (soak) time, gradient, and applied pressure can adjusted and controlled to facilitate both: (1) "spark" activation; and (2) infiltration process steps.

"Spark" Lithiation of the Carbon Scaffold

Historically, prior to the development of Li metal infusion methods into carbon-based structures and/or agglomerate particles, efforts were undertaken to assess the following two scenarios:

(1) growing microwave graphene sheets that have extended de-spacing that would allow intercalation to occur in-between individual graphene sheets at a much more efficient or a faster rate than what would occur in typical, commercially-available, graphene sheets; and, growing FLG in such a way to successfully and repeatably achieve such higher de-spacing; and
(2) using a wet liquid Li metal front that propagates into hierarchical pores 303A and/or 307F defined by open porous scaffold 302A of 3D mesoporous carbon-based particle 300A and/or 300E. Attraction from Li metal to exposed carbon-based surfaces wet the same in an efficient way relative to otherwise performing functionalization on exposed carbon-based surfaces.

Presently disclosed examples relating to thermal reactors further provide for capabilities for post processing to create highly organized and structured carbons that have that particular functioning relating to the infiltration of metal and/or other species, such as infiltration of aluminium into a silicon carbide-sintered material, and hammering the surface of the particles to promote infiltration of a molten (Li) metal front without additional pressure from outside sources. Such efforts permit for continuous wetting instead of using pressure to push metal into open porous scaffold 302A of 3D mesoporous carbon-based particle 300A and/or 300E.

FIG. 4A shows a schematic representation of agglomerations or aggregations of 3D mesoporous carbon-based particles 402A, akin to 3D mesoporous carbon-based particles 300A and/or 300E, synthesized or deposited at varying concentration levels in layers 406A to 412A, from most concentrated to least concentrated. All layers 406A through 412A, subsequent to creation, can be infiltrated, via non-reactive capillary infusion methods, with Li metal and/or Li ion solution in liquid state or phase for intercalation of Li ions in-between individual graphene sheets of electrically conductive interconnected agglomerations of graphene sheets 303B of 3D mesoporous carbon-based particle 300A, which may be created with a spacing of 1 to 3 Å to accommodate more Li ions between alternating graphene sheets when compared to conventional commercially available graphene sheet stacks.

Voids (referring to vacant regions or spaces) between adjacent and/or contacting mesoporous carbon-based particles 300A and/or 300E composing any one or more of layers 406A-412A of lithiated carbon scaffold 400A may be encased or at least partially covered by, at a section of lithiated carbon scaffold 400A positioned away from the current collector and facing the electrolyte, a passivation layer. Such a passivation layer refers a material becoming "passive," that is, less affected or corroded by the environment of future use. In addition, or in the alternative, an ion conduction (insulating) or graded interphase layer can be deposited on layer 412A facing electrolyte 414A to minimize side reactions with free and/or unattached (physically and/or chemically) Li in ionic form. Prior to the deposition or placement of any such encasing layer, lithium, in the form of Li ions, may be flowed in liquid state into hierarchical pores 303A and/or 307F of open porous scaffold 302A of any one or more of mesoporous carbon-based particles 300A and/or 300E composing layers to form electrochemical gradients proportionate to the level of concentration of mesoporous carbon-based particles 300A and/or 300E composing each layer of layers 406A-412A, layer 406A having the highest concentration of mesoporous carbon-based particles 300A and/or 300E permitting for relatively high levels of electric current conduction between electrically conductive interconnected agglomerations of graphene sheets 303B. Layers 408A-412A (and additional such layers, if necessary or desirable) each have progressively lower (sparser) concentration levels of mesoporous carbon-based particles 300A and/or 300E, thus correspondingly having proportionately lower levels of electric conductance capabilities.

Repeated (cyclical) li ion electrode usage in secondary batteries can result in problems due to metal formation, such as volume expansion during re-depositing in electroplating operations (referring to a process that uses an electric current to reduce dissolved metal cations so that they form a thin coherent metal coating on an electrode). The term can also be used for electrical oxidation of anions on to a solid substrate, as in the formation of silver chloride on silver wire to make silver/silver-chloride electrodes. Electroplating is often used to change the surface properties of an object (such as abrasion and wear resistance, corrosion protection, lubricity, aesthetic qualities), but may also be used to build up thickness on undersized parts or to form objects by electroforming.

Processes used in electroplating with relation to infiltration of Li ion solution into lithiated carbon scaffold 400A may be referred to as electrodeposition (also known as electrophoretic deposition (EPD)) and is analogous to a concentration cell acting in reverse. Electrophoretic deposition (EPD) is a term for a broad range of industrial processes which includes electrocoating, cathodic electrodeposition, anodic electrodeposition, and electrophoretic coating, or electrophoretic painting. A characteristic feature of this process is that colloidal particles suspended in a liquid medium migrate under the influence of an electric field (electrophoresis) and are deposited onto an electrode. All colloidal particles that can be used to form stable suspensions and that can carry a charge can be used in electrophoretic deposition. This includes materials such as polymers, pigments, dyes, ceramics, and metals.

Electroplating, as described above, with Li ions may result in a volume expansion as significant as approximately 400% or more of lithiated carbon scaffold 400A. Such an expansion is undesirable from a stability standpoint micromechanically and causes degradation with many "dead zones", referring to inactive or non-chemically and/or electrically activated regions, therefore ultimately preventing the derivation of longer lifespans out of so-equipped Li ion batteries. In any case, it is desirable to have a majority of the Li ion material plate, meaning reduce onto a smooth and uniform surface to therefore facilitate uniform deposition of Li ions. Removal will also be smooth in a smooth planar interface.

Layers 406A-412A, experimentally, have been found (in an example) to have interfacial surface tension, $\gamma_{sl}$, engineered to promote wetting of exposed carbon-based surfaces with Li ion. In an example, layer 406A may be defined as having low-ion transport, high electrical conductivity, low electrical resistance (<1,000Ω); whereas layer 412 (facing electrolyte 414A) may be defined as having high-ion transport, low electrical conductivity, and high electrical resistance (>1,000-10,000Ω).

In practice, Li, (when infiltrated into lithiated carbon scaffold 400A) may tend to form unwanted dendrites, defined as crystals that develop with a typical multi-branching tree-like form. Dendritic crystal growth may be, in certain circumstances, illustrated (in example) by snowflake formation and frost patterns on a window. Dendritic crystallization forms a natural fractal pattern. Functionally, dendritic crystals can grow into a supercooled pure liquid or form from growth instabilities that occur when the growth rate is limited by the rate of diffusion of solute atoms to the interface. In the latter case, there must be a concentration gradient from the supersaturated value in the solution to the concentration in equilibrium with the crystal at the surface. Any protuberance that develops is accompanied by a steeper concentration gradient at its tip. This increases the diffusion rate to the tip. In opposition to this is the action of the surface tension tending to flatten the protuberance and setting up a flux of solute atoms from the protuberance out to the sides. However, overall, the protuberance becomes amplified. This process occurs again and again until a dendrite is produced.

Such Li ion dendrites (also in the form of acicular Li ion dendrites, "acicular" describing a crystal habit composed of slender, needle-like crystal deposits) grow away from surfaces upon which Li ions are infiltrated (such as upon and/or in-between individual graphene sheets 303B). In some circumstances, with enough battery charge-discharge cycling, a dendritic protrusion or protuberance will grow across all the way through the cathode and "short" it out, describing when there is a low resistance connection between two conductors that are supplying electrical power to a circuit. This may generate an excess of voltage streaming and cause excessive flow of current in the power source. The electricity will flow through a "short" route and cause a "short" circuit.

Employing any one or more of the advanced capillary Li ion infusion techniques (to be described in further detail herein) into lithiated carbon scaffold 400A addresses many of the described shortcomings, inclusive of traditional Li ion battery cathode specific capacity. An issue encountered in Li ion batteries is that the cathode provides only a limited quantity of specific capacity or energy capability; moreover, on the anode side, decreases have also been observed in specific capacity and energy density as well. Thus, even in view of how relatively desirable (in terms of electric energy storage capacity and current delivery) a Li ion battery may be compared to Li metal hydride or lead-acid, or Ni Cad batteries (providing energy storage density figures a factor of 2-3 greater than any one of those traditional battery chemistries), even greater advancements in electric power storage and delivery are possible, regarding the protection against or prevention of unwanted Li-based dendritic formations, upon the incorporation of carbon-based materials, such as that disclosed by the present examples, and approaches theoretic capacities (not attained in practice), of pure Li metal, which has a specific capacity of around 3,800 mAh/g.

Other approaches have been undertaken including the development of solid-state batteries, describing no liquid phases at all. However, attention has returned to Li metal, due to oxide electrolyte being used to achieve and stabilize contact with Li. And alternatives to Li metal have also been explored including Si, Sn, and various other alloys. However, even upon elimination of Li metal, a Li ion source may still be required (as originated from an opposing side of the battery device.)

Alternative-to-lithium materials in a Li ion battery electrode structure may yield the following energy density values: oxides provide 260 mAh/g; and, sulfur provides 650 mAh/g. Due to its relatively high energy density capabilities, it is desirable in battery electrode applications to confine sulfur (S), so it is not solubilized or dissolved into surrounding electrolyte. To that effect, sulfur micro-confinement is needed (as described earlier in relation to pores 305F of open porous scaffold 302A), describing that a "confined" (or "micro-confined") liquid is a liquid that is subject to geometric constraints on a nanoscopic scale so that most molecules are close enough to an interface to sense some difference from standard bulk conditions. Typical examples are liquids in porous media or liquids in solvation shells.

Confinement (and/or micro-confinement, referring to confinement within microscopic-sized regions) regularly prevents crystallization, which enables liquids to be supercooled below their homogenous nucleation temperature (even if this is impossible in the bulk state). This holds in particular for water, which is by far the most studied confined liquid.

Thus, in view of the various challenges presented above, and others not discussed here, various improvements to traditional graphite-based anodes may be achieved by instead employing few layer graphene (FLG) materials and/or structures, defined as having less than 15 layers of graphene grown, deposited or otherwise organized in a stacked architecture with Li ions intercalated there-between at defined interval and/or concentration levels. Any one or more of mesoporous carbon-based particle 300A, 300E and/or the like may be so prepared.

Doing so (going from graphite to FLG) may improve specific capacity from approximately 380 to over a 1,000 mAh/g for Li-intercalated carbon-based structures. Disclosed materials can replace graphite with FLG to permit for a higher active surface area and can increase spacing in-between individual graphene layers for infiltration of up to 2-3 Li ions, as opposed to just 1 Li ion as commonly may be found elsewhere.

In graphene, hexagonal carbon structures in each graphene sheet may stay positioned on top of each other—this is referred to as an "A-A" packing sequence instead of an "A-B" packing sequence. Particularly, configurations are envisioned for graphene sheets and/or FLG where individual layers of graphene may be stacked directly on top of each other, to obtain incommensurate, disproportionate and/or otherwise irregular, stacking, which in turn permits for the intercalation of addition Li ions in-between each graphene layer of FLG structures.

Under traditional conditions and circumstances, the insertion of Li ions from, the top-down or bottom-up in layered graphene structures may prove exceedingly difficult in practice. Comparably, Li ions more easily insert in-between individual graphene layers (separated by a definable distance). Thus, the key is to manage and tune exactly how much edge area is available. In that regard, any of the carbon-based structured disclosed herein are so tuneable. And carbon in graphene is also conductive-therefore, this feature provides for dual-roles by: (1) providing structural definition to FLG scaffold electrode structures (such as carbon scaffold 300H and/or lithiated carbon scaffold 400A); (2) and conductive pathways therein.

Production techniques employed to fabricate any one or more of the carbon-based structures disclosed herein may indicate a desirability of adjustment of individual graphene-layer edge lengths relative to planar surfaces thereof; also, the adjustment of the spacing in between individual graphene stacks may be possible. Graphene, given its two-dimensional structure, necessarily provides significantly more surface area in which Li ions can be inserted. Thus, applying graphene sheets in accordance with various aspects of the subject matter disclosed herein may provide a natural evolution in the direction of enhanced energy storage density.

Individual graphene sheets are held in position as a part of the plasma growth process. Carbon based "gumball-like" structures are self-assembled in-flight (as described earlier) from FLG and/or combinations of to form particles (such as mesoporous carbon-based particle 300A and/or the like) somewhat but with a defined long-range order defined generally and herein as where solid is crystalline if it has long-range order-once the positions of an atom and its neighbors are known at one point, the place of each atom is known precisely throughout the crystal, to it-smaller structures agglomerate to form essentially what resembles a gumball.

Size dimensions of such "gumball-like" structures (describing individual mesoporous carbon-based particles 300A and/or the like) may be about 100 nm across (at its widest point). Larger agglomerated particles made up from multiple "gumball-like" structures may be an order of magnitude larger, about 20-30 microns in diameter.

These "gumball-like" structures (individual mesoporous carbon-based particles 300A and/or the like) may comprise of multiple FLG structures (electrically conductive interconnected agglomerations of graphene sheets 303B) with Li ions interspersed there-within, at a level of 2-3 Li ions in-between each individual graphene layer (made possible by the tuning of the height or gap length between individual graphene layers) tied into a carbon scaffold gradient by joining the larger 3D graphene-based particles together to form a thin film.

In contrast, traditional battery electrode production methods typically employ known deposition techniques such as chemical vapor deposition (CVD) or other fabrication techniques, nanotubes, etc., to "grow" structures off a defined fixed substrate or surface. Such known assembly processes and procedures can tend to be very labor intensive, and they may also permit for the growth of structures of limited thickness, 200-300 microns in thickness.

Graphene-on-graphene densification, of multiple FLG, on an original gumball-based carbon scaffold (individual mesoporous carbon-based particles 300A, carbon scaffold 300H, lithiated carbon scaffold 400A, and/or the like) may also result in increased energy density and capacity. Such densification in target regions of the carbon scaffold may also be performed or otherwise accomplished after creation of a larger agglomerated particle comprising multiple mesoporous carbon-based particles 300A. Li ions may be plated onto electrode prior to reduction; therefore, Li ion may transition from an ion to a metal state dependent on battery chemistry. Moreover, in an implementation, like electroplating, graphene may be grown in a stacked manner on other materials, such as plastic, and tuned to obtain a desirable bright and/or smooth finish. Such electroplating processes are reversible and may include separate but interrelated plating process and a stripping process, intended to place the Li ions and/or atoms down (and for the subsequent removal thereof).

In continual cyclical use of secondary Li ion batteries, involving multiple charge-discharge-recharge cycles, surfaces upon which carbon-based structures are grown and/or built may eventually roughened and therefore susceptible to or accommodative of unwanted dendrite growth. In contrast, techniques employed to produce mesoporous carbon-based particles 300A and/or the like, as discussed above, prevent such dendrites from growing, enabled by the usage of Li metal substantially free of impurities along with carbon-based graphene structures to enable high specific capacity values.

Usage of graphene sheets permits for greater exposed surface area available for plating or intercalating operations for the infiltration (referring to non-reactive capillary infusion) of Li ions. Thus, any tendency to go to a certain point anymore is removed; and, fundamentally the way plating and stripping occurs may be changed (due to the graphene having a higher surface-area to volume ratio than other conventional carbon-based materials such as graphite). Li ions may be introduced at least partially relying upon liquid Li; however, given Li's predisposition for chemical reactivity with surrounding and/or ambient elements, water-based moisture and oxygen must be kept away. Similarly, the introduction of impurities results in deleterious effects. Metal-matrix composites have been studied, in relation to the disclosed carbon-based structures, regarding usage of Li metallically bonding or otherwise forming a metal-matrix composite with C, therefore offering additional options regarding the fine-tunability and management of reactivity at exposed surfaces.

Li in contact with C may result in circumstances where the free energy of carbide of Li at contact surfaces must be suppressed and/or controlled to avoid unwanted reactivity related to spontaneous Li infiltration in mesoporous carbon-based particle 300A and/or the like. Traditionally, Li, in a liquid phase, typically forms carbonates and other formations due to the chemistry of the electrolyte. However, what is proposed by the present examples relates to the creation of a stable solid electrolyte interface (SEI) prior to the introduction of the liquid electrolyte, this is a central concept supportive of the surprising performance success of the disclosed examples and implementations.

Moreover, multiple methods and/or processes to affect Li ion interface areas may be available. For instance, preparing the surface of liquid Li by alloying with Si and other elements will reduce the reactivity and promote overall Li ion wetting of larger agglomerated particles, each comprising multiple "gumball" structures (mesoporous carbon-based particles 300A). In an example, less than 1.5% of Li was observed to have preferentially moved to exposed surfaces, exposed to the electrolyte.

Figure 5A:
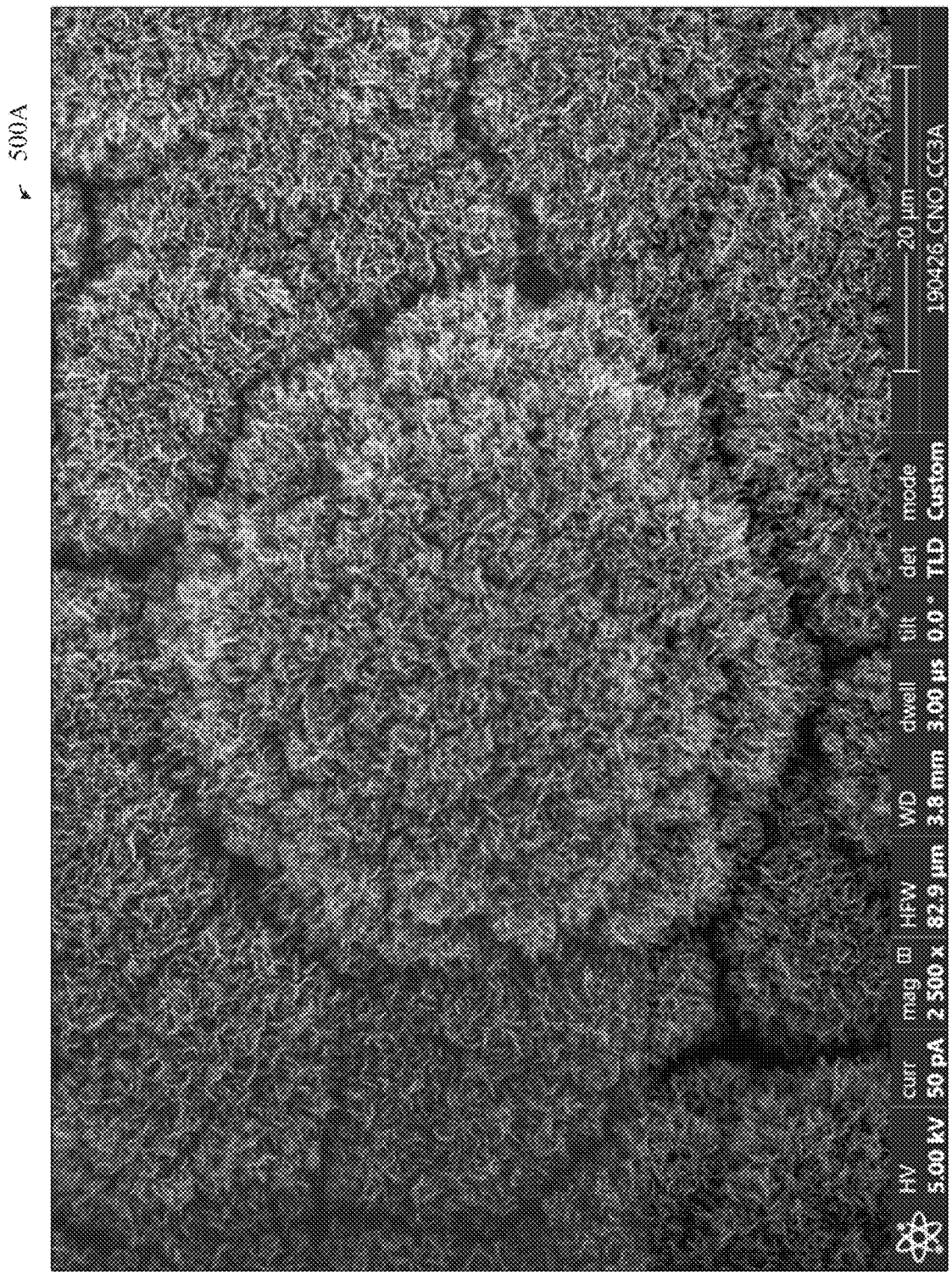
FIGS. 5A-5B show various photographs and/or micrographs related of example variants of the 3D mesoporous carbon-based particles shown herein.
Figure 5B:
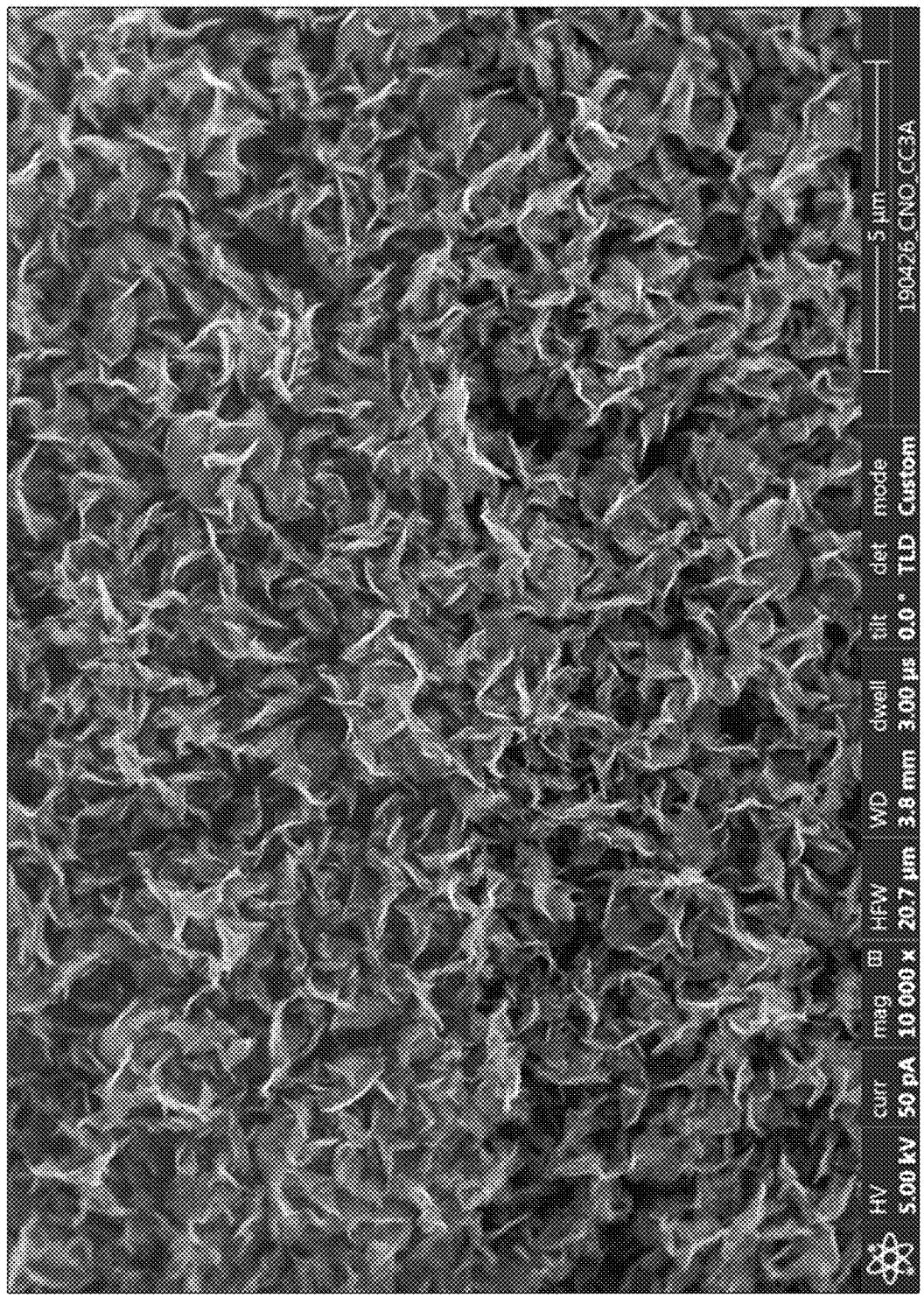
Figure 7A:
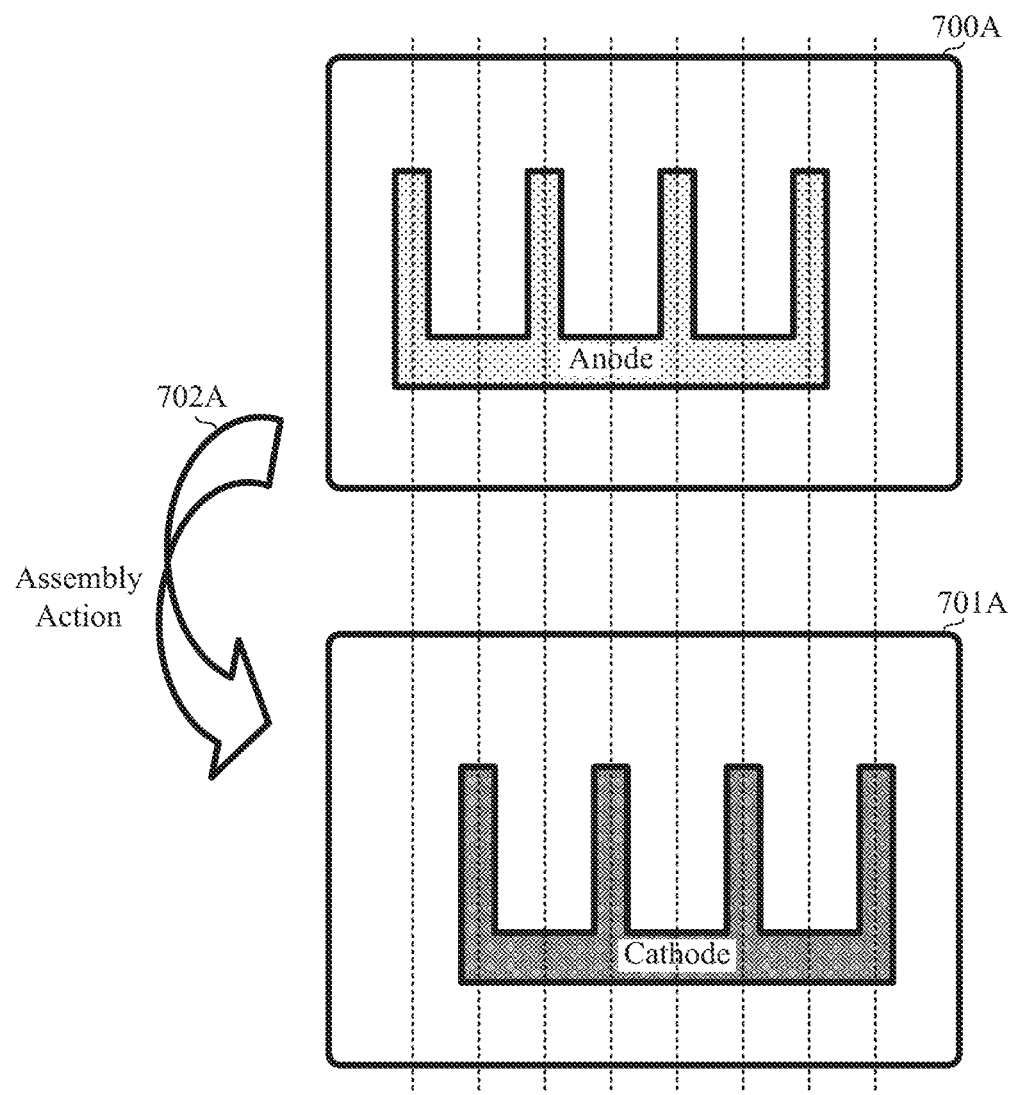
Figure 8A:
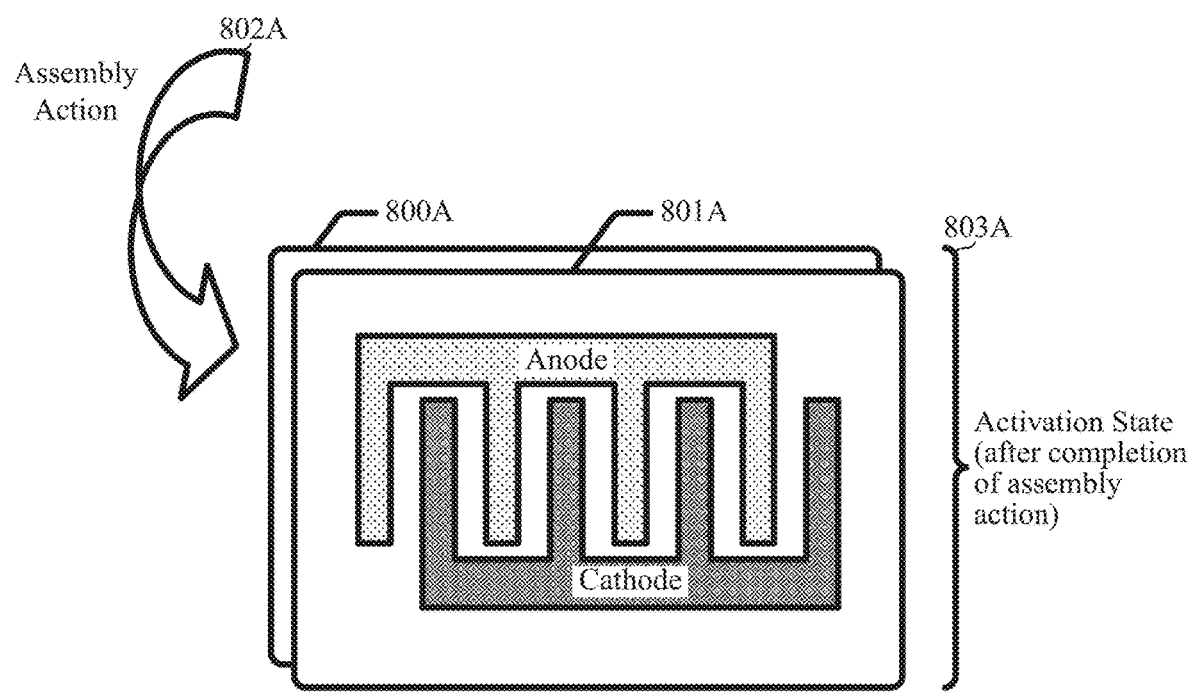

FIGS. 5A-5B show various photographs and/or micrographs related of example variants of the 3D mesoporous carbon-based particles shown in FIGS. 3A-3J. FIGS. 5A-5B show various photographs and/or micrographs related of example variants (variant 500A and variant 500B) of the 3D mesoporous carbon-based particles shown in FIGS. 3A-3J at various magnification levels illustrating internal porosity and microstructure. As can be seen from variant 500A, mesoporous carbon-based particle 300A, 300E and/or the like self-assembles upon an initial nucleation, such as in-flight in a microwave plasma-based reactor (as discussed earlier) to form ornate scaffolded agglomerations such as carbon scaffold 300H suitable for lithiation to become lithiated carbon scaffold 400A.

FIGS. 5C1-5C3 show examples related to a printed battery featuring pressure-based electrolyte release capabilities. The present batteries utilize a metal air battery chemistry, illustrated by FIG. 5C1-5C3, which includes an air (cathode) electrode reaction and a metal (anode) electrode reaction. The batteries include a dry carbon electrode with embedded conducting salt (such as ionic liquid), where the carbon is activated when exposed to moisture in the air. The active metal anode may be made of, for example, Mg, Zn, Al or other metals, and may or may not include a carbon-based material. In one implementation, Mg alloy is used for the anode because of its benign biological function and high theoretical capacity.

In some implementations, biocompatible conductive polymers, such as Polypyrrole (PPy) could be used in combination with carbons and specific oxygen reduction catalysts to create a composite cathode material that is biocompatible. For the anode, the approach is to use bio-compatible/biodegradable materials such as Mg, Zn, Al, and the like and as a separator, cellulose and polymer-based materials would be used. Management of toxicity, biocompatibility and biodegradability can be controlled as independent variables.

The cathode may be made of, for example, graphite, silver chloride, copper chloride, $MnO_2$, or carbon/$MnO_2$ in the case of a supercapacitor. In some implementations, the carbon electrode may include an electrocatalyst to accelerate the reaction. In such implementations, the carbon electrode surface can be functionalized to absorb $CO_2$ in the air, to prevent the $CO_2$ from blocking the electrode reaction. This is because $CO_2$ in the air could undergo a carbonation reaction with the electrocatalyst (such as alkaline electrolyte), thus changing the reaction environment inside the cell, blocking the gas diffusion layer and limiting access of air by the battery.

In some implementations, the battery includes hydrophobic and/or hydrophilic areas to inhibit and promote wetting and infiltration spatially across the surface. For example, carbon-based materials can be tailored to be hygroscopic (such as hydrophilic) for use within the electrodes so that when the battery is exposed to air, adsorption of water from the air activates the electrode materials. In another example, carbon-based materials can be tailored to be hydrophobic to form a barrier around the battery so that the electrolyte, when activated by moisture, will stay within the battery area of the substrate. The tailoring of the carbons to be hydrophobic or hydrophilic can be achieved by, for example, altering the surface energies of the carbon. In some implementations, this tailoring may be achieved in the reactor when the carbon particles are produced, creating a surface layer that is stable in air.

In a specific example of electrode materials, shown in FIGS. 1A-1B, the anode is a metal-doped carbon such as metal/graphite. The bulk of the anode, such as a central area, is hydrophilic, such as with a specifically tailored carbon-based material. When the anode is exposed to air, moisture in the air is adsorbed onto the anode thereby activating the anode. The cathode can be an air cathode that operates using functional carbon, particularly its porous and conductive properties. The carbon serves as a gas diffusion layer, controlling diffusion of water and carbon dioxide across the carbon layer. The cathode has an embedded electrolyte and a catalyst that are activated when water is introduced. The electrodes are surrounded by a hydrophobic perimeter, which serves as a dam to prevent the activated materials from spreading to other areas. The perimeter can be made from, for example, carbon that is tailored to be hydrophobic.

In some implementations, the electrolyte may be an ionic conductor and may be a semi-solid or gel-type compound embedded in a liquid. The liquid may be, for example, aqueous graphite (with electrochemical window, such as 1.3 V), an organic liquid, or a dry ionic liquid (4-6 V window). The electrolyte may be activated with a hygroscopic additive or with an ionic liquid bound to a polymer (such as polypyrrole) in the carbon air cathode.

In some implementations, nanoscopic active materials such as $MnO_2$ or hydrogen (for the cathode), can be incorporated directly onto or into the surface of nanostructured carbons. In such a configuration, the nanostructured carbon substrate serves a high-surface-area, 3-D current collector for a coating (such as $MnO_2$) and defines the internal pore structure of the electrode, which facilitates the infiltration and rapid transport of electrolyte to a nanoscopic $MnO_2$ phase.

The battery components are fabricated by printing, which may include a binder. Examples of printing materials include chitosan for aqueous liquids (embedded chlorine nitrate is biodegradable) and ionic liquids. Carboxymethyl cellulose (CMC) is an example an organic electrolyte. An example of a material for the current collectors is a metal laminated plastic with a thin graphite layer to reduce contact resistance to electrode materials.

The printed batteries of the present implementations are compatible with high-volume, roll-to-roll manufacturing processes such as gravure and screen printing. Thus, the present printed batteries may be economically produced.

Applications

The printed batteries can be used, for example, in short-term (duty cycle), single-use events needing a safe, "throw-away" power requirement. Example applications include using the printed battery as a power source for smart tags, tracking labels for boxes/packaging (such as a multi-day international package delivery), electronic accessories to be powered for a limited time (such as a display for notebooks), and consumer products on a retailer's shelf (such as for inventory control). Additional examples include entertainment applications, such as "smart" concert tickets, greeting cards, and toys. In other examples, the biodegradable (such as biocompatible) nature of the batteries enable their use as a power source for medical applications, such as drug delivery. Applications with larger available footprints will typically enable more usable amounts of power to be generated.

Another application of the present printed batteries is that the process of activating battery can also provide an opportunity for analysing contaminants or hazardous materials that may have been transferred from a user's skin to a sensor connected to the battery.

Yet other myriad applications of the present printed batteries are apparent. For example, the present printed batteries can be used in medical devices. Moreover, applications of the present printed batteries arise when used in subcutaneous medical devices, and since medical devices are often stored for relatively long periods of time before being used in vivo, there are number advantages of using the two-part aspects of the batteries described herein. As strictly one example advantage, the two-part batteries can be stored for long periods of time before being activated (such as when being dispensed to a patient). This feature results in medical devices that have reliably long usability. Strictly as one example, so long as the battery materials do not contact with moisture or a 'liquid' electrolyte (such as so long as the individual battery components are not activated), the individual separate components have an expected "shelf life" (such as usable life in un-activated state) of greater than 5 years.

The biodegradability of a component or combination of components depends on the specific chemistries in use. In some cases, the materials and chemistries are preferentially selected to be biocompatible, independent of biodegradability. The bio-compatibility aspects as well as biodegradability aspects of a particular battery option can be engineered in accordance with the specific requirements of a specific end-use or specific application.

FIG. 6A-6C shows views of a printed battery that can be activated at a point-of-use.

FIGS. 7A-8A show self-aligning geometry that self-aligns even in presence of lateral misregistration.

FIG. 8B shows an example listing of printed battery properties and advantages.

Figure 9:
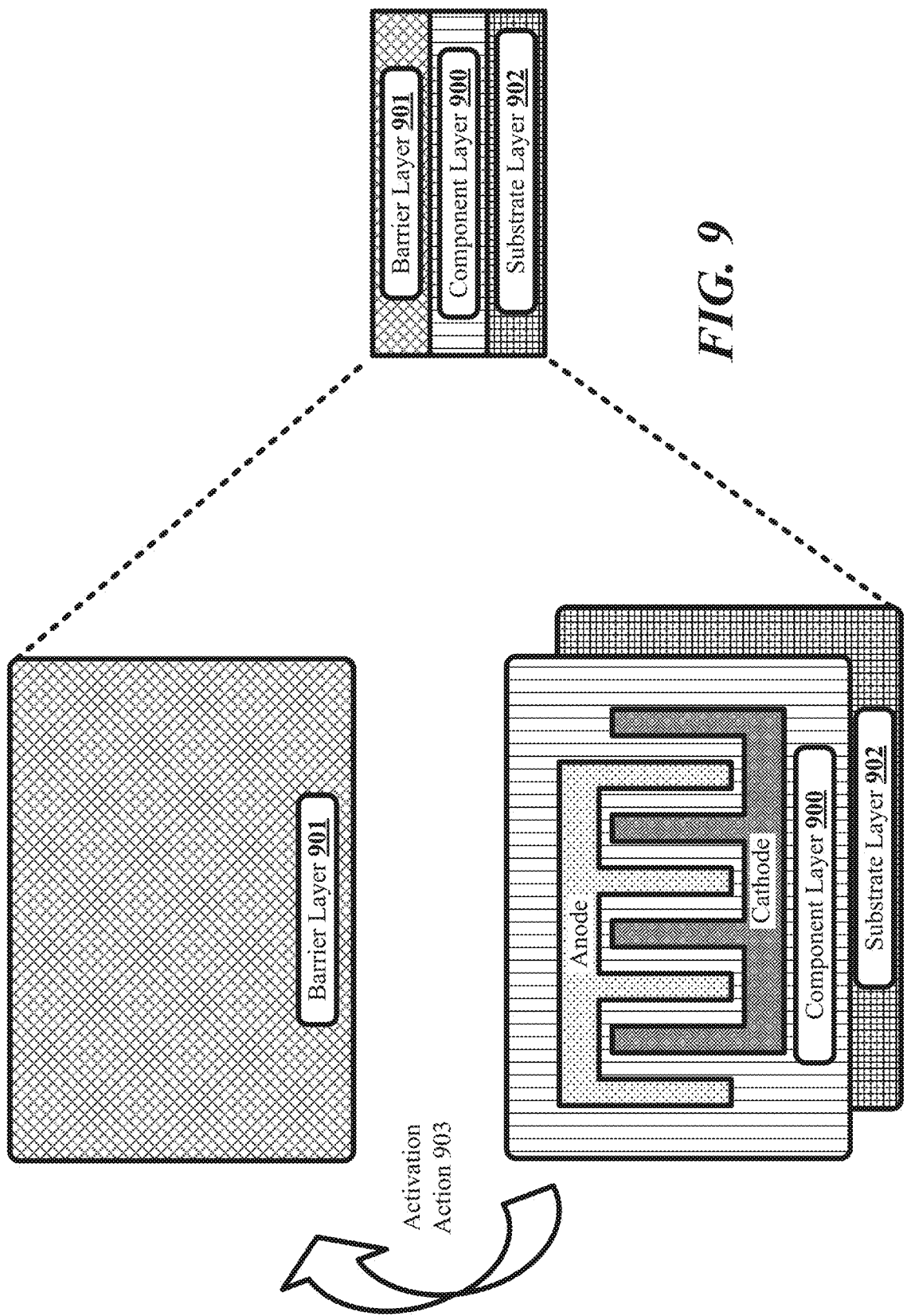
FIG. 9 illustrates a configuration of an anode and cathode interdigitated therewith, both the anode and cathode being disposed on a component layer, which is disposed on a substrate layer.

FIG. 9 illustrates a configuration of an anode and cathode interdigitated therewith, both the anode and cathode being disposed on a component layer, which is disposed on a substrate layer.

Figure 10:
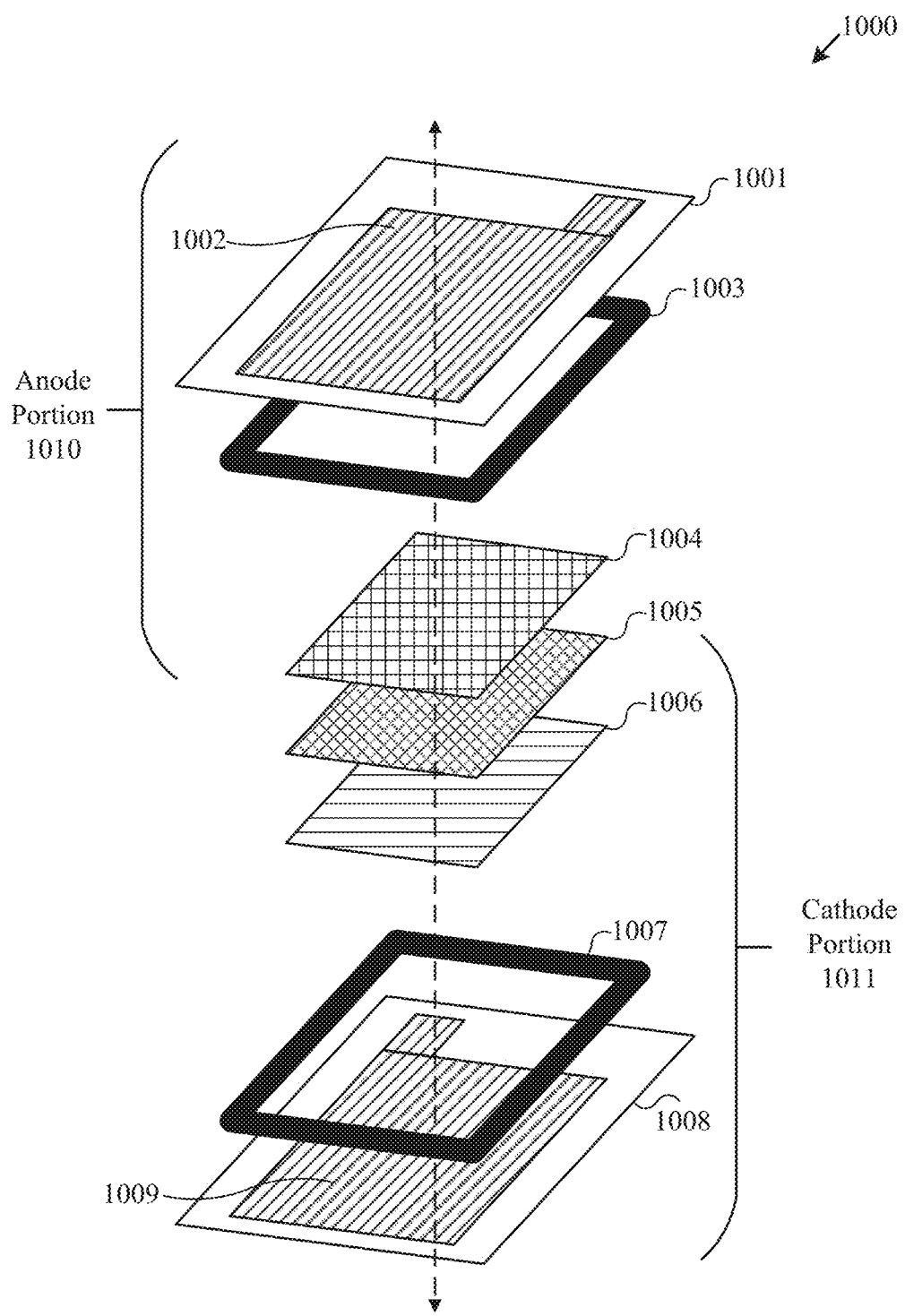
FIG. 10 an exploded view of layers of an example printed battery, such layers including elements of a cathode and anode portion, respectively.

FIG. 10 an exploded view of layers of an example printed battery, such layers including elements of a cathode and anode portion, respectively.

Figure 11:
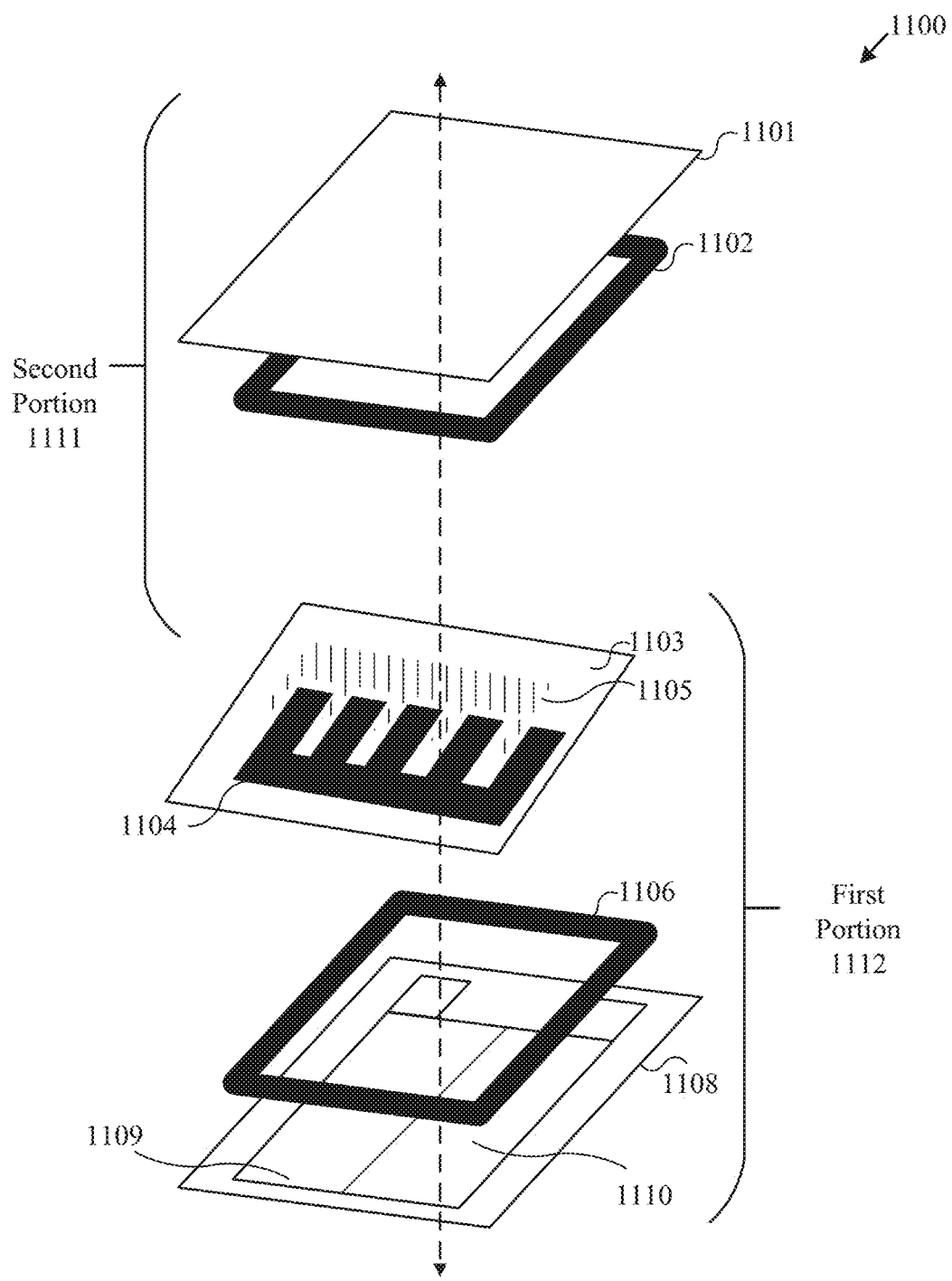
FIG. 11 an exploded view of layers of an example printed battery, such layers including elements of a cathode and anode portion, respectively.

FIG. 11 an exploded view of layers of an example printed battery, such layers including elements of a cathode and anode portion, respectively.

Figure 12A:
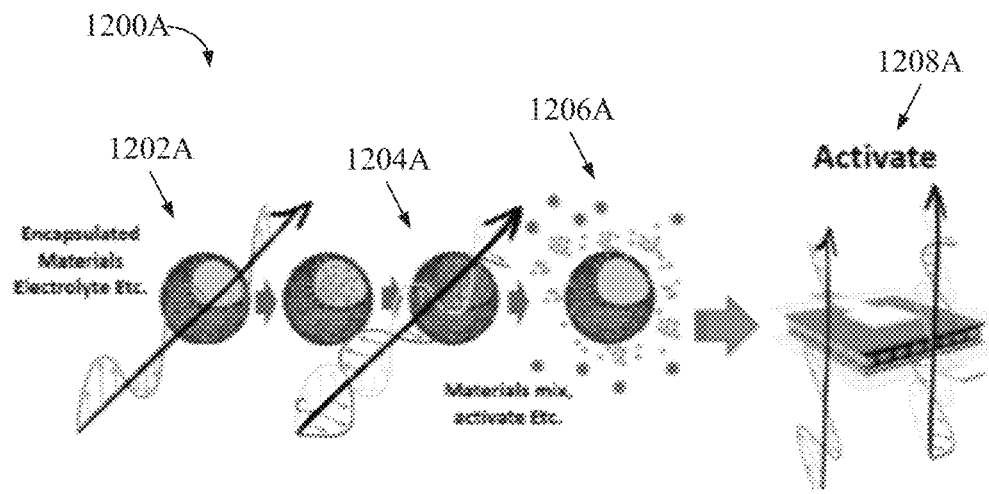
FIGS. 12A-12B show an example where printed batteries are activated by an external source.
Figure 12B:
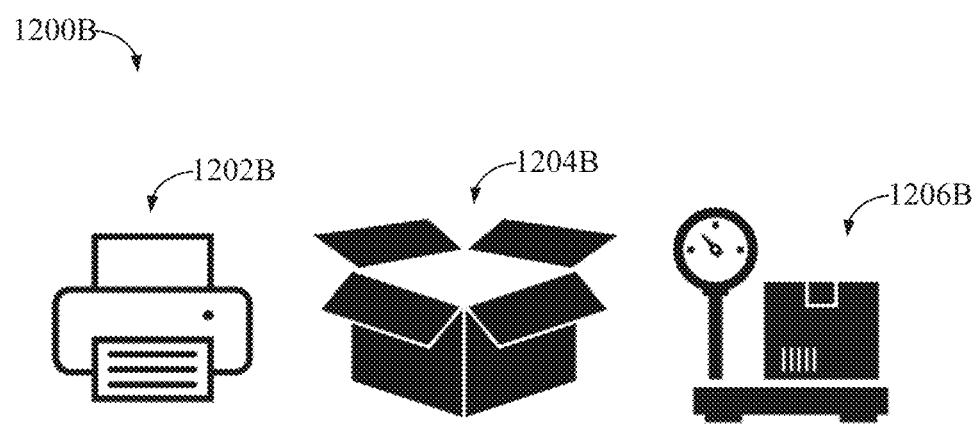
Figure 12C:
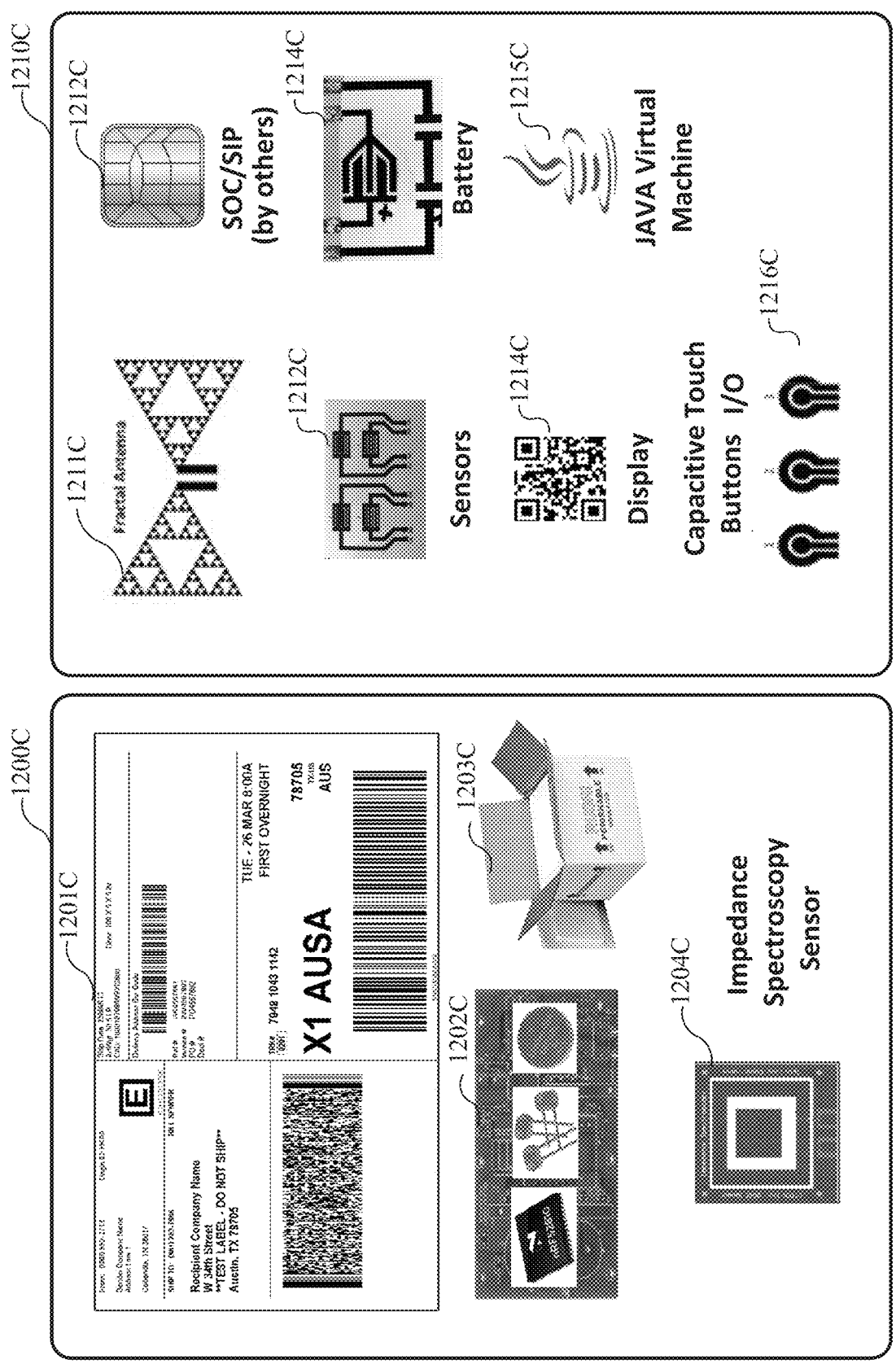
Figure 14:
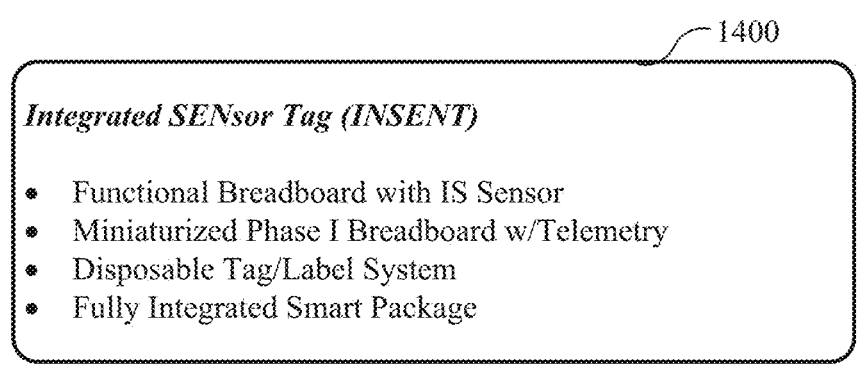

FIGS. 12A-12B show an example where printed batteries are activated by an external source.

FIGS. 12C-18 show information, targets, properties, and related materials for printed batteries according to a variety of examples of the presently disclosed implementations.

Figure 19A:
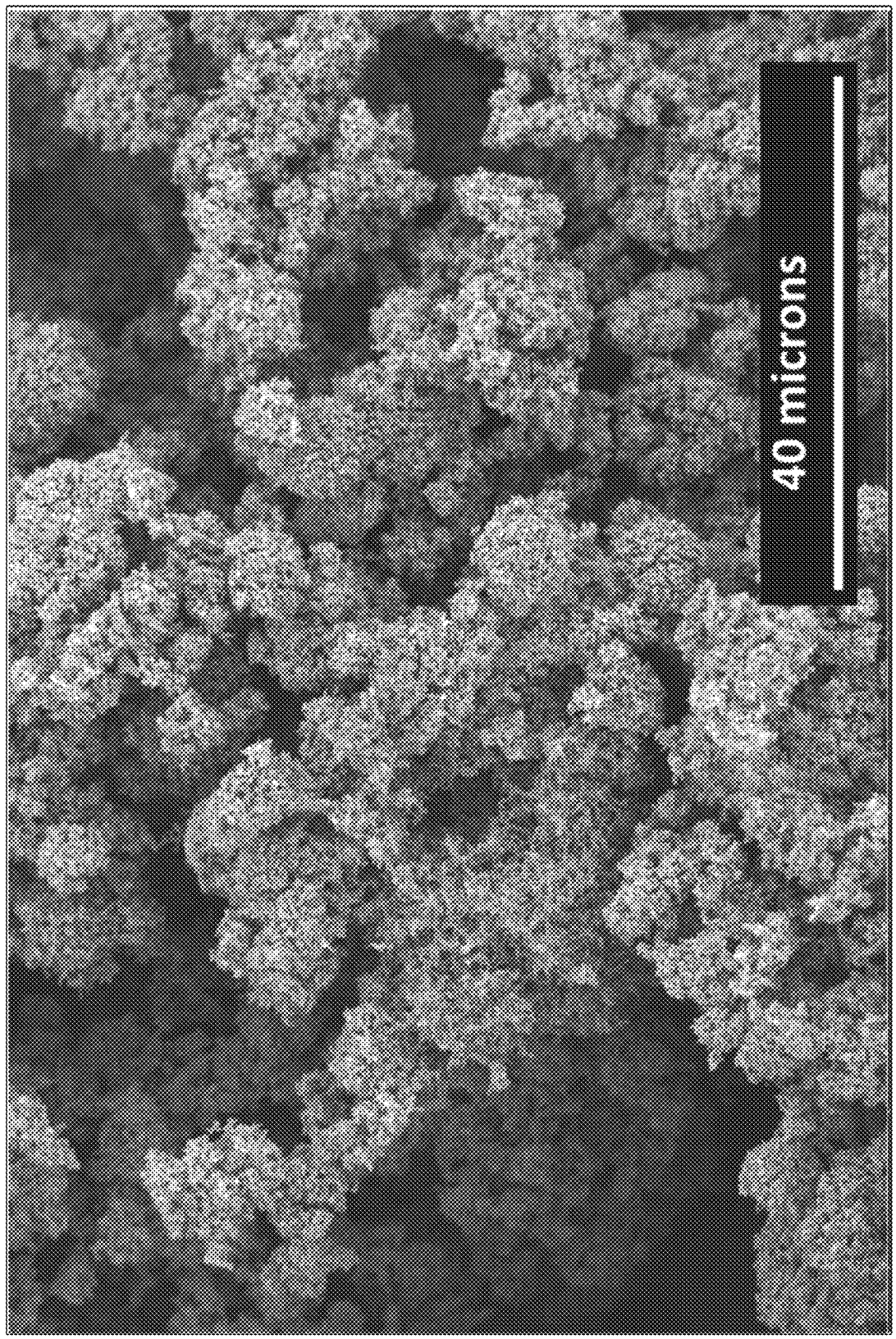
FIGS. 19A and 19B show scanning electron microscope (SEM) images from particulate carbon containing graphene, in accordance with some implementations.
Figure 19B:
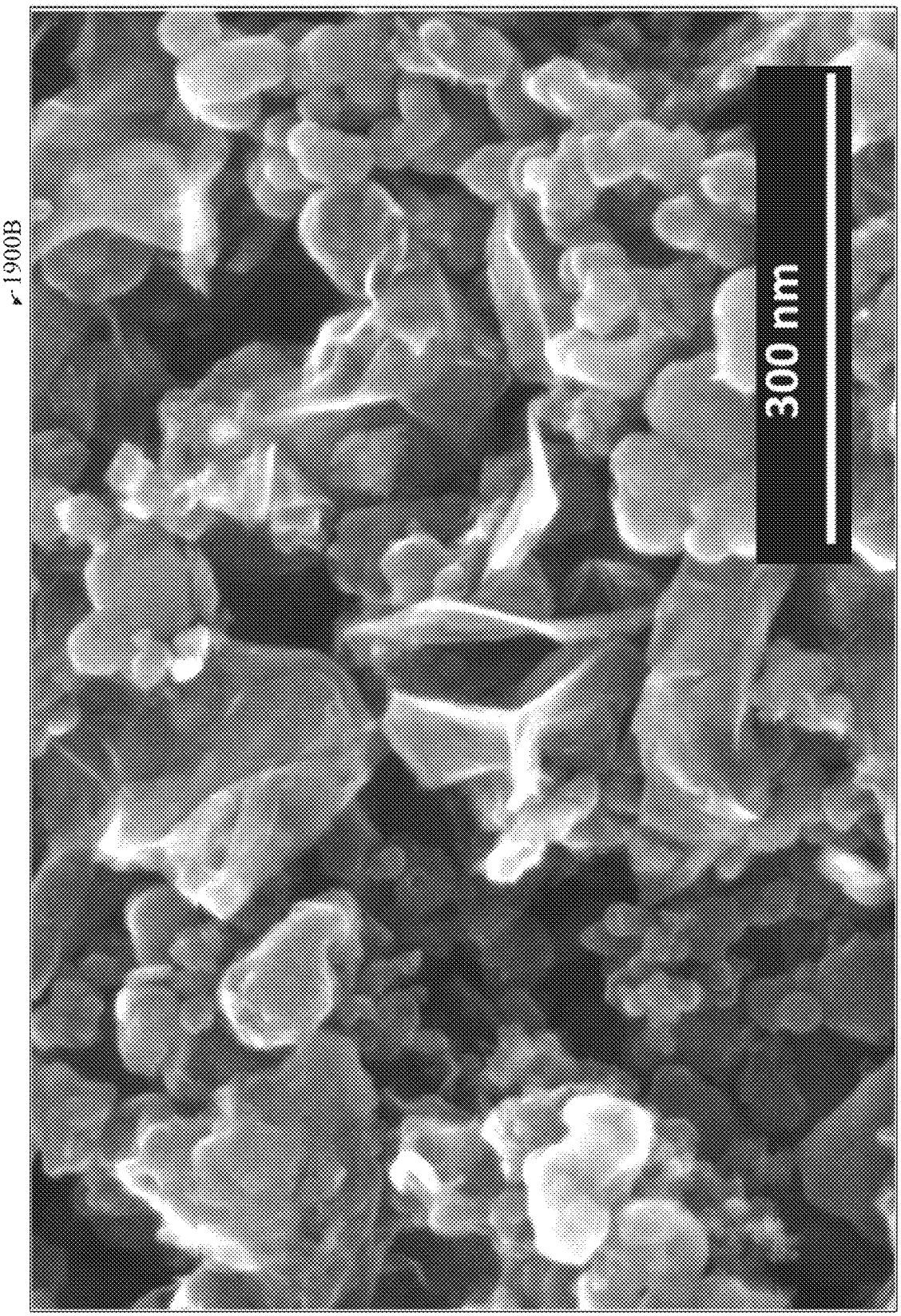
Figure 20A:
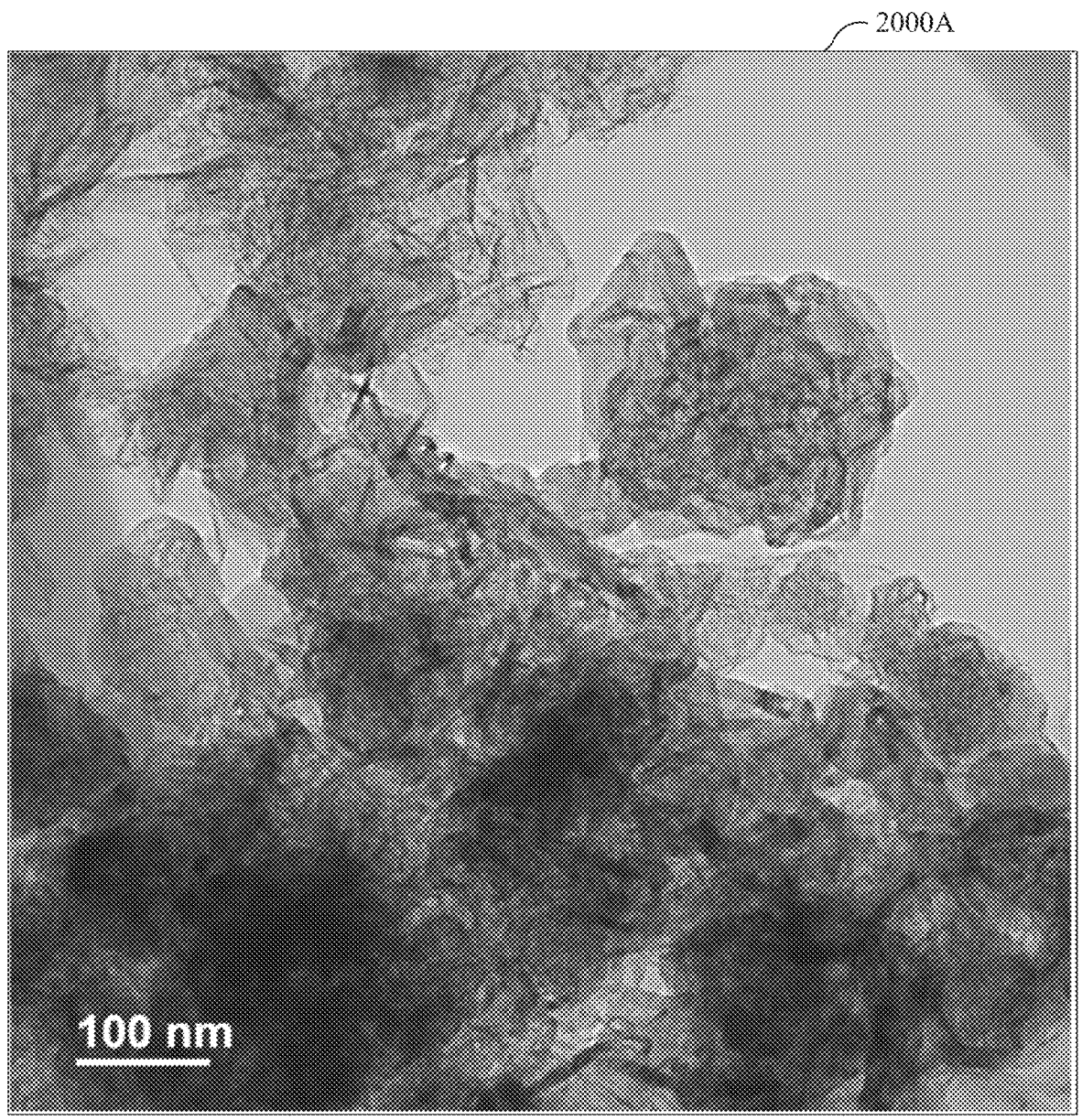
FIGS. 20A and 20B show transmission electron microscope (TEM) images from particulate carbon containing graphene, in accordance with some implementations.
Figure 20B:
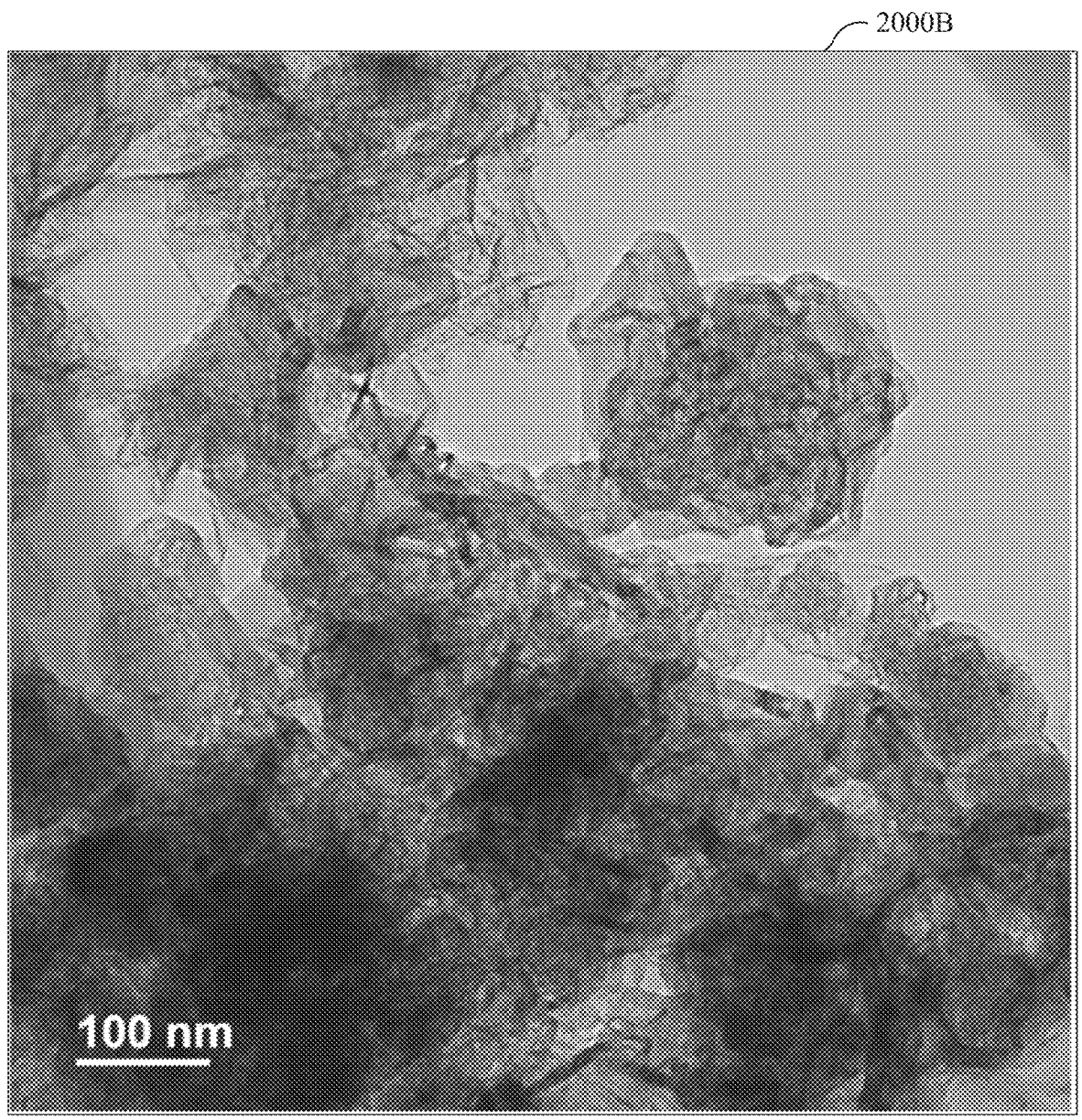

FIGS. 19A and 19B show SEM images, and FIGS. 20A and 20B show TEM images, of the carbon aggregates of the particulate carbon of this example showing graphite and graphene allotropes. The layered graphene is clearly shown within the distortion (wrinkles) of the carbon. The 3D structure of the carbon allotropes is also visible. The carbon allotropes in this example have a 3D structure with a hierarchical mesoporous, few layer, graphene structure with a specific edge-to-basal plane ratio. In some implementations, the edge-to-basal plane ratio for the graphene in the present particulate carbon is about 1:10, or about 1:100, or from 1:10 to 1:100.

The surface area of the aggregates in this example were measured using the nitrogen BET method and the density functional theory (DFT) method. The surface area of the aggregates as determined by the BET method was approximately 85.9 m2/g. The surface area of the aggregates as determined by the DFT method was approximately 93.5 m2/g.

In contrast to conventionally produced carbon materials, the microwave plasma reactor produced carbon particles and aggregates in this example contained graphite and graphene had high purity, high electrical conductivities, and large surface areas. Additionally, these particles had Raman signatures indicating a high degree of order and contained no seed particles.

In some implementations, the particulate carbon in the present gas sensors contains doped carbon materials (such as carbon doped with H, O, N, S, Li, Cl, F, Si, Se, Sb, Sn, Ga, As, and/or other metals), undoped carbon materials, or combinations thereof. Doped carbon can also include carbon with a matrix allotrope doped with carbon atoms (not in the matrix structure) and/or doped with other types of carbon allotropes. Doped carbon materials can also be doped with functional groups, such as amine (NH3) groups. In some implementations, doped carbon materials are formed using a dopant material, where the dopant material is introduced within a gas, liquid, or colloidal dispersion and fed into a reactor that is used to produce the doped particulate carbon. For example, dopant materials can be combined with a hydrocarbon precursor material and cracked in a reactor (such as a microwave plasma reactor or a thermal reactor) to produce a doped particulate carbon.

In some implementations, the particulate carbon in the present gas sensors contains nano-mixed particulate carbon. In some implementations, the surface area, structure, and/or surface activity of the present particulate carbon materials are tuned by nano-mixing the carbon particles within the carbon materials with particles of other materials. In some implementations, particles of nano-mix additive materials can be beneficially integrated with particles of the graphene-based carbon on a particle level, which shall be referred to as nano-mixing in this disclosure. The average diameter of the particles of the nano-mix additive material and the graphene-based carbon materials in the nano-mixed particulate carbon can be from 1 nm to 1 micron, or from 1 nm to 500 nm, or from 1 nm to 100 nm, or can be as small as 0.1 nm. In some implementations, the nano-mix additive material and the graphene-based carbon material are chemically bound, or are physically bound, together in the nano-mixed particulate carbon. In some implementations, the nano-mixing involves introducing nano-mix additives during particulate formation (such as during a hydrocarbon cracking process in a microwave plasma reactor or in a thermal reactor) such that the nano-mix additive material is integrated into the graphene-based carbon material as the carbon material is produced, rather than combining a carbon raw material with an additive in a later process as in certain conventional methods. In some implementations, the nano-mix additive material can be introduced as a gas, liquid, or colloidal dispersion into a reactor that is used to produce the nano-mixed particulate carbon. As an example, silicon can be input into a reactor along with a hydrocarbon process gas (or other carbon-containing process material such as a liquid alcohol) to produce silicon nano-mixed with graphene, graphene-based carbon materials, and/or other carbon allotropes. In other examples, the resulting nano-mixed particulate carbon of the present implementations can contain particles of O, S, LixSy (where x=0-2 and y=1-8), Si, Li22Si5, Li22–xSi5–y (where x=0-21.9, and y=1-4.9), and Li22–xSi5–y–zMz (where x=0-21.9, y=1-4.9, z=1-4.9, and M is S, Se, Sb, Sn, Ga, or As), and/or other metals.

In some implementations, the particulate carbon to be used in the present gas sensors are produced and collected, and no post-processing is done. In other implementations, the particulate carbon is produced and collected, and some post-processing is done. Some examples of post-processing include mechanical processing, such as ball milling, grinding, attrition milling, micro-fluidizing, jet milling, and other techniques to reduce the particle size without damaging the carbon allotropes contained within. Some examples of post-processing include exfoliation processes such as shear mixing, chemical etching, oxidizing (such as Hummer method), thermal annealing, doping by adding elements during annealing (such as O, S, Li, Si, Se, Sb, Sn, Ga, As, and/or other metals), steaming, filtering, and lypolizing, among others. Some examples of post-processing include sintering processes such as SPS (Spark Plasma Sintering, such as Direct Current Sintering), Microwave, and UV (Ultra-Violet), which can be conducted at high pressure and temperature in an inert gas. In some implementations, multiple post-processing methods can be used together or in series. In some implementations, the post-processing can produce the functionalized carbon nanoparticles or aggregates described herein.

The particulate carbon described herein can be combined with a second phase of material to create composite films. These composite films can be fabricated utilizing different methods to create specific detector responses.

In an example, solid carbon particles (such as particle size from 0.3 microns to 40 microns) and polymer beads (such as ball mixed for size reduction and improved aggregation) can be mixed in a ratio of 90:10 respectively (or in ratios from 95:10 to 5:95). This mixture can then be cast onto a substrate (such as one containing prefabricated electrodes, or an antenna platform), and then treated (such as using a low temperature, post treatment in an inert gas oven, a reactive gas oven, or a vacuum oven).

In another example, the mixing of the solid carbon particles and polymer beads described in the example above can be further combined with a solvent to form an ink, which can then be deposited onto a substrate (such as cast using doctor blade or printed). After deposition, the film can then be treated at a low temperature to remove the solvent and consolidate the film.

In another example, particulate carbon can be encapsulated with a polymer to form colloidal core-shell structures that can be printed onto antenna platform using various techniques including inkjet printing, aerosol spray coating, spin coating and roll coating.

In another example, the particulate carbon can be combined with a soluble polymer to form jettable inks for printing. In such applications, conductive binders, such as silver flakes/particles, can also be added to tune the dielectric properties (such as at particle-particle contact points).

Electrochemical Sensors

Figure 21:
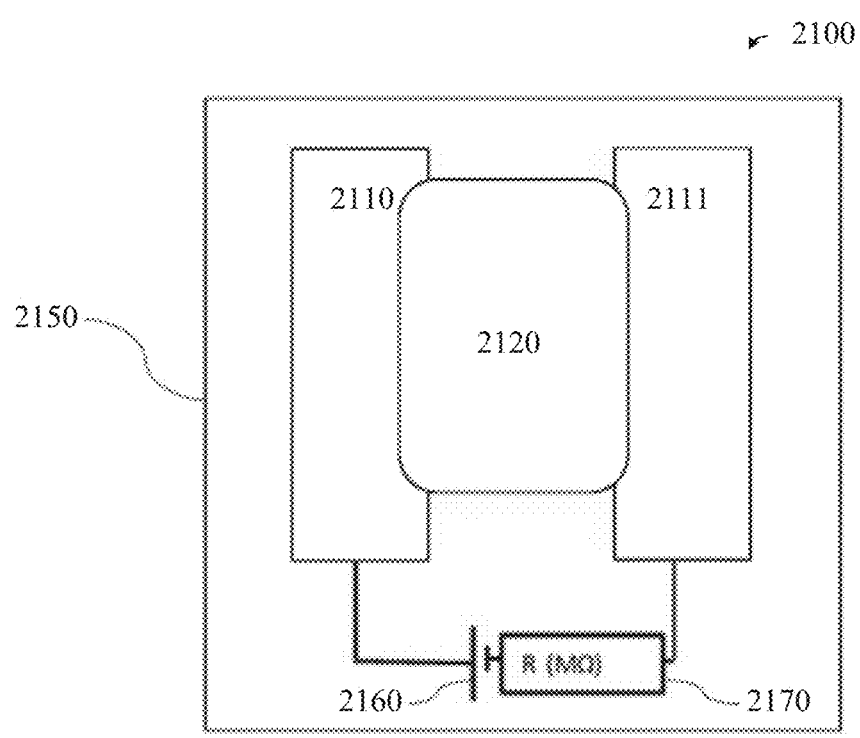
FIG. 21 is a plan view schematic of an electrochemical gas sensor, in accordance with some implementations.

FIG. 21 is a plan view schematic of an electrochemical gas sensor 2100, in accordance with some implementations. The gas sensor 2100 has a circuit containing a first electrode 2110 printed from a conductive ink, a second electrode 2111 printed from a conductive ink, a non-volatile electrolyte 2120 that electrically couples the first electrode 2110 to the second electrode 2111, a signal generator 2160 (shown as a voltage source), and a measurement (or detection) circuit element 2170 (shown as a mega-Ohm resistance measurement in the figure, but could also be a capacitance, impedance or other electrical measurement in other implementations). The presence of a target chemical produces a detectable signal between the two electrodes 2110 and 2111. For example, the change in the resistance of the circuit, the capacitance of the circuit, and/or the impedance of the circuit can be used as a detection signal. One of the electrodes 2110 or 2111 serves as the sensing electrode, and the other is the counter electrode. In some implementations, one or both of the electrodes 2110 and 2111 contain particulate carbon (such as the particulate carbon described herein), silver particles, metal particles, conductive oxide particles (such as indium tin oxide and/or fluorine-doped tin oxide particles), or other conductive particulate materials (including any aspect ratio particulates, such as those shaped as spheroids, rods, and wires). In other implementations, one or both of the electrodes 2110 and 2111 contain carbon allotropes such as, but not limited to, graphene, graphenes (graphene-based materials), graphene oxide, reduced graphene oxide, graphite oxide, graphite intercalation compounds, graphite, graphene, carbon nano-onions, diamond, p-type diamond, n-type diamond, glassy carbon, amorphous carbon, activated carbon, carbon black and/or carbon nanotubes. The carbon materials in the first electrode 2110 may be the same as or different from the carbon materials in the second electrode 2111. In one implementation, the first electrode 2110 includes a high surface area, highly conductive carbon allotrope combined with a redox mediator such as from the class of metallocenes (such as ferrocene), while the second electrode 2111 includes a conductive ink with a low surface area carbon allotrope with no redox mediator. In various implementations, the first electrode 2110, second electrode 2111, and electrolyte 2120 are all printed on a substrate 2150, such as by ink-jet printing. In some implementations, the substrate 2150 is a rigid or flexible material, such as paper, such as paper used in a label material. Some other non-limiting examples of substrate materials are polymers (such as polyethylene terephthalate, or polypropylene), and cardboard. One benefit of the present gas sensors is that they can be printed on many different substrates, in accordance with some implementations.

In some implementations, the electrolyte 2120 can be inkjet printed and contain materials such as polymer electrolytes, ceramics, or monomers that solidify into a suitable solid electrolyte. Examples of liquid electrolyte materials include ionic liquids, such as 1-butyl-3-methylimidazolium bis(trifluoromethylsulfonyl)imide, 1-butyl-3-methylimidazolium hexafluorophosphate, 1-butyl-3-methylimidazolium tetrafluoroborate, 1-hexyl-3-methylimidazolium tris(pentafluoroethyl)trifluorophosphate, 1-butyl-1-methylpyrrolidinium bis(trifluoromethylsulfonyl)imide, ethylammonium nitrate, and tetrabutylmethylammonium bis(trifluoromethylsulfonyl)imide. Ionic liquid monomers with acrylate functional groups can be in-situ polymerized to make polymer ionic liquids, such as poly(tetrabutylphosphonium3-sulfopropylacrylate) or poly(tributylhexylphosphonium 3-sulfopropylacrylate). Alternatively, solid polymer electrolytes could be used, which include a copolymer of poly(tetrafluoroethylene) with poly(sulphonylfluoride vinyl ether) (commercial example includes Nafion 117 from DuPont), poly (dimethyldiallyammoniuim chloride), plasticized poly (vinylchloride) containing tetrabuylammonium hexafluorophosphate, and poly(ethylene oxide) complex with silver trifluoromethane sulfonate. In some implementations, the electrolyte 2120 contains a reactive chemistry additive and serves as a sensing material (such as and neither of the electrodes contains a reactive chemistry additive). In such cases, the presence of the target chemical is detected by measuring a change in a signal (such as the capacitance of the circuit) in the sensor 2100 due to the change in the electrical properties of the electrolyte. Not to be limited by theory, in some cases, charge arising from electron transfer from a reactive chemistry additive (such as a redox mediator material) compound to a target molecule (such as the compound of interest (such as analyte or target chemical), or products arising from the compound of interest) affects the electrical properties of the electrolyte, thereby affecting the signal in the gas sensor 2100. The electrolyte 2120 can have as a solvent: water, polar organic solvents, ionic liquids, or polymer electrolytes, for instance. In some implementations, the electrolyte can be printed from a class of polymer electrolytes or ionic liquids. In some cases, the sensing reactions (such as the interaction of the sensing material with the analyte) in any of the gas sensors described herein occur at room temperature and ambient pressure, or at elevated temperatures (such as from 30° C. to 80° C.). In some cases, photons (such as visible light, or UV light) are introduced to the sensing material of any of the gas sensors described herein to increase the rate of the sensing reactions.

In other implementations, one or both of the first and second electrodes 2110 and 2111 serves as a sensing material, and includes a redox mediator, where the redox mediator may be in the form of a polymer or a solution. That is, in some implementations, at least one of the first electrode, the second electrode, or the electrolyte material contains a redox mediator.

The one or both of the first and second electrodes 2110 and 2111, or the electrolyte 2120 can include a redox mediator, which is a compound that donates or receives a proton or an electron from an electrode and performs reduction or oxidation of a substance in bulk solution away from the electrode by transferring this electron or proton to/away from the substance. FIG. 22 is a table that lists non-limiting examples of possible redox mediators that may be used in the present implementations. In some implementations, the redox mediator is an organometallic material, such as a metallocene (such as ferrocene). In various implementations, the redox mediator is a polymer or a solution in which there is non-covalent tethering of the redox mediator to the carbon one or more of the gas sensor components (such as the first or second electrodes 2110 and 2111, and/or the electrolyte 2120), covalent tethering, or the redox mediator is untethered to the carbon. Tethering-whether covalent or non-covalent-causes the redox mediator to be immobilized by binding it to a component of the sensor (such as the positive electrode). Covalent tethering of the mediator refers to chemically bonding a material that has redox activity to a carbon (such as using organic chains comprised of, for instance, combinations of carbon, oxygen, nitrogen, silicon, sulfur, and/or hydrogen).

Figure 23:
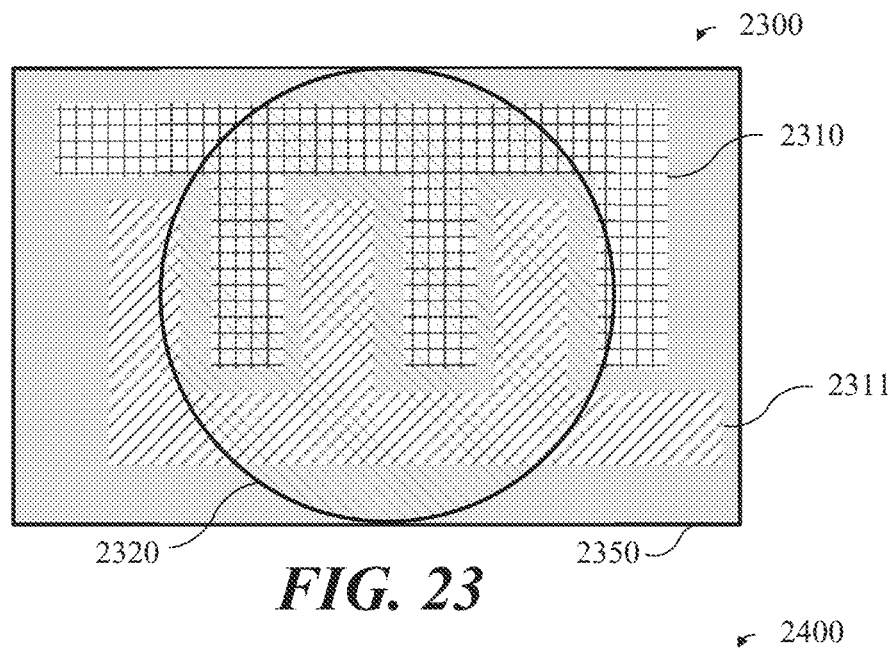
FIG. 23 shows an example of an electrochemical sensor where a first electrode and a second electrode are configured as interdigitated fingers, in accordance with some implementations.

FIG. 23 shows an example of an electrochemical gas sensor 2300 in another implementation of an electrochemical sensor, where a first electrode 2310 and a second electrode 2311 are configured as interdigitated fingers to increase the area for electrical interaction between the electrodes, which can be beneficial for example in cases where the electrolyte contains the sensing material (such as reactive chemistry additives). Additionally, such an interdigitated electrode geometry can be used to tune the capacitance of the sensor element to allow it to be integrated with other circuit elements more advantageously. In some implementations, the first and second electrodes 2310 and 2311 are printed using carbon-based conductive inks (optionally containing one or more redox mediators), as described in relation to the sensor 2100 of FIG. 21. An electrolyte 2320, which can include a redox mediator (as described in relation to FIGS. 21 and 22), can be printed as a layer over the electrodes 2310 and 2311. In the illustrated implementation, the electrolyte 2320 is configured as a circular layer (such as by applying a droplet of the electrolyte during fabrication of the sensor). However, in other implementations the electrolyte 2320 can be formed (such as inkjet printed or cast) in other geometries, such as a rectangular layer, or other patterned shape to impact the electrical properties of the sensor circuit. Some non-limiting examples of materials for the electrolyte are polymers (such as poly (ether urethane) (PEUT), polyepichlorohydrin (PECH), polyisobutylene (PIB), and alkyl cellulose), ceramics, or monomers that solidify into a suitable solid electrolyte. The first electrode 2310, second electrode 2311, and electrolyte 2320 can all be printed on a flexible or rigid substrate 2350, where the substrate 2350 may be, for example, an $SiO_2$-coated paper or polymeric material.

In some implementations, the electrodes and electrolytes of the present implementations contain the particulate carbon described herein and are tuned to sense the target chemical. In some implementations, tuning the particulate carbon materials includes functionalizing the particulate carbon to be sensitive to certain materials. For example, the particulate carbon can contain one or more reactive chemistry additives which react with a target chemical to be detected. Some non-limiting examples of target chemicals moieties that can be detected by the sensors of the present disclosure include, but are not limited to, acetone, ammonia, carbon monoxide, ethanol, hydrogen peroxide (H2O2), nitro (NO2) groups, oxygen, and water (such as to detect humidity levels). Characteristic interactions between these chemicals and reactive chemistry additives of one or more of the gas sensor components are used to detect the presence of these chemicals. For example, NO2 groups withdraw electrons, NH3 gas is an electron donor, CO2 gas is an electron donor, acetone is a neutral molecule, H2O2 is an oxidizer, and ethanol is an electron donor. When a gas species interacts with a reactive chemistry additive in the sensing material, these types of interactions change the electrical properties (such as the conductivity, or the complex impedance) of the sensing material, which causes a change in the measured response from the gas sensor indicating the presence of the species.

In an example, a sensing material in a gas sensor contains particulate carbon containing p-type doped graphene semiconductors, which have a response towards NO2, CO2, or NH3 gases. NO2 gas or NO2 containing molecules adsorb/desorb on a graphene surface via three adsorption configurations: nitro, nitrite, and cycloadditions. During these configurations, there is a charge transfer between NO2 molecules and the p-type graphene molecules. The electron withdrawing effect of NO2 increases the hole-density which leads to a decrease in resistance (or a change in the complex impedance spectrum). CO2 and NH3 are donors, so the resistance of the p-type doped graphene semiconductors increases (or the complex impedance spectrum changes) due to a depletion in hole density.

In another example, a sensing material in a gas sensor contains particulate carbon containing n-type graphene composites, which can be used for acetone sensing. In graphene-zinc-ferrite composites, surface oxygen sp hybrid orbitals interact with acetone to form CO2 and H2O and release free electrons which decreases the resistance (or change the complex impedance) of the sensing material. In a further example, a graphene composite with iron (II) reacts with H2O2 to produce O2 and Fe (III). Either O2 can be detected, or UV can be used to check the wavelength of the Fe (III) complex.

In some implementations, the carbon allotropes within the particulate carbon in the present sensors can be tuned to detect the desired chemical by utilizing a certain microstructure, such as the porosity or curvature (such as curved graphene) of the carbon. The carbons can contain sp3, sp2 and/or sp hybrid orbitals, or a combination of these. In other implementations, tuning can be achieved by adding reactive chemistry additives in the form of functional groups to the carbon, such as oxygen, ketones, or carboxyl. The tuning in the various implementations may be achieved during initial production of the carbon, and/or by post-processing after the carbon has been made. The post-processing, as described herein, can include steps such as changing the surface area of the carbon material (such as by ball milling), changing the conductivity, adding functional groups, or a combination of these.

In an experimental run, a sensor similar to that of FIG. 23 was used to detect the presence of hydrogen peroxide. The interdigitated fingers in this example contained the particulate carbon described herein. The redox mediator solution was 10 μL of 5 mM bis(pentamethylcyclopentadienyl) iron (II), 100 mM tetraethylammonium tetrafluoroborate, and 25 mM KOH in butylmethylimidazolium tetrafluoroborate. The sensor was activated by applying a voltage of 1.0 V in the absence of peroxide and then allowed to equilibrate for 5 minutes to establish a baseline current. The sensor was then put into an atmosphere containing peroxide (single digit parts per million to parts per billion) for 1.0 hr, after which a voltage of 1V was applied and the current was measured. The results are shown in Table 1 below.

TABLE 1

Sample experimental results for electrochemical sensor

| | Test cycle 1 | | Test cycle 2 |
|---|---|---|---|
| Current | 2.63 μA | 19.7 μA | 20.5 μA |
| Energy | 311 nWh | 1912 nWh | 1973 nWh |

As can be seen from Table 1, the baseline currents increased approximately 650%—from 2.63 μA to 19.7 μA—and remained constant (20.5 μA) for the second hold/test cycle. Thus, the electrochemical sensor demonstrated the ability to detect peroxide with high sensitivity using low amounts of electrical power.

High Frequency Sensors

Some electrochemical sensors utilize direct current (DC) electrical signals to detect changes to a sensing material (such as changes in charge carrier concentration causing a change in resistance to indicate chemistry, and/or changes in molecular structure causing a change in capacitance to indicate chemistry). While such DC gas sensors are capable of sensing low levels of chemistry, the detection range without costly equipment (such as utilizing high power energy sources) to drive chemical reactions makes widespread adoption impractical for most applications. In the present implementations, alternating current (AC) signals are used to detect characteristic, reversible impedance responses of a sensing material. In some such gas sensors, a multi-frequency AC signal (such as RF current with a range of frequencies) is applied to a sensing material within a sensing circuit and the complex impedance of the circuit is detected. The frequencies of the AC signals used in such "high frequency" gas sensors are typically greater than 1 kHz, or are from 1 kHz to 20 GHz, or are from 100 kHz to 20 GHz.

High frequency gas sensors contain AC circuits with a sensing material incorporated. The geometries and materials in the AC circuits can be tuned to be sensitive to certain frequency ranges, and the complex impedance of the AC circuit changes upon interaction with an analyte that changes the complex impedance of the sensing material. In general, the complex impedance of a material within the AC circuit will affect the signals detected from the circuit and can be tuned to tune the response of the circuit. For example, the sensing material can contain a carbon material, the properties of the carbon material can affect the complex impedance, and therefore the complex impedance of a carbon sensing material and a sensing circuit containing that material can be controlled by specifically tuning the properties of the carbon materials (such as the structure of the carbon materials, the types of allotropes present, and the concentration of defects in any ordered carbon allotropes present).

In some implementations, high frequency gas sensors contain a structured material within the sensing material. The complex impedance of a structured material is a result of the inherent materials properties forming the structure as well as the geometry of the structure, such as the pore size, the pore spacing and the macroscopic shape of the material. In the case of composite structured materials, the distribution of the materials with different properties also affects the complex impedance of the material. For example, electrically conductive materials (such as the particulate carbons described herein) can be structured into a mesoporous structure and be decorated with other materials such as dielectrics or permeable materials. In some implementations, the structure, composition, distribution of materials, and/or the concentration of impurities and/or defects are changed to tune the complex impedance of a structured sensing material within a high frequency gas sensor. Such a structured sensing material is beneficial in high frequency resonant gas sensors because they contain a variety of random paths and path lengths available for conduction at many frequencies, which can provide a sensor with a wide bandwidth of frequencies with which to detect a target analyte. In some implementations, the structured materials (such as with the particulate carbon described herein) are frequency selective materials, which are used in high frequency circuits within the present gas sensors.

In some implementations, dielectric polarization modification impedance spectroscopy is utilized, which is a low-cost method for detecting low concentrations of analytes (such as volatile gases or vapors) in a gas sensor. In some implementations, an impedance spectroscopy measurement can be used to detect the modulation of properties of a sensing material containing reactive chemistry additives (such as a structured sensing material containing particulate carbon and a redox mediator in the presence or absence of an analyte). For example, selective frequency interrogations of S21 (such as the transmission of a high frequency signal through an AC circuit or system) and S11 (such as the reflectance of a high frequency signal from an AC circuit or system) can be used to detect a change in the complex impedance of the sensing material and/or circuit (or system) as a whole. The operation of the gas sensor relies on a change in the measured S21 or S11 value upon exposure to an analyte.

The combination of such high frequency gas sensors (such as utilizing impedance spectroscopy) and the unique properties of the particulate carbon described herein (such as structure, surface area, and conductivity) enables gas sensors that are able to generate the same results as the more costly counterparts (such as detecting an analyte with concentrations in the parts per million (ppm) or parts per billion (ppb) ranges) at a greatly reduced price, and an improved ease of adoption and portability. The low power requirement of the present implementations allows for the system to be powered by battery systems and in some cases using energy harvester systems. Additionally, the imaginary part of the complex impedance of the sensing materials described herein have spectral signatures (such as peaks in the spectra) that can discriminate one molecular arrangement from others, enabling the detection of several molecules with one sensor.

Figure 24:
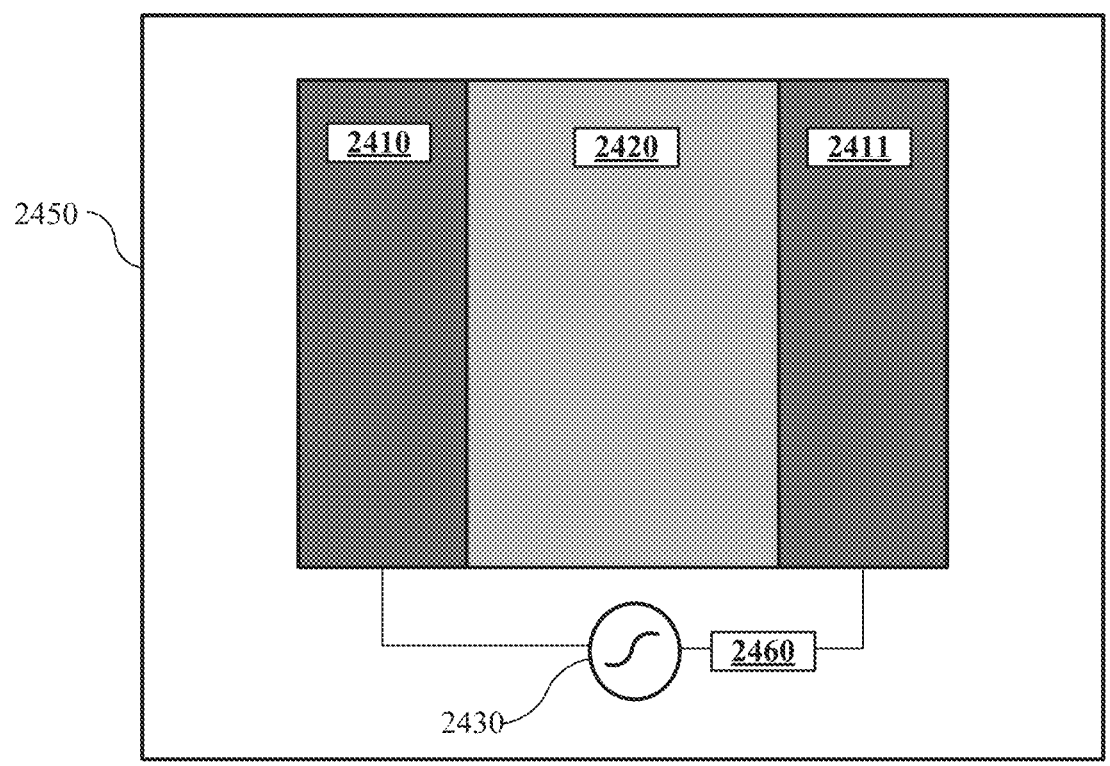
FIG. 24 shows an example of a chemical sensor in which high frequency spectroscopy is used as the detection method, in accordance with some implementations.

FIG. 24 shows an example implementation of a chemical sensor 2400 in which high frequency (such as impedance) spectroscopy is used as the detection method. Sensor 2400 includes a first electrode 2410, a second electrode 2411, and a dielectric 2420 sandwiched between the electrodes 2410 and 2411, all of which are arranged on substrate 2450. In some implementations, the electrodes 2410 and 2411 and/or the dielectric 2420 are printed from inks on the substrate 2450. Substrate 2450 may be rigid or flexible, for example, a label. In some cases, a device may be formed on both sides of a substrate. In some implementations, the electrodes 2410 and 2411 contain the particulate carbon described herein), silver particles, metal particles, conductive oxide particles (such as indium tin oxide and/or fluorine-doped tin oxide particles), or other conductive particulate materials (including any aspect ratio particulates, such as those shaped as spheroids, rods, and wires). In other implementations, one or both of the electrodes 2410 and 2411 contain a carbon allotrope such as, but not limited to, graphene, graphene oxide, carbon nano-onions, and/or carbon nanotubes. In some implementations, one electrode includes a metal while the other electrode does not. One or both electrodes 2410 and 2411 and/or dielectric 2420 can include a reactive chemistry additive (such as a redox mediator), as described in reference to the electrochemical sensors above, which is tuned to one or more target analyte (such as volatile gas or vapor) species.

In operation, an AC source 2430 applies AC signals having a range of frequencies (such as greater than 1 kHz, or from 10 kHz to 20 GHz, or from 10 kHz to 1 GHz, or from 500 kHz to 20 GHz, or from 500 MHz to 20 GHz) to the sensor 2400, and a detection circuit 2460 detects a change in impedance at specified frequencies when the target substance interacts with (such as is absorbed into, or adsorbed onto) the sensing material. In some implementations, the sensor 2400 uses an impedance spectroscopy technique, in which specific target analyte chemicals interact with the sensing material (such as containing the particulate carbon described herein) causing a change in the complex impedance of the sensing material. The change in the complex impedance can then be measured by the circuitry 2460, and the measured change used for detecting the target substance. In some implementations, the sensing material contains tailored carbon and a reactive chemistry additive with electrons that interact with the target compound and change the resonance frequency.

High Frequency Resonant Sensors

One type of a high frequency gas sensor is a resonant gas sensor. In some implementations, a resonant gas sensor contains one or more sensing materials, and changes to the resistivity and permittivity of the sensing materials result in changes to the resonant behaviour of the sensor. In some implementations, such a resonant gas sensor can be printed and utilize small electronics (such as a small IC chip), such that it can be miniaturized and produced at low cost. Such low-cost miniature resonant gas sensors have a myriad of applications including product labels on food packaging, shipping labels on packages, and portable hazardous/toxic gas sensors. In some implementations, low-cost resonant gas sensors are enabled by the particulate carbon materials described herein, which improve the resonant gas sensor sensitivity allowing for low power signals to produce adequate responses. For example, the high the surface area and mesoporous structure of the particulate carbon allows more analyte vapors to enter into the structure and increases the changes in the sensing material resistivity and permittivity for a given analyte concentration. In some implementations, the sensing materials or materials making up the other elements (such as with the particulate carbon described herein) contain frequency selective materials, which are used to tune the resonant frequencies of the resonant circuits within the present gas sensors.

In some implementations, the resonant gas sensors contain pickup electrodes to provide AC signal power input to the sensing materials and detect an output from the sensing materials. The geometries of the constituent elements can be tuned in order to produce a resonant structure with certain frequency response in the sensor. In addition, the materials properties (such as resistivity and/or complex permittivity) of the sensing material can also be tuned to form a resonator structure or composite with a certain spectral frequency response. Tuning the materials properties and resonant structure geometries can be advantageous to enhance the performance of the gas sensor to be more sensitive in certain frequency ranges.

In some implementations, a resonant gas sensor system includes a microprocessor, which provides a signal to a transducer (such as an antenna) that drives a sensing material in the resonant gas sensor over a specific frequency range. The microprocessor can also detect the response (such as the complex impedance spectrum of the sensor). In different cases, the response can be a reflected AC signal (such as S11) or a transmitted AC signal (such as S21). The sensing material can be integrated into the transducer or be a separate element. Different resonant gas sensor architectures are described below. In some cases, the response is compared to a database (such as a library) of resonance spectra for a variety of molecular chemistries related to certain molecules of interest (such as those in explosives or rotting foods). In some implementations, the functionality of the detector and transducer are integrated into a single, monolithic, patterned film structure, optionally integrated with other electronics such as an integrated microprocessor and/or communication chip (such as to communicate a detection event to another device). The microprocessor (and other optional integrated electronics) can be powered using an integrated battery or using energy harvesting structures (such as using an antenna that absorbs RF energy or a photocell that absorbs light, coupled to an integrated capacitor to store the harvested energy). In some cases, such an integrated sensor can contain a resonant structure with engineered properties (such as conductivity, and geometry) to minimize the antenna absorption loss at high frequency.

In some implementations, a resonant gas sensor contains a set of electrically conductive elements that form a resonant structure. The resonant structure itself exhibits resonance or resonant behaviour, that is, it naturally oscillates at some frequencies, called its resonant frequencies, with greater amplitude than at others. These resonant structures within the sensors are used to select specific frequencies from a signal (such as the signal provided by the microprocessor in the resonant gas sensor systems described herein). For example, a resonant gas sensor can contain two conductive electrodes surrounding and/or electrically coupled to a dielectric or an electrically conductive gas sensing material, all of which form a single resonant structure (along with other components of the system, in some cases). In another example, a transducer (such as an antenna) can be excited with a signal, and the sensing material can be arranged adjacent to the transducer such that the complex impedance of the sensing material impacts a detected response. In some cases, the electrode(s) and/or the gas sensing material can contain the particulate carbon described herein. In some cases, the electrode(s) and/or the gas sensing material can be printed and/or be deposited from a liquid, gas or ink dispersion.

In some cases, the resonant structures described above can be incorporated into the resonant gas sensor circuit to form an LC tank circuit. For example, a coiled antenna can be used as an inductive element, and a sensing material between two electrodes can be used as a capacitive element, and the inductive and capacitive elements can be connected in parallel or in series to form a tank circuit in a resonant gas sensor. In some implementations, a single transducer structure (such as a coiled antenna) can contain (or be formed from) the sensing material, and also provide the inductive and capacitive elements of the tank circuit. Such multi-functional transducers can be driven by a microprocessor, and upon interaction with an analyte the transducer material properties change, which change the characteristic response of the gas sensor circuit, which in turn can be measured by detection circuitry to detect the presence of an analyte. In other cases, the transducer does not contain sensing materials, and the sensing materials change the properties of one or more elements within the tank circuit (such as the capacitance of a capacitive element), which change the characteristic response of the circuit, which in turn can be measured by detection circuitry to detect the presence of an analyte.

When a gas sensitive material interacts with an analyte, the complex electrical materials properties of the permittivity $\varepsilon = \varepsilon' - j\varepsilon''$ (where j is the imaginary unit) and permeability $\mu = \mu' - j\mu''$ change. In a resonant gas sensor, the varying material properties can lead to a change in the wave propagation of a signal (such as a multi-frequency signal provided by a microprocessor) through a resonant structure (such as an LC tank circuit, an antenna, or a microstrip line). In addition to the materials properties, the wave propagation of a signal in a resonant gas sensor also depends on the geometry of the structures formed by the elements of the sensor. In some cases, the resonant structures in the resonant gas sensor contain one or more waveguides, and the wave propagation of a signal also depends on the design of the waveguide(s). Generally, electromagnetic waves are guided to a desired transmission mode by restricting their expansion in one or two dimensions. One transmission structure for waves with a transversal electromagnetic mode (TEM) is the planar microstrip line, consisting of a strip conductor and a ground plane either separated by a dielectric substrate or separated by a dielectric material on a single side of a substrate. The two-dimensional structure of microstrips make them well suited for miniaturization and integration with other components and, because of the planar structure, they can be fabricated conventionally by thick or thin film technology. In some cases, the circuit elements (such as resonant structures) are formed (such as by printing) on one side of a substrate to create a resonator (such as a microstrip line with co-planar electrodes separated by a dielectric gap), while in other implementations, the elements are formed (such as by printing) on both sides of a substrate to create a resonator (such as a patch antenna separated from a ground plane electrode by a dielectric substrate containing a sensing material). The substrate can be many different materials including rigid or flexible materials, those with suitable dielectric properties, a polymer sheet, or paper. In some cases, a base layer can be pre-deposited on the substrate to act as an anchoring layer to absorb part of the deposited (such as printed) material and or to create a barrier to prevent absorption of the deposited material into the substrate (such as paper).

Figure 25A:
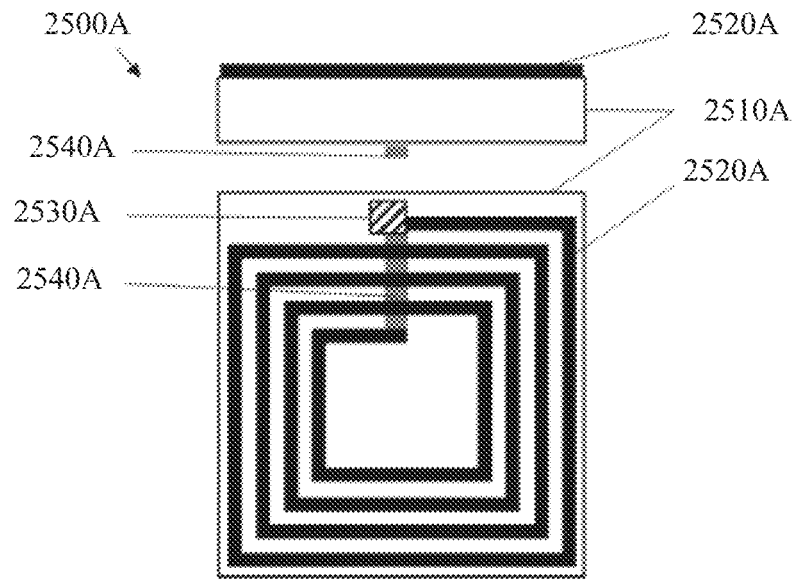
FIG. 25A shows a non-limiting example of a resonant gas sensor inside view and plan view, in accordance with some implementations.

FIG. 25A shows a non-limiting example of a resonant gas sensor 2500A inside view and plan view, including a substrate 2510A, a transducer 2520A, a microprocessor 2530A, and a ground electrode 2540A, in accordance with some implementations. A first terminal of the microprocessor 2530A is electrically coupled to a first terminal of the transducer 2520A, and the ground electrode 2540A completes the circuit from a second terminal of the transducer to a second terminal of the microprocessor 2530A. In this example, the ground electrode is connected to the second terminal of the transducer 2520A and to the second terminal of the microprocessor 2530A through vias in the substrate (not shown). The transducer 2520A in this example is a spiral with successive loops with different dimensions. The microprocessor 2530A provides AC signals at different frequencies to the first terminal of the transducer 2520A and measures the response (either reflected from the transducer 2520A or transmitted through the transducer 2520A, in different implementations). In this example, the transducer 2520A contains a sensing material (such as a redox mediator), which is sensitive to an analyte, such that when the resonant gas sensor 2500A is exposed to the analyte, the complex impedance of the transducer 2520A changes, and the response detected at the microprocessor 2530A changes indicating the detection of the analyte. In other words, the complex permittivity and/or permeability of the sensing material changes upon exposure to an analyte, which changes the resonant frequency of the sensor circuit indicating the detection of the analyte.

Figure 25B:
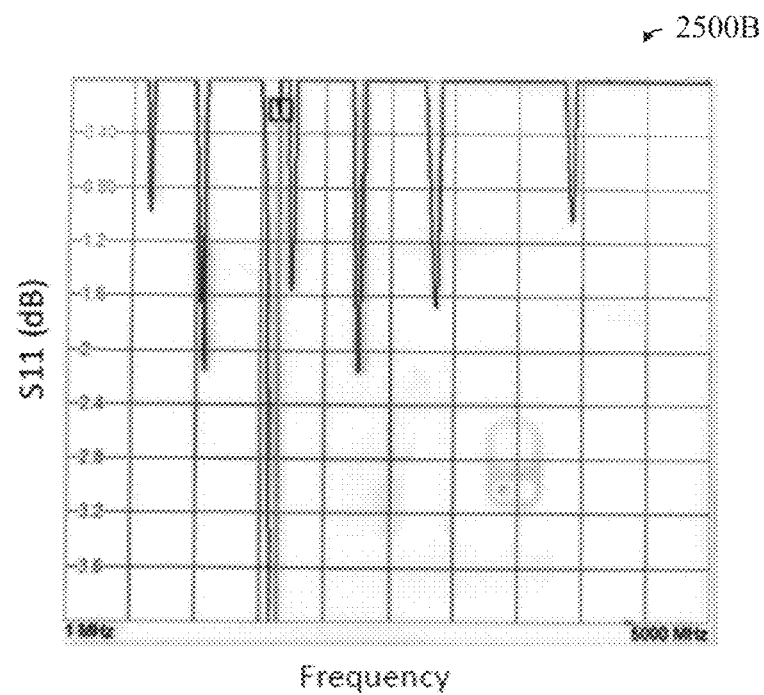
FIG. 25B shows an example of a response from a resonant gas sensor in the presence of an analyte of interest, in accordance with some implementations.

FIG. 25B shows an example of a response from a resonant gas sensor (such as 2500A in FIG. 25A) in the presence of an analyte of interest. The x-axis in the plot in FIG. 25B is frequency (from 1 MHz to 5000 MHz), and the y-axis is the reflected signal from the transducer (such as element 2520A in FIG. 25A) (such as S11, which is the signal reflected back from the first terminal of the transducer) in dB. The troughs in the plot in FIG. 25B indicate the resonant frequencies of the circuit, where the AC signals are not reflected (such as dissipated) in the resonant circuit. These troughs can change depending on the type and concentration of an analyte present, and in some cases can be compared to a library to determine the identity of a detected analyte species. Since the location of the troughs depends on the resonant frequencies of the entire gas sensor circuit, in some implementations, a library of analyte species and concentrations is created for a specific resonant gas sensor design and materials set.

Figure 25C:
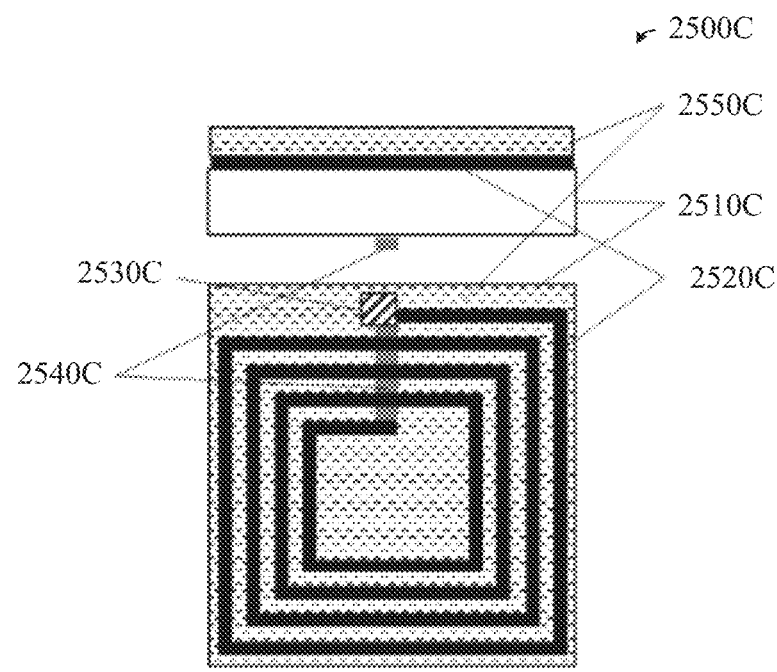
FIGS. 25C-25D show non-limiting examples of resonant gas sensors inside view and plan view, in accordance with some implementations.

FIG. 25C shows a non-limiting example of a resonant gas sensor 2502C inside view and plan view, including a substrate 2510C, a transducer 2520C, a microprocessor 2530C, a ground electrode 2540C, and a sensing material 2550C, in accordance with some implementations. The resonant gas sensor 2502C is similar to the resonant gas sensor 2500C, and further includes a separate sensing material 2550C disposed above and in between successive loops of the spiral transducer 2520C. In this example, the sensing material is sensitive to an analyte, such that when the resonant gas sensor 2502C is exposed to the analyte, the frequency response of the resonant circuit formed by the transducer 2520C and sensing material 2550C changes, and the response detected at the microprocessor 2530C changes indicating the detection of the analyte. The change in frequency response in this example can be caused by a change in the inductance of the transducer 2520C and/or a change in the capacitance between successive loops of the transducer 2520C, which change the resonant frequencies of a tank circuit formed by the transducer 2520C and sensing material 2550C. In other words, the complex permittivity and/or permeability of the sensing material changes upon exposure to an analyte, which changes the resonant frequency of the sensor tank circuit indicating the detection of the analyte.

Figure 25D:
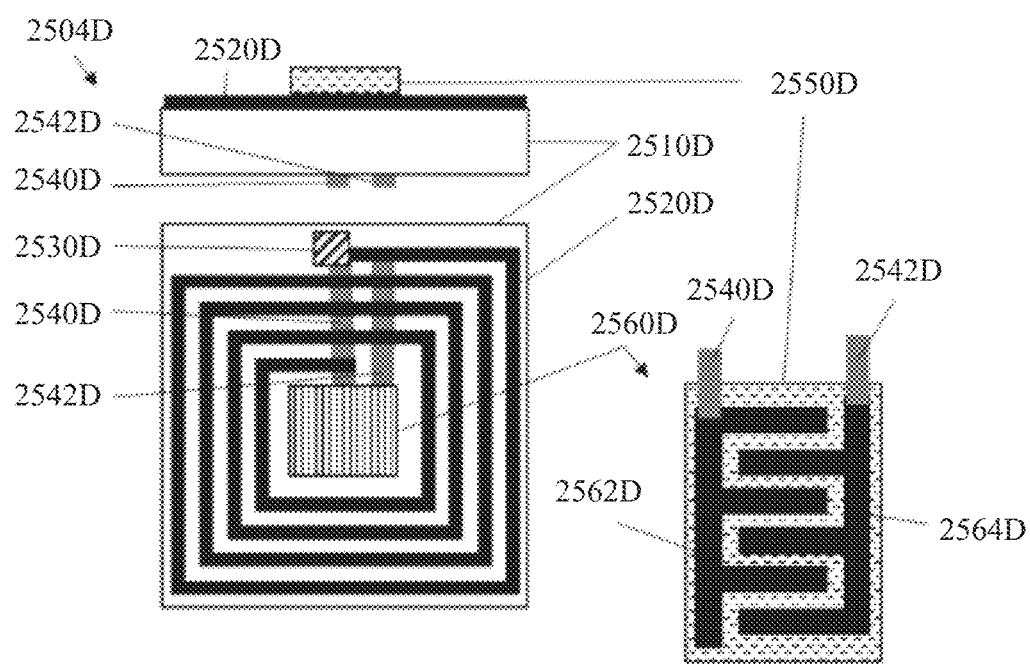

FIG. 25D shows a non-limiting example of a resonant gas sensor 2504D in side and plan views. The resonant gas sensor 2504D includes a substrate 2510D, a transducer 2520D, a microprocessor 2530D, a ground electrode 2540D, a second electrical connection 2542D, a sensing material 2550D, and a capacitive element 2560D, in accordance with some implementations. The resonant gas sensor 2504D is similar to the resonant gas sensor 2500D, and further includes a capacitive element 2560D. The capacitive element 2560D in this example is formed from interdigitated electrodes 2562D and 2564D. In this example, the capacitive element 2560D has the sensing material 2550D disposed on and between the interdigitated fingers 2562D and 2564D. In this example, the capacitive element 2560D is wired in parallel with the transducer 2520D; the ground electrical connection 2540D is electrically coupled to electrode 2562D of the capacitive element 2560D, and the second electrical connection 2542D couples the electrode 2564D of the capacitive element 2560D to the first terminal of the transducer 2520D (as described in resonant gas sensor 2500A in FIG. 25A). Therefore, an LC tank circuit (with the inductive element and capacitive element in parallel) is formed from the transducer 2520D and the capacitive element 2560D in this example. In this example, the sensing material 2550D (such as a redox mediator) is sensitive to an analyte, such that when the resonant gas sensor 2504D is exposed to the analyte, the capacitance of the capacitive element 2560D changes, and the response detected at the microprocessor 2530D changes indicating the detection of the analyte. In other words, the complex permittivity and/or permeability of the sensing material changes upon exposure to an analyte, which changes capacitance of the capacitive element 2560D and the resonant frequency of the sensor tank circuit indicating the detection of the analyte. One advantage of separate inductive and capacitive elements (such as shown in resonant gas sensor 2504D) is that the resonant frequency of the tank circuit can be tuned. One example of this is lowering the resonant frequency to a lower frequency range (such as from about 20 GHz to about 1 GHz) to reduce the cost of the electronics required to drive the sensor circuit.

Figure 25E:
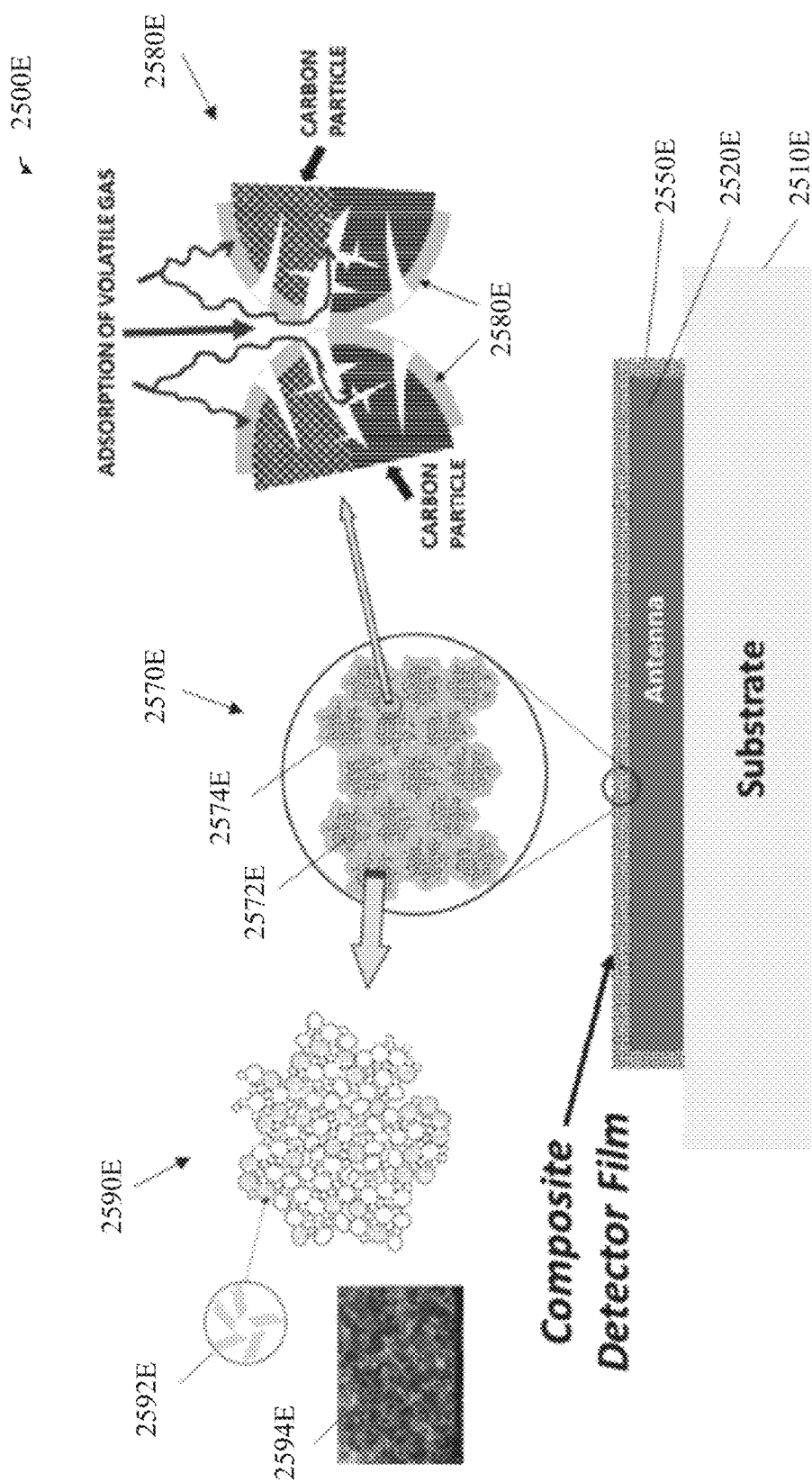
FIG. 25E shows a non-limiting example of a resonant gas sensor with a sensing material containing particulate carbon, in accordance with some implementations.

FIG. 25E shows a non-limiting example of a resonant gas sensor containing a substrate 2510E, a transducer antenna 2520E, and a composite detecting film 2550E for sorption of an analyte (such as volatile organic solvent vapors), in accordance with some implementations. The composite detecting film 2550E contains a structured particulate conducting phase encapsulated with a polymeric binder. Insets 2570E and 2580E show schematics of the particulate conducting phase 2572E encapsulated by the polymer binder 2574E. Inset 2580E shows a volatile gas (or more generally, an analyte) adsorbed by the polymer binder and/or the interior surfaces of the particulate carbon. In some implementations, the polymer binder contains one or more reactive chemistry additives, which interact with an analyte and cause the electrical properties of the sensing material 2550E to change. In other implementations, a reactive chemistry additive (such as a dissolved salt) can be deposited on and within the pores of the particulate carbon. In some cases, the reactive chemistry additives can be incorporated into the particulate carbon and the polymer binder to further improve the sensitivity of the sensing material. In some cases, the reactive chemistry additive can be added to the particulate carbon and the sensing material can contain the particulate carbon and no polymer binder. Inset 2590E shows schematics of graphene sheets 2592E and the porous 3-dimensional structure 2594E of the particulate carbon in the composite detecting film 2550E. Some non-limiting examples of the structured particulate conducting phase can contain 3-dimensionally structured microporous or mesoporous graphene-containing particles, or the particulate carbon described herein. Some non-limiting examples of polymeric binder include PEUT, PECH, PIB, and alkyl cellulose. Such structures are beneficial to detect analyte species and concentration in resonant gas sensors because they produce characteristic, reversible impedance responses that can be measured (or transduced) with a high frequency (resonant) antenna element.

Figure 25F:
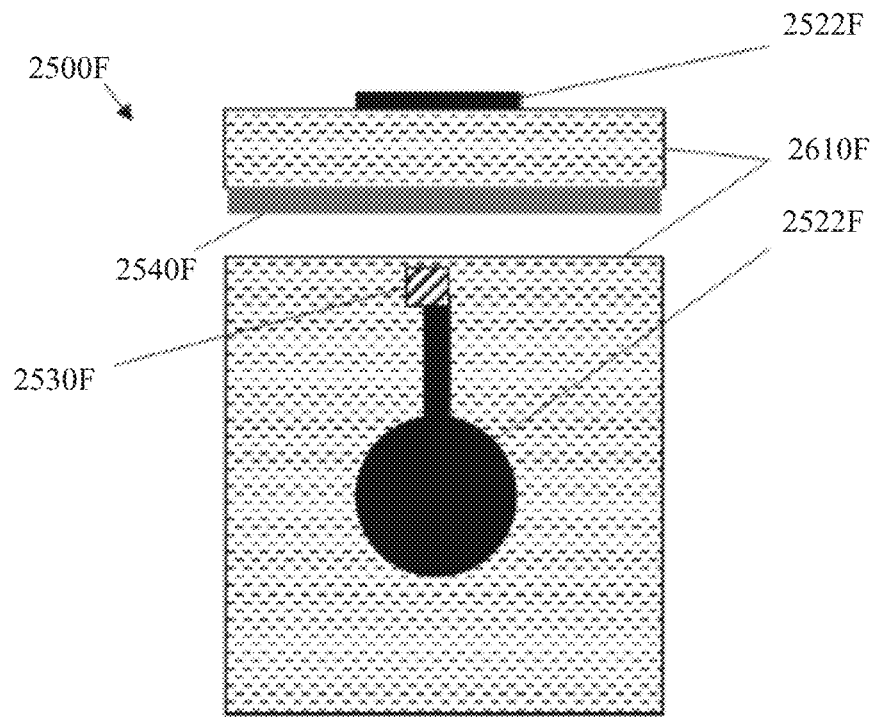
FIG. 25F shows a non-limiting example of a resonant gas sensor inside view and plan view, in accordance with some implementations.

FIG. 25F shows a non-limiting example of a resonant gas sensor 2506F inside view and plan view, including a substrate 2510F, a transducer 2522F, a microprocessor 2530F, a ground electrode 2540F, and a sensing material 2550F, in accordance with some implementations. The resonant gas sensor 2506F contains similar elements to those in resonant gas sensor 2500F, however, the transducer 2522F in this example is a patch antenna in the shape of a circle, which is electrically coupled to a first terminal of the microprocessor, rather than a spiral antenna. The ground plane is formed from ground electrode 2540F on the opposite side of substrate 2510F and is coupled to a second terminal of the microprocessor through a via in the substrate (not shown in the figure). The substrate 2510F in this example contains the sensing material. In this example, the sensing material 2550F (such as a redox mediator) is sensitive to an analyte, such that when the resonant gas sensor 2506F is exposed to the analyte, the frequency response of the resonant circuit formed form the transducer 2522F and the sensing material 2550F changes, and the response detected at the microprocessor 2530F changes indicating the detection of the analyte. Similar to the examples shown in FIGS. 25A, 25C and 25D, the response can either be reflected from the patch antenna transducer 2522F back to the first terminal of the microprocessor, or be transmitted through the patch antenna transducer 2522F and be detected at the second terminal of the microprocessor (connected to the ground electrode 2540F), in different implementations.

The resonant gas sensors described in FIGS. 25A, 25C, 25D and 25F are non-limiting examples only, and many other variations exist. For example, the electrodes, transducers, capacitive elements and/or substrates can contain sensing material in any of the above examples. In such examples, the sensing material itself can be patterned to affect the resonant frequencies of the gas sensor circuit. Additional elements can also be added, for instance, to provide additional sensing materials that can affect the response from the circuits in the above examples. The electrodes, transducers, capacitive elements and/or substrates in any of the above examples can contain the particulate carbon described herein. The electrodes, transducers, capacitive elements and/or substrates can be formed in many different shapes as well. For example, the transducers can be rectangular spiral antennas, such as that shown in FIGS. 25A, 25C and 25D, square spiral antennas, ovular spiral antennas, or other types of spiral antennas. The patch antenna transducers can be circular, such as that shown in FIG. 25F, rectangular, square, ovular, or other patch-like shapes. Other transducer shapes are also possible, such as patterns that are resonant at particular frequency ranges. In some cases, more than one transducer can be driven by a single microprocessor, and multiple signals from the circuits containing the multiple transducers can also be detected by a single microprocessor. The circuits can also contain waveguides, such as microstrip lines, instead of simple electrical connections, such as that shown in FIGS. 25A, 25C, 25D and 25F, to conduct the AC signals between elements in the gas sensor circuits. The geometry of the waveguides can be designed such that there is low loss of the AC signals between elements in the circuits. The capacitive elements can also be different types than that shown in FIG. 25D. For example, a 3-dimensional capacitor can be formed with structured electrodes surrounding a sensing material, to further increase the surface area of the capacitor and further improve the capacitance change upon exposure to an analyte. The circuits also can be electrically coupled by direct connections, such as that shown in FIGS. 25A, 25C, 25D and 25F, or can be coupled through a dielectric material (since the AC fields can extend outside of a waveguide or other resonant structure).

In some implementations, the transducers used in the gas sensors disclosed herein may be examples of the antennas or transducers described in U.S. Pat. No. 10,218,073 entitled "Microwave Chemical Processing," which is incorporated herein by reference.

Figure 26A:
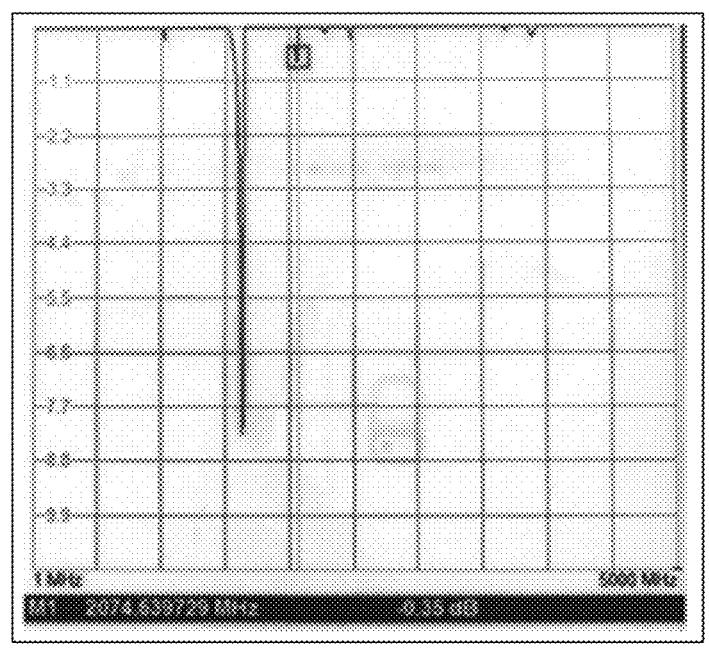
FIGS. 26A-26C show a time evolution of example spectra produced when an analyte is detected by a resonant gas sensor, in accordance with some implementations.
Figure 26B:
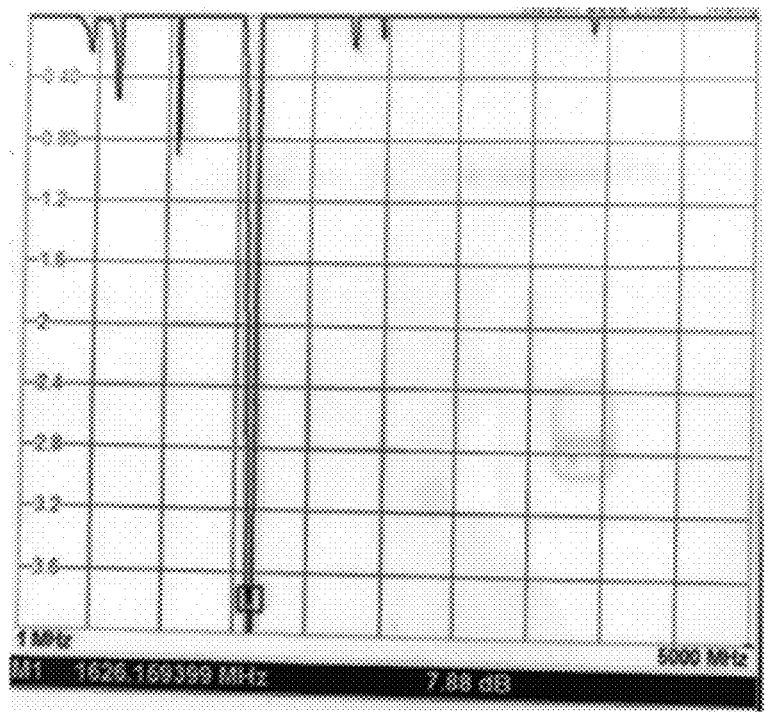
Figure 26C:
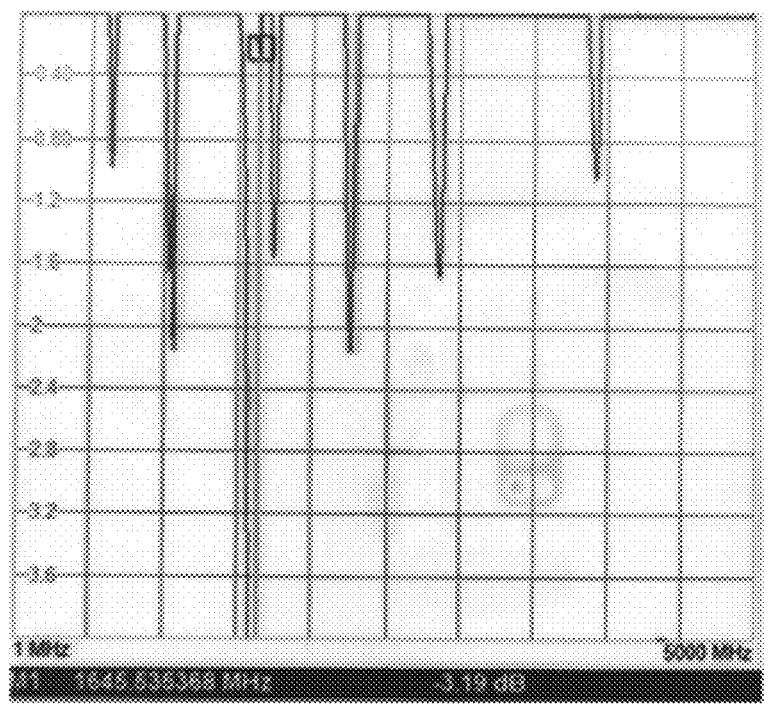

FIGS. 26A-26C show a time evolution of example spectra produced when an analyte was detected by a resonant gas sensor similar to that shown in FIG. 25D, but the system in this example used a separate virtual network analyser rather than an integrated microprocessor. The resonant gas sensor in this example contained a substrate that was paper with a silica layer deposited on the surface, and a printed spiral transducer and capacitive element connected in parallel. The capacitive element contained a sensing material with the particulate carbon described herein and a reactive chemistry additive containing PEUT. The analyte in this example is isopropyl alcohol mixed with acetone and water. FIGS. 26A, 26B and 26C show the reflected signal, such as S11, from the circuit after about 1-2 seconds, about 15 seconds and about 30 seconds, respectively. In the absence of any analyte the signal is a flat line with no features at 0 dB. FIG. 26A shows some evidence that an analyte is present after only about 1-2 seconds. Therefore, the design and materials of the resonant gas sensor in this example enable a fast detection of an analyte. FIG. 26C shows multiple peaks representative of the analyte detected and illustrates the capability of this type of resonant gas sensor to identify a species of analyte, such as such by comparing a detected spectrum with those in a stored library.

The AC signals used by the resonant gas sensors described above contain a set of frequencies, such as in a range from 1 MHz to 20 GHz, and the method by which the signal is applied can vary. For example, a single frequency sweep can be performed continuously, or periodically at various intervals, such as once every 1 second, 10 seconds, 1 minute, 10 minutes, or once an hour. In some cases, different sweeps with different resolutions, such as frequency spacing between the different frequencies within a range can be performed at different intervals.

In one non-limiting example, a first course sweep is performed followed by targeted sweeps. Other similar methods for supplying different frequencies to a resonant gas sensor are also possible in different implementations. In this example, a first fast/coarse sweep of the frequency range is performed by the microprocessor, and a peak is detected. After the first coarse sweep, the microprocessor can drive the resonant sensor to the peak and dither around it to more accurately ascertain the peak frequency and relative intensity values. Ascertained peak values can be compared to a library of analytes, and in some cases, if the library indicates a possible match, the microprocessor can be used to sweep to a second peak in the spectrum of a possible analyte to obtain a second indicator as a check to reduce the number of false positives. The peak values, and/or other features of measured spectra, are compared to a library of analytes using an integrated microprocessor, such as that shown in FIG. 25A, 25C, 25D or 25F, or communicating with a remote processor and/or database. Such a method containing a first course scan followed by targeted subsequent dither scans can be beneficial to provide high detection accuracy with lower power requirements than performing a fine scan over a large set of potential analyte resonant frequencies. To further save power, such a method can be performed periodically, such as once every 1 second, 10 seconds, 1 minute, 10 minutes, or once an hour. In some implementations, the system requirements can be relaxed to further save cost and power by targeting a +/— 20% accuracy level for the concentration of a measured analyte. Although such a system may not provide highly accurate concentrations, it can have low power requirements, such as less than 1 nW, or less than 1 pW, and have a low production cost, such as less than 1 US dollar per unit, or less than 5 US dollars per unit, depending on the complexity of the system and the number of analytes capable of being detected, and therefore still be useful in many applications where indication and detection of an analyte are needed and an accurate concentration measurement is not required, such as to detect the presence of an explosive inside of a mailed package, or detecting the occurrence of food spoilage in a packaged food product.

Chemiluminescence Sensors

Figure 27:
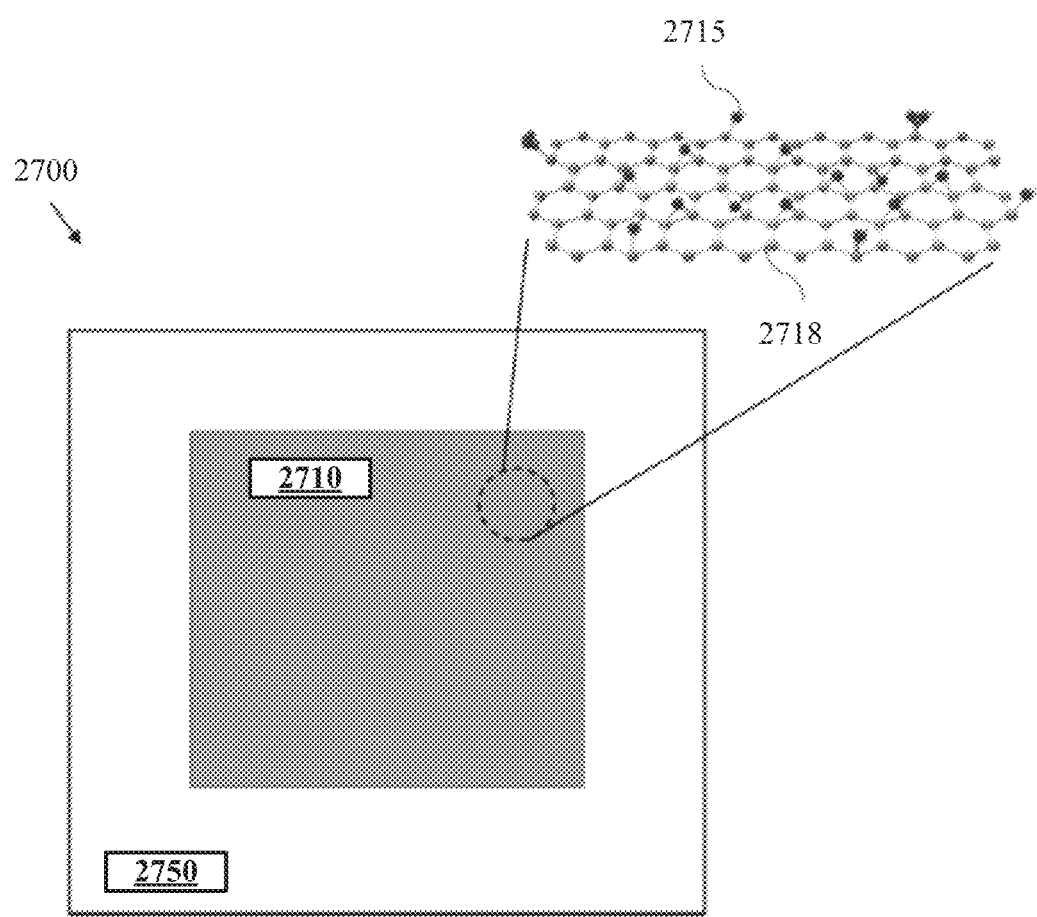
FIG. 27 shows a non-limiting example of a chemiluminescent gas sensor, in accordance with some implementations.

Other implementations include chemiluminescent sensors as shown in FIG. 27. The sensor 2700 includes a chemiluminescent composite material 2710 printed on a substrate 2750. The material 2710 includes a luminescent dye material 2715 tethered to a graphene-based material 2718, where the dye material is chosen based on being a receptor for a certain target chemical molecule. In some implementations, the graphene-based material 2718 is contained within the particulate carbon described herein. Detection of various functional groups of a target chemical is indicated by a wavelength shift in the absorption spectra of the dye. Due to electron transfer, there is a change in the structure and excitation energy of the dye. In other words, due to the presence of electron donating and withdrawing groups, the electronic state of the dye is changed, causing the change in color and wavelength. Some non-limiting example compounds for luminescent dyes include, for example, Ru(Bpy)3, or analogues of it; or Au, Cu or Ag pyrazolytes. For example, peroxidase or chemical vapors in contact with metallo-organic luminescent material can coordinate, resulting in a wavelength shift which can be visually observed. In some cases, the dye-sensitized graphene sheets, such as graphene oxide, are carboxyl-group functionalized. Due to the high surface area and beneficial structure of the particulate carbon described herein; the composite material provides a structure that results in higher sensitivity than conventional chemiluminescent sensors.

Sensor Systems

Figure 28:
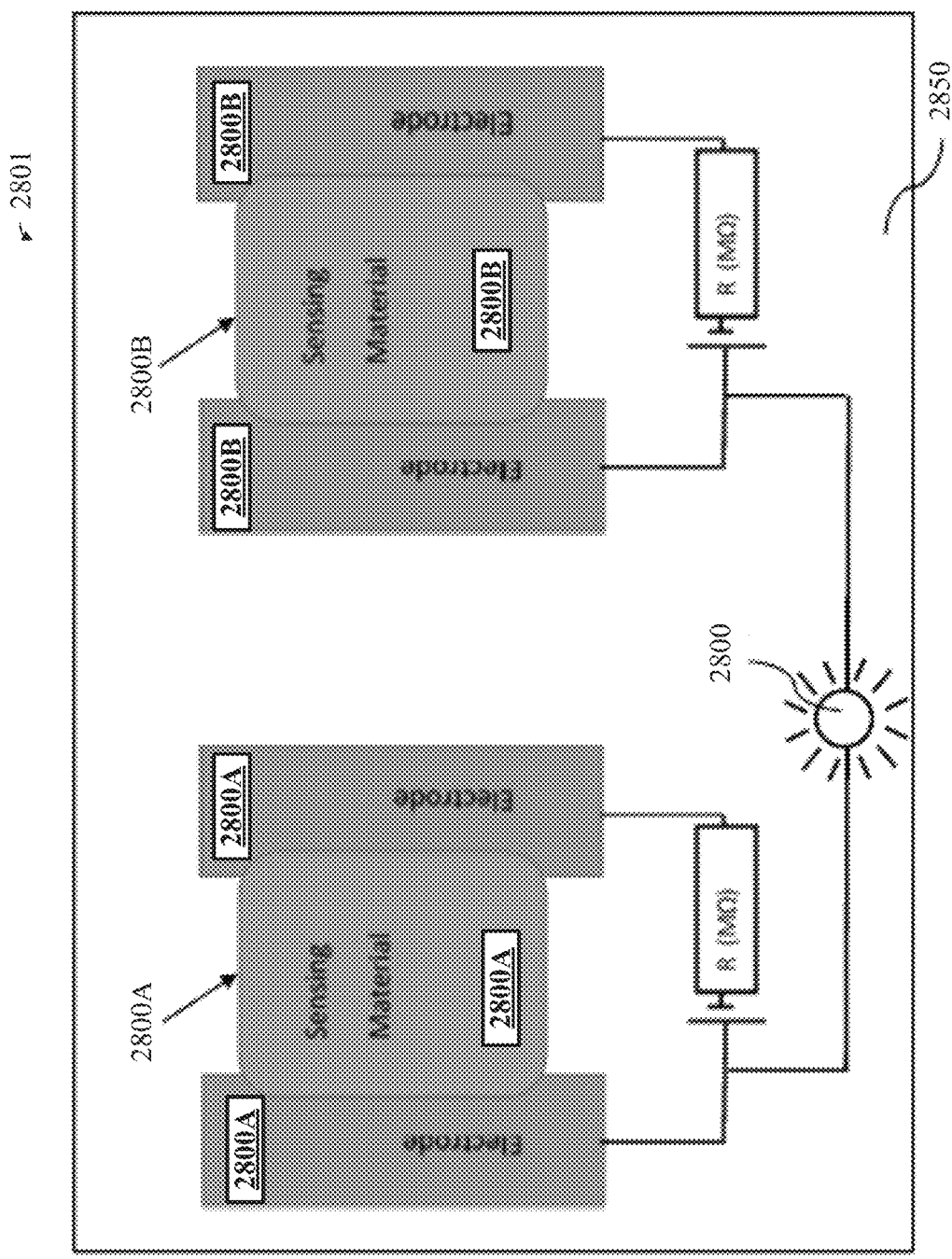
FIG. 28 shows a non-limiting example of a sensor system in which multiple individual chemical sensors are used for detecting an analyte, in accordance with some implementations.

FIG. 28 shows a non-limiting example implementation of a sensor system 2801 in which multiple individual gas sensors are used for detecting one or more chemical compounds (such as various analytes). Sensor system 2801 includes a first sensor 2800a for detecting a first target chemical, and a second sensor 2800b for detecting a second target chemical. In this implementation, both first sensor 2800a and second sensor 2800b are electrochemical sensors, but other types of sensors, described herein, can also be used. For example, the gas sensors of the sensor system may be electrochemical, high frequency, resonant, chemiluminescent, or a combination of these. In some cases, first sensor 2800a and second sensor 2800b are printed on the same substrate 2850, such as a label. Each sensor 2800a/b can include a first electrode 2810a/b, a second electrode 2811a/b, and an electrolyte 2820a/b, where the components include particulate carbon and redox mediators as described in relation to FIG. 21. Although two sensors 2800a and 2800b are shown in this example, more than two sensors can also be included. In some implementations, an array of sensors can be used to add functionality, such as the ability to detect multiple gases, subtract a background level of moisture and/or improve the sensitivity to an analyte. Furthermore, other non-printed sensors, such as IR sensors, can be included. As one example, an IR sensor can be included to detect NO2 groups.

An indicator 2860 is coupled to sensors 2800a and 2800b through electrical circuitry (not shown), where both sensors 2800a and 2800b must positively sense detection of their target chemical in order for the indicator 2860 to be activated. The combination of all the individual target substances being present indicates that a certain compound is present. Types of indicators 2860 that may be used include an optical indicator (such as a light emitting diode), an acoustic output, or a visual display such as a text or graphic read-out. In other implementations, the indicator 2860 may be part of the sensor devices, such as if the individual sensors themselves can provide a positive indication of detection through a color change of the sensing material, or other indicator mechanism. The sensor system 2801 represents implementations in which the presence of multiple sensors in one device are utilized to detect a combination of chemicals, in order to characterize an overall compound. The presence of multiple sensors can also help rule out false positives.

In the sensor systems for detecting a chemical compound in some implementations, the sensor systems include a first sensor configured to detect a first target chemical, a second sensor configured to detect a second target chemical that is different from the first target chemical, and a substrate on which the first sensor and the second sensor are printed. An indicator indicates when both the first sensor positively detects the first target chemical, and the second sensor positively detects the second target chemical.

Additionally, other components can be integrated with the gas sensors to add functionality to a gas sensors system. Some non-limiting examples of electro-active labels containing the present gas sensors, that also contain a display-based human/machine interface are devices that can display telemetry, Q-codes or bar codes, and/or icons. Example scenarios include telemetry, where information can be updated, and/or have an image such as a gage; a Q-code (QR code) or bar code, using digital data or number/text formats; and icons for packages where a color or image change is displayed. In these various scenarios, a change in the display, such as in the symbol or color, or a back-and-forth change, can be used to indicate the condition of the product. These display telemetry devices are a new approach to providing information about the contents of a package status, using a microprocessor-based machine and user detection of the conditions within a package. The present devices can also optionally include low power communications components (such as to communicate directly with other electronic devices).

In a non-limiting example, a cardboard shipping box was equipped with an electrochemical sensor similar to that shown in FIG. 23, a resonant sensor similar to that shown in FIG. 25D, integrated microprocessors to drive the sensors and detect signals from the sensors, a display to communicate visual information (such as a species of analyte detected) and a wireless communication chip (such as a Wi-Fi chip) to communicate information to other devices. The electronics were powered by an integrated battery. The sensing material in the electrochemical sensor and the resonant sensor in this example were both printed, and both contained the particulate carbon described herein. The beneficial properties of the particulate carbon coupled with the sensor designs enabled them to utilize low power (such as with currents from 0.1 microamps to 5 microamps) to detect analyte species. This example illustrates that gas sensors utilizing the particulate carbon described herein can be produced using low-cost low power driver/detection electronics that can be integrated into a small package. Furthermore, this example showed that such low cost printed gas sensors can also be integrated with other system components such as displays and communication chips.

Printing of Chemical Sensors

In some implementations, gas sensor components (such as electrodes and sensing materials) are printed from carbon-based inks (such as containing the particulate carbons describe herein). The electrical components of the present gas sensors can be printed on backing materials such as labels and integrated with other hardware components on a substrate. More than one sensor can be printed on the same substrate, such as multiple sensors of the same type, or different types of sensors (such as electrochemical, high frequency, chemiluminescent). Types of substrates—which also may be referred to as backing materials—include rigid or flexible substrates, card stock, labels, or other types of materials used for printing.

In some implementations, printed gas sensor components containing the particulate carbon described herein are further processed after printing to increase the conductivity of the printed components. For example, particulate carbon containing electrodes, transducers, and/or capacitive elements of the resonant gas sensors described herein can be further processed after initial printing to increase the conductivity of these printed components. In some implementations, the transducers described herein require high conductivities (such as greater than 3500 S/m, or greater than 5000 S/m, or greater than 10000 S/m, in different implementations) in order to perform as effective transducers, and in some cases these conductivities cannot be reached using printed particulate carbon without further processing. Some non-limiting examples of processes to improve the conductivity of printed particulate carbon materials are sintering and/or calendaring. For example, sintering can be performed using a plasma, laser or microwave energy. In some cases, the sintering process can locally heat the printed material and not affect the substrate and/or other underlying materials. In other implementations, calendaring is performed to increase the conductivity of the printed carbon materials. For example, calendaring using a heated roller, or a roller equipped with an energy source (such as microwave energy) to sinter and calendar simultaneously can increase the conductivity of the printed particulate carbon.

In other implementations, high conductivity printed gas sensor components can be formed by printing a mixture of the present particulate carbon with other conductive particles added to increase the conductivity of the printed components. For example, the electrodes, transducers, and/or capacitive elements of the resonant gas sensors described herein can be formed using such mixtures. Some non-limiting examples of conductive particles that can be mixed with the particulate carbon described herein are Ag, Sn and/or Sb particles. Printed components for gas sensors containing the particulate carbon and additional conductive particles can be advantageous in some implementations because the particulate carbon provides beneficial structure to the printed components (such as high surface areas), and the conductive particles improve the conductivity of the printed components.

The devices can be designed to operate in low power ranges, such as 0 to 1 volts, or less than 100 μW, or less than 1 μW. In some cases, the low power consumption is made possible by the high conductivity, the high surface area and mesoporous structure of the carbon-based materials used in printing the components, the small size of the devices, the choice of detection methodologies, and optionally the choice of display technologies. The overall device architecture may also use low power technology for the various system components (such as gas sensor and indicator).

In some implementations, the printed components are made from carbon-based inks and can be electrically coupled to each other and/or to one or more additional hardware components, which can be mounted on the substrate. The hardware components can be, for example, one or more of an output display, microcontroller units (MCU), switches, and capacitors, among others. The hardware components use information stored in, generated by, and/or communicated from the printed components, such as by processing or displaying data from the printed components. The present devices can also optionally include low power printed communications components.

In addition to the particulate carbon described herein, types of carbon materials for the various implementations of printed components can include, but are not limited to, graphene, graphenes (graphene-based materials), graphene oxide, reduced graphene oxide, graphite oxide, graphite intercalation compounds, graphite, graphene, carbon nano-onions, diamond, p-type diamond, n-type diamond, glassy carbon, amorphous carbon, activated carbon, carbon black and/or carbon nano-tubes, sulfur-based carbons (such as sulfur melt diffused carbon), and carbons with metal (such as nickel-infused carbon, carbon with silver nanoparticles, graphene with metal). The printed components can be printed by, for example, screen printing or ink-jet printing.

Reference has been made to implementations of the disclosed invention. Each example has been provided by way of explanation of the present technology, not as a limitation of the present technology. In fact, while the specification has been described in detail with respect to specific implementations of the invention, it will be appreciated that those skilled in the art, upon attaining an understanding of the foregoing, may readily conceive of alterations to, variations of, and equivalents to these implementations. For instance, features illustrated or described as part of one implementation may be used with another implementation to yield a still further implementation. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. A battery-powered analyte sensing system comprising:
   a printed battery comprising:
      an anode composed of a non-toxic biocompatible metal;
      a first carbon-based current collector in electrical contact with the anode;
      a three-dimensional hierarchical mesoporous carbon-based cathode;
      a second carbon-based current collector; and
      an electrolyte layer disposed between the anode and the cathode, the electrolyte layer configured to activate the printed battery when the electrolyte is released into one or both the anode and the cathode; and an analyte sensor comprising:
a sensing material; and
a reactive chemistry additive in the sensing material.

2. The battery-powered analyte sensing system of claim 1, wherein the non-toxic biocompatible metal includes one or more of Zn, Mg, or Al, and is configured to yield a cell voltage between approximately 1.5 volts and 3 volts.

3. The battery-powered analyte sensing system of claim 1, wherein the battery-powered analyte sensing system is configured to transform oxygen into water by exposing the oxygen to ambient air.

4. The battery-powered analyte sensing system of claim 1, wherein the electrolyte layer is configured to release into one or both the anode and the cathode in response to one or more of a pressure-activated rupture of the electrolyte layer or exposure of a hygroscopic compound to solid salts contained within the anode.

5. The battery-powered analyte sensing system of claim 1, wherein one or both the anode and the cathode comprise a three-dimensional scaffolded mesoporous carbon-based material.

6. The battery-powered analyte sensing system of claim 5, wherein the scaffolded mesoporous carbon-based material further comprises a plurality of electrically conductive three-dimensional aggregates formed of graphene sheets.

7. The battery-powered analyte sensing system of claim 6, wherein the three-dimensional aggregates form an open porous scaffold configured to provide electrically conductive paths between contact points of the graphene sheets.

8. The battery-powered analyte sensing system of claim 1, wherein the electrolyte layer is configured to be released based on an application of pressure to one or both the anode and cathode.

9. The battery-powered analyte sensing system of claim 1, wherein the battery-powered analyte sensing system is fabricated by one or more of three-dimensional printing or additive manufacturing techniques.

10. The battery-powered analyte sensing system of claim 1, wherein one or both the anode and cathode are three-dimensionally printed onto at least a portion of a container comprising one or more of card stock, cardboard, paper, or polymer-coated paper.

* * * * *